US008645073B2

(12) United States Patent
Gilbert et al.

(10) Patent No.: US 8,645,073 B2
(45) Date of Patent: Feb. 4, 2014

(54) METHOD AND APPARATUS FOR ALLELE PEAK FITTING AND ATTRIBUTE EXTRACTION FROM DNA SAMPLE DATA

(75) Inventors: Kenneth H. Gilbert, Knoxville, TN (US); John Douglas Birdwell, Oak Ridge, TN (US); Tse-Wei Wang, Oak Ridge, TN (US); Dale V. Stransberry, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 1555 days.

(21) Appl. No.: 11/913,098

(22) PCT Filed: Jul. 28, 2006

(86) PCT No.: PCT/US2006/029434
§ 371 (c)(1),
(2), (4) Date: Oct. 30, 2007

(87) PCT Pub. No.: WO2007/024408
PCT Pub. Date: Mar. 1, 2007

(65) Prior Publication Data
US 2009/0228245 A1  Sep. 10, 2009

Related U.S. Application Data

(60) Provisional application No. 60/709,424, filed on Aug. 19, 2005.

(51) Int. Cl.
*G01N 33/48* (2006.01)
*C12Q 1/68* (2006.01)

(52) U.S. Cl.
USPC .............................................. 702/19; 435/6

(58) Field of Classification Search
None
See application file for complete search history.

(56) References Cited

U.S. PATENT DOCUMENTS

| | | | |
|---|---|---|---|
| 5,121,443 A | 6/1992 | Tomlinson | |
| 6,438,499 B1 | 8/2002 | Hayashi | |
| 6,741,983 B1 | 5/2004 | Birdwell et al. | |
| 7,162,372 B2 | 1/2007 | Wang et al. | |
| 2002/0116135 A1 | 8/2002 | Pasika et al. | |
| 2005/0059046 A1 | 3/2005 | LaBrenz et al. | |

FOREIGN PATENT DOCUMENTS

| WO | 9953423 | 10/1999 |
|---|---|---|
| WO | WO 99/53423 | 10/1999 |

OTHER PUBLICATIONS

International Preliminary Examination Report dated Jan. 11, 2008 (PCT/US06/029434).
Frank Alsmeyer et al., "Automatic Generation of Peak-Shaped Models," Applied Spectroscopy, vol. 58, No. 8, 2004, pp. 986-994.
International Search Report (PCT/US2006/029434) dated Dec. 28, 2006, 16 pages.
Robert C. Holte, Very Simple Classification Rules Perform Well On Most Commonly Used Datasets (Kluwer Academic Publishers, Boston) 1993, pp. 63-90.
Computer Software Reviews, J. Am. Chem. Soc., vol. 114, No. 20, 1992, pp. 7961-7962.
Baeza-Baeza, J. J. et al., Prediction of Peak Shape as a Function of Retention in Reversed-Phase Liquid Chromatography, Journal of Chromatography A, 1022, (2004) pp. 17-24.
Caballero, R. D. et al., Parabolic-Lorentzian Modified Gaussian Model for Describing and Deconvolving Chromatographic Peaks, Journal of Chromatography A, 954, (2002), pp. 59-76.
Di Marco, Valerio B. et al., Mathematical Functions for the Representation of Chromatographic Peaks, Journal of Chromatography A, 931, (2001), pp. 1-30.
Eanes, Ritchie C. et al., Peakfitter—An Integrated Excel-based Visual Basic Program for Processing Multiple Skewed and Shifting Gaussian-like Soectral Peaks Simultaneously: Application to Radio Frequency Glow Discharge Ion Trap Mass Spectrometry, Spectrochimica Acta Part B, 55, (2000), pp. 403-428.
Erny, Guillaume L. et al., Electromigration Dispersion in Capillary Zone Electrophoresis Experimental Validation of Use of the Haaroff-Van der Linde Function, Journal of Chromatography A, 959, (2002) pp. 229-239.
Lan, Kevin et al., A Hybrid of Exponential and Gaussian Functions as a Simple Model of Asymmetric Chromatographic Peaks, Journal of Chromatography A, 915, (2001), pp. 1-13.
Li, Jianwei, Comparison of the Capability of Peak Functions in Describing Real Chromatographic Peaks, Journal of Chromatography A, 952, (2002), pp. 63-70.
Marquardt, Donald W., An Algorithm for Least-Squares Estimation of Nonlinear Parameters, Journal of the Society for Industrial and Applied Mathematics, vol. 11, No. 2 (Jun. 1963), pp. 431-441.
Nikitas, P. et al., On the Equations Describing Chromatographic Peaks and the Problem of the Deconvolution of Overlapped Peaks, Journal of Chromatography A, 912, (2001), pp. 13-29.
Pai, Su-Cheng, Temporally Covoluted Gaussian Equations for Chromatographic Peaks, Journal of Chromatography A, 1028, (2004), pp. 89-103.
Steffen, B. et al., A New Mathematical Procedure to Evaluate Peaks in Complex Chromatograms, Journal of Chromatography A, 1071, (2005), pp. 239-246.
Walsh, S. et al., Non-Linear Curve Fitting Using Microsoft Excel Solver, Talanta, vol. 42, No. 4, 1995, Great Britain, pp. 561-572.
Levenberg, Kenneth, "A Method for the Solution of Certain Non-Linear Problems in Least Squares," Quarterly of Applied Mathematics, 2:164-168, 1944.
Pap, T. L. et al., "Application of a New Mathematical Function for Describing Chromatographic Peaks," Journal of Chromatography A, Elsevier, 930, pp. 53-60, 2001.
Coleman, Thomas et al., "Optimization Toolbox for Use with MATLAB," User's Guide, v. 2, The MathWorks, Inc., Natick, MA, selected portions re Least-Squares (Curve Fitting): 1-3 to 1-5, 1-37 to 1-39, 1-50 to 1-51, 2-17 to 2-22 and 3-11 to 3-13, Jan. 1999.

(Continued)

*Primary Examiner* — Anna Skibinsky
(74) *Attorney, Agent, or Firm* — Cameron LLP

(57) ABSTRACT

Analysis of DNA is critical to many applications including identifying perpetrators of crimes based on genetic evidence left at crime scenes. An initial step to analyzing DNA data is detection, identification, and quantization of allele peaks in the DNA data. The invention provides a method and apparatus for accurately and expeditiously performing this initial step by sequentially checking unfitted peaks against various models including a default model, a hybrid peak model, a dual fit model and, in special situations, a narrow fit function and a saturated fit function.

25 Claims, 42 Drawing Sheets

(56) References Cited

OTHER PUBLICATIONS

Pozo, Roldan, "Template Numerical Toolkit," obtained using the WayBackMachine from math.nist.gov/tnt/index.html, National Institute of Standards and Technology, pp. 1-2, Last Modifed Mar. 31, 2004.

Unkown Author, "The Mathworks—MATLAB and Simulink for Technical Computing," obtained from web.archive.org, The MathWorks, Inc., 2005.

Unknown Author, "solver.com," Frontline Systems, Inc., obtained using the WayBackMAchine from www.solver.com, 2005.

Bertsekas, Dimitri P., Nonlinear Programming, 2nd Ed., Athena Scientific, Chapter 1, Unconstrained Optimization (including Optimality Conditions 1.1 and Gradient Methods—Convergence 1.2), 1999.

Butler, John M., Forensic DNA Typing, Biology & Technology behind STR Markers, Academic Press, Chapter 13, STR Genotyping Issues, 2001.

Butler, John M., Forensic DNA TYPING, Biology & Technology behind STR Markers, Second Edition, Academic Press, Chapter 15, STR Genotyping Issues, 2005.

Budowle, Bruce, et al., Population Data on the Thirteen CODIS Core Short Tandem Repeat Loci in African Americans, U.S. Caucasians, Hispanics, Bahamians, Jamaicans, and Trinidadians, Journal of Forensic Science, 44(6), pp. 1277-1286, 1999.

Budowle, Bruce, et al., CODIS STR Loci Data from 41 Sample Populations, Journal of Forensic Science, 46(3), pp. 453-489, 2001.

Gomez, Claude et al., Engineering and Scientific Computing with Scilab, Birkhauser, Sectons 8.4-8.4.3, pp. 280-292, 1999.

"An Expert System for Scoring DNA Database Profiles"; Mark W. Perlin, Ph.D., MD; Cybergenetics, Pittsburgh, PA.; Eleventh International Symposium on Human Identification, Biloxi, MS; Oct. 29, 2000.

"Using Quality Measures to Facilitate Allele Calling in High-Throughput Genotyping"; Genome Research; Birgir Palsson, Frosti Palsson, Mark Perlin et al.; 1999 9: 1002-1012.

METHOD AND APPARATUS FOR ALLELE PEAK FITTING AND ATTRIBUTE EXTRACTION FROM DNA SAMPLE DATA

This application is a US National Stage application of and claims priority to PCT/US06/029434, filed Jul. 28, 2006 which claims the benefit of U.S. Provisional Application 60/709,424, filed Aug. 19, 2005, both applications being hereby incorporated by reference in their entirety.

The U.S. government retains certain rights to this invention due to funding provided by contract J-FBI-03-196 awarded by the Department of Justice, Federal Bureau of Investigation.

FIELD OF THE INVENTION

The invention relates to the area of interpreting allele peak data obtained from DNA analysis. More specifically, the invention relates to a method for selecting parameters of allele peak models as a means to fit allele peak data, and for choosing among possible allele fit types to obtain parameters that accurately characterize allele peak data. The invention may be generally applied to interpretation of any raw data represented as peaks in a two-dimensional read out.

BACKGROUND OF THE INVENTION

Extracting allele peak parameters from raw DNA data, e.g., electropherogram, chromatographic, or spectral data, is a task required in many disciplines. A problem associated with extracting allele peak parameters is the fitting of an analytical curve to a set of peak data to obtain a best fit of the data in order to find the peak model parameters that represent each peak.

Analytical equations are needed to model peaks. The basic shape of an ideal chromatographic peak is similar to that of a Gaussian curve. Many different equations have been used to model peaks in various chromatographic applications [7, 10, 13, 14, 16, 17, 20, 21]. Di Marco and Bombi [17] have reviewed 86 mathematical functions that have been proposed to fit chromatographic peaks.

After an analytical equation such as the Gaussian model has been chosen to model a peak, a method must then be chosen to extract the optimal parameters that would fit the data. An optimization approach is a common method for addressing this issue. It is important to choose an optimization method that will converge given the peak model equation. Many investigators employ commercial software to perform fits as opposed to developing their own system. The Microsoft Excel Solver tool [2], which uses the Levenberg-Marquardt method [15, 18], has been used frequently to perform fits [11, 16, 19, 23]. The in-house software developed in [14] also uses the Levenberg-Marquardt method.

There are two classes of optimization methods: constrained and unconstrained. The Gauss-Newton method is unconstrained, which can be implemented simply and is less computationally intensive than constrained optimization methods, but allows the solution parameter values to be arbitrary. Most of the reviewed publications used commercial optimization software rather than software developed 'in-house'. Lack of control over the fitting protocols or parameters is a concern when using commercial software. In 1994 Walsh and Diamond [23] discussed the use of Microsoft Excel Solver for fitting curves to non-linear data. Their routine requires the user to select the data to be fitted, choose a model equation for the given data, and manually provide an initial guess of parameters for the model equation. They evaluated Solver's ability to fit chromatography peaks, fluorescence decay processes, and ion-selective electrode characteristics. For chromatography peaks, they provided a comparison of fitting using 3 different models: Gaussian, exponentially modified Gaussian (EMG), and tanks-in-series. Of these models, the EMG was found to best fit the given peak data. They did not elaborate on guidelines for guessing the initial parameters or the selection of the appropriate model to use for fitting a particular peak.

In 2000, Eanes and Marcus [11] extended the use of Microsoft Solver to fit Gaussian-like spectral peaks. Using Visual Basic, they developed a program to process multiple peaks simultaneously (up to 3) for radio frequency glow discharge ion trap mass spectra. The summation of multiple peak models was used to perform the multiple peak fits. The software used Microsoft Solver to perform the optimization and Visual Basic macros to provide a graphical user interface and manage the peak data. A dialog box is used for users to set initial parameters and various fitting settings for each set of peak data fitted. Multiple spectra of the same scan can be performed at the same time with the software, but user input appears to be required for each new peak or group of peaks to be processed. Adjustment to various peak models was accomplished by a generic template used by the software. Both Gaussian and Lorentzian peak models were implemented; however, each model type was implemented separately with a different program.

A comparison of the performance in fitting by a series of peak model equations was made by Li in 2001 [16] who performed fitting using an empirically transformed Gaussian, polynomial modified Gaussian, generalized exponentially modified Gaussian, and hybrid function of the Gaussian and truncated exponential functions. Li also used Microsoft Solver to perform the nonlinear optimization where the user explicitly set the initial parameters. The quality of fit was determined by the sum of squares of the residuals; the empirically transformed Gaussian function was found to give the best fit based on this quality measure. The four models used had varying degrees of complexity, and they did not explicitly give timing or iteration results for the fits. However, the hybrid function of Gaussian and truncated exponential functions performed second best among the functions tested and contained only four parameters compared to the seven parameters used in the empirically transformed Gaussian function.

An automatic curve fitting algorithm was described by Alsymeyer and Marquardt in 2004 [6]. The algorithm is automatic in that it does not require human interaction or a priori knowledge of peak initial parameters or other spectrum properties. The method fits the peaks in the entire spectrum with a single model and iteratively adds additional peak components to the model equation until a stopping condition is fulfilled generally based on a goodness-of-fit criteria such as the F-Test. Initial parameters for the peak are determined by analyzing the data where the largest fitting error was found from the previous model fit. The peak model equation used is the Voigt function, which is a convolution of the Lorentzian and Gaussian distributions. The method starts with a pure baseline model and it should be noted that each iteration of the algorithm adds a peak to the existing model, thus adding additional parameters to the model to be optimized. The authors state that a sequence of 50 peak functions takes overnight to run with the current implementation. The current implementation is written in MATLAB without explicitly attempting to optimize performance, and they suggest that the use of a compiled programming language could help improve performance. Infrared and Raman spectra were modeled and the authors were able to obtain results with a good fit with respect to fitting error; however, they add that the resulting models are not necessarily physically correct. This implies that the model obtained fits closely to the experimental data, but that the peaks the model describes may not represent the actual physical components of the spectra.

Steffen et al. in 2005 presented another automatic method for fitting peaks in complex chromatograms [22]. Their approach involved extracting peak shapes (parameterized models) directly from the chromatogram and forming a standard peak shape based on the average shape of typical peaks found in the given data. The method defines an improved baseline for the data and then automatically detects peaks using maxima of the signal and minima of the second derivative. It fits the peaks with a hyperbolic scaling function that is applied to the standard peak model. They mention that peaks that differ too much from the standard peak may need to be identified and possibly fitted with a differently shaped model, but do not elaborate on specific methods for accomplishing this task. They implemented the software in Scilab code [12] and performed fitting on a large number of chromatograms (around 1,000). Comparison of their fit results to that of traditional interactive analysis proved to be fairly compatible. Verification using synthetic chromatograms yielded good general results, but they had problems with detection of extremely small peaks in difficult synthetic chromatograms. They indicate that the heuristic parameters in the implementation can be utilized for refinement of the fitting to improve results and tune the system.

Also, expert systems are known in other disciplines which facilitate the inclusion of expertise in the decision making process. Consequently, there is a need in the art for an allele peak fitting framework to properly fit raw DNA peak data for subsequent calling of alleles by experts in the field, or by automatic peak processing by an expert system.

SUMMARY OF THE INVENTION

One embodiment of the invention is a method of analyzing two-dimensional graphical data in which the graphical data exhibit peaks. A first mathematical equation model is optimized to determine a first set of peak parameters. A second mathematical equation model is determined for further graphical analysis. The optimization includes determining a peak parameter vector.

Another embodiment of the invention is an alternative method of analyzing two-dimensional graphical data in which the graphical data exhibit peaks. An equation model to determine peak parameters of maximum height, peak center location, and width are optimized. The optimization includes determining a parameter vector that minimizes cost.

A further embodiment of the invention is a method for deciding a peak fitting model and peak parameters to accurately characterize two-dimensional peak data. A first peak fitting model is tested and potential peak parameters are found to fit peaks in two-dimensional data. The quality of the peak fitting model is assessed. The first tested peak fitting model and the potential peak parameters to analyze the data are selected if the peak fitting model is acceptable. A second peak fitting model is tested and assessed for quality if the first peak fitting model is not acceptable.

An additional aspect of the invention is the inclusion of expertise in the decision making process. For example, an expert such as a forensic scientist or the use of an expert system with automatic peak processing could assist in deciding which peak fitting model is most appropriate. Automatic peak processing via an expert system is advantageous for high volume peak processing, allowing successful processing on all but a small percentage of peaks in the raw data.

DETAILED DESCRIPTION OF THE INVENTION

Figure 1:
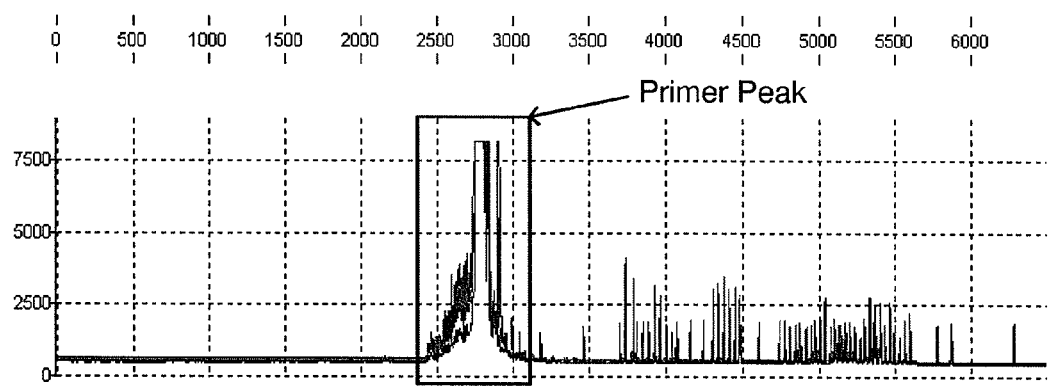
FIG. 1: An electropherogram with all four color channels superimposed to show the primer peak for the data in the run. The end of the primer peak indicates the start of the allelic peak data region.

The purpose of fitting peak data is to accurately determine the characteristics of a given peak, most importantly the maximum peak height and peak center position. A method must be devised for extracting these values from peak data. In one embodiment of the invention the peak data is fitted for the purpose of properly calling alleles.

Proper allele calling is essential to methods which resolve DNA mixtures, e.g., see U.S. application Ser. No. 10/265,908, filed Oct. 8, 2002, now U.S. Pat. No. 7,162,372, issued Jan. 9, 2007. Allelic information is input into these methods and analyzed to assign genotype profiles to individuals that contribute to the DNA mixtures. Proper allele calling is also necessary for formation of accurate genotype databases that store genotype information and/or can be searched to match genotype information, e.g., see U.S. Pat. No. 6,741,983, issued May 25, 2004.

An allele refers to the specific gene sequence at a locus. A locus refers to the position occupied by a segment of a specific sequence of base pairs along a gene sequence of DNA. At most two possible alleles can be present at one locus of a chromosome pair for each individual: one contributed by the paternal and the other contributed by the maternal source. If these two alleles are the same, the individual is homozygous at that locus. If these two copies are different, the individual is heterozygous at the locus. There are multiple alleles that can be contributed by either parent at each locus.

A genotype or DNA profile is the set of alleles that an individual has at a given locus. A genotype or DNA profile may also comprise the sets of alleles that an individual has at more than one locus. For example, a genotype or DNA profile may comprise the set of alleles at each of at least 2 loci, 3 loci, 4 loci, 5 loci, 7 loci, 9 loci, 11 loci, 13 loci, or 20 loci.

To obtain a DNA profile, one may need to first isolate, purify, and amplify the DNA. It is also possible that one will directly obtain raw DNA data from others for analysis.

Raw DNA data may be obtained from a nucleic acid sample, usually a DNA sample. Sources of nucleic acid include any tissue, and may include blood, semen, vaginal smears, sputum, nail scrapings, or saliva. The nucleic acid sample may comprise chromosomal DNA or mitochondrial DNA.

The raw DNA data may be obtained by amplification of a nucleic acid sample and subsequent separation. Amplification may be performed by any suitable procedures and by using any suitable apparatus available in the art. For example, enzymes can be used to perform an amplification reaction, such as Taq, Pfu, Klenow, Vent, Tth, or Deep Vent. Amplification may be performed under modified conditions that include "hot-start" conditions to prevent nonspecific priming. "Hot-start" amplification may be performed with a polymerase that has an antibody or other peptide tightly bound to it. The polymerase does not become available for amplification until a sufficiently high temperature is reached in the reaction. "Hot start" amplification may also be performed using a physical barrier that separates the primers from the DNA template in the amplification reaction until a temperature sufficiently high to break down the barrier has been reached. Barriers include wax, which does not melt until the temperature of the reaction exceeds the temperature at which the primers will not anneal nonspecifically to DNA.

A commercial kit such as ABI's AmpFISTR® COfiler, Profiler Plus, and Identifiler may be employed to perform the amplification reaction. These kits contain fluorescent dye-tagged DNA primers that bind to specific sites within each locus (the two terminals).

The kits may include ladders. The ladders are allelic ladders and these provide reference peak signals for all of the common alleles of each locus. The kit may define the loci and allele ranges for each locus that it can identify.

There may be an internal sizing standard (ISS) on one of the dye channels that is used for calibration of the size of DNA fragments in base-pair units (e.g., ROX (red) channel for COfiler and Profiler Plus; LIZ (orange) channel for Identifiler). The calibration process determines the mapping between scan unit and DNA fragment size (in base pairs) that enables the expert system to accurately determine peak sizes in base pairs in DNA sample data from knowing the scan unit position of the peak's center point. The ISS also determines the region of interest (ROI) for each data set.

Figure 4A:
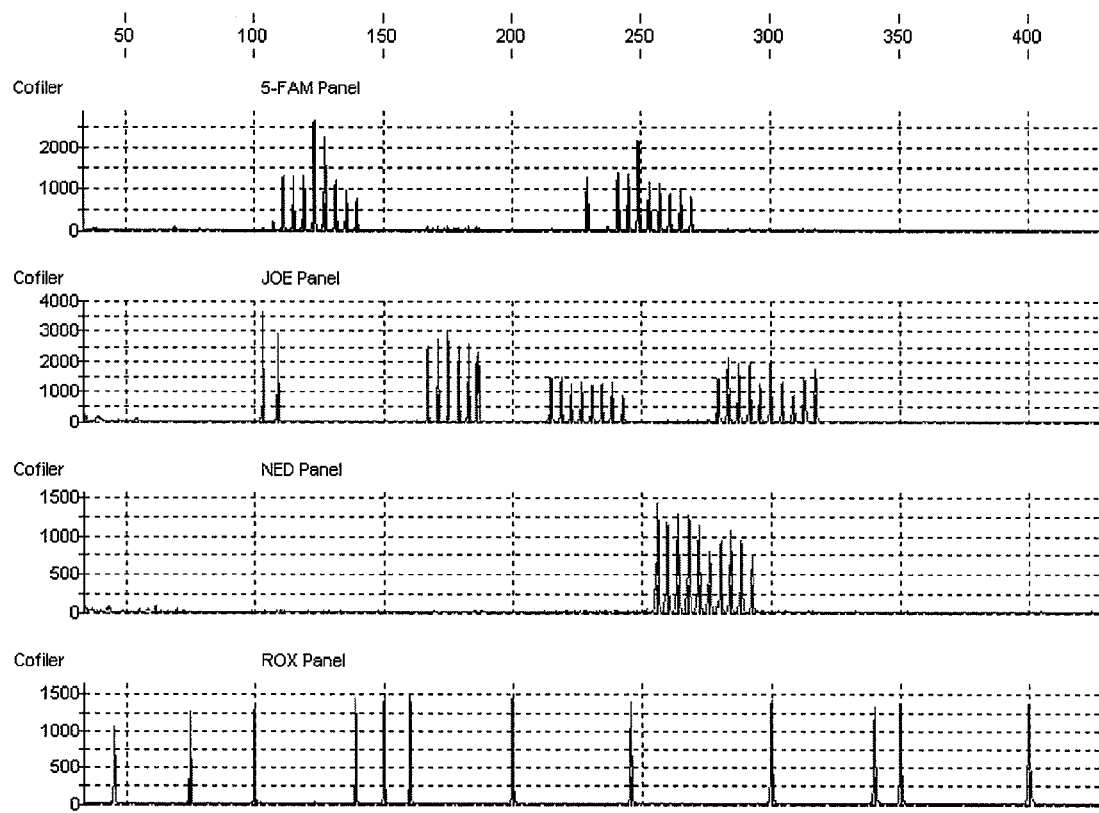
FIG. 4: Example COfiler ladder and sample runs. (a) The ladder run contains all the alleles for the different loci in the COfiler kit. (b) The sample shows peaks for the alleles contained in this run.
Figure 4B:
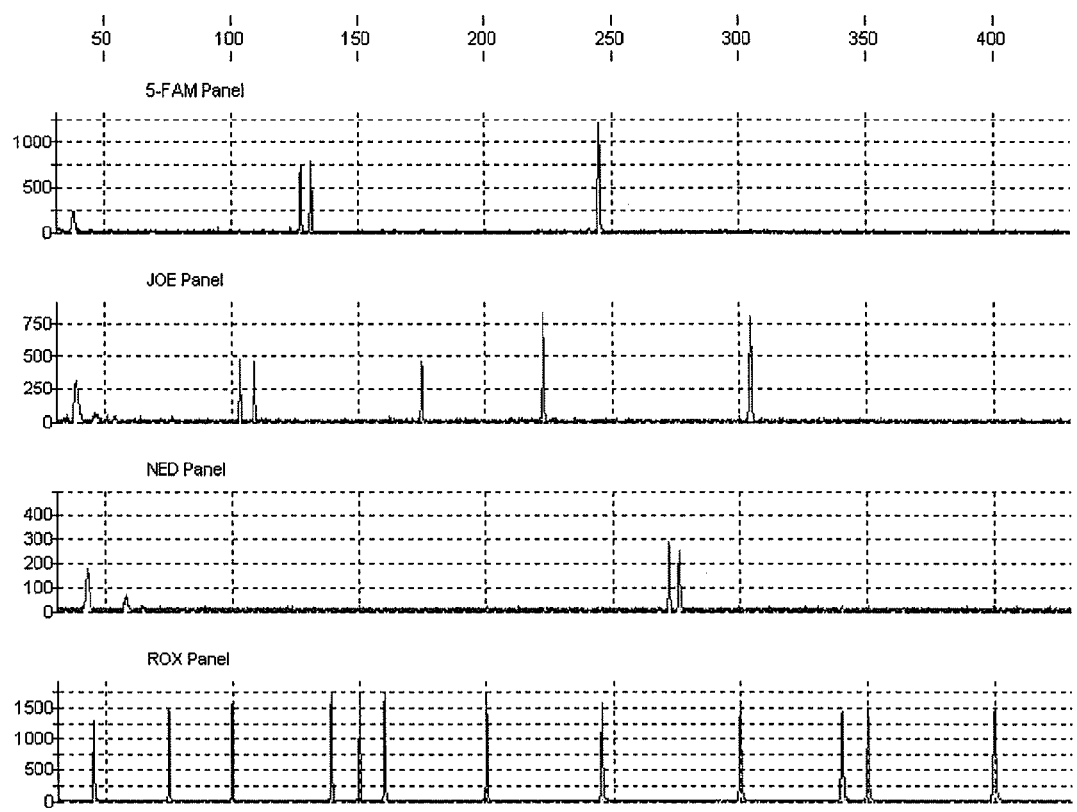

Prior to electrophoresis, the same internal sizing standard may be added to the amplified samples for calibration purposes. This allows the alleles in the other channels to be matched up with the ladder alleles and called. There is only a half base-pair tolerance when calling alleles, so accuracy of the peak center positions is paramount in correctly designating alleles. The internal sizing standard can be seen in the ROX (red, or bottom) channel in FIG. 4. The other channels show the different alleles that are matched between the ladder and the sample using the ISS. FIG. 4 shows an electropherogram of a ladder sample using the COfiler amplification kit. The differences between the kits are the particular loci they can amplify and the dyes used.

The polymerase chain reaction (PCR) amplification may include negative control and positive control sample runs for quality assurance. The negative control undergoes the PCR reaction but does not contain any DNA template and can indicate if there has been contamination in the process. The positive control contains a known DNA sample and is used to test that the system is amplifying and detecting properly.

The products of the amplification reaction are detected as different alleles present at a locus or loci. The alleles of at least one locus are amplified and detected after the amplification reaction. If desired, however, the alleles of multiple loci, e.g., two, three, four, five, six, ten, fifteen, twenty, twenty-five, or thirty, or more different loci may be detected after amplification. Sets of loci may include at least two, three, five, ten, fifteen, twenty, thirty, or fifty loci. Amplification of all of the alleles may be performed in a single amplification reaction or in a multiplex amplification reaction. Alternatively, the sample may be divided into several portions, each of which is amplified with primers that yield product for the alleles present at a single locus. Multiplex amplification is preferred.

The different alleles at a locus typically are detected because they differ in size. Alleles can differ in size due to the presence of repeated DNA units within loci. A repeated unit of DNA can be, e.g., a dinucleotide, trinucleotide, tetranucleotide, or pentanucleotide repeat. Short Tandem Repeats (STR) are DNA segments with repeat units of 2-6 bp in length [24]. The repeated unit can be of a longer length that ranges from ten to one hundred base pairs. These are medium-length repeats and may be referred to as a Variant Number of Tandem Repeat (VNTR) [24]. Repeat units of several hundred to several thousand base pairs may also be present in a locus. These are the long repeat units.

Short tandem repeat (STR) DNA markers are employed by the forensics community to differentiate between different alleles. The variations in STR alleles between individuals are examples of length polymorphism. The allele names correspond to the number of repeats of base-pair unit patterns at a particular locus. For example, the TH01 locus uses the simple repeat structure $[AATG]_n$ where allele number 9 has n=9 repeats of that pattern among its sequence segment. Some loci have more complicated repeat structures such as VWA with $[TCTA][TCTG]_{3-4}[TCTA]_n$ where allele number 12 has the structure $TCTA[TCTG]_4[TCTA]_7$ [9]. The larger the number of an allele name, the longer the DNA sequence of the allele, and therefore, the heavier the allele. The FBI currently uses thirteen core STR loci for its Combined DNA Index System (CODIS) database for human identification purposes.

The number of repeated units at a locus may be, for example, at least five, at least ten, at least fifteen, at least twenty, at least twenty-five, or at least fifty units. The effect of these repeated units of DNA is the presence of multiple types of alleles that an individual can possess at any given locus that can be detected by size [24].

Preferably, alleles that harbor different numbers of STR repeat units are detected. More than 8000 STRs (loci) scattered across the 23 pairs of human chromosomes have been collected in the Marshfield Medical Research Foundation in Marshfield, Wis. [24]. Preferably, alleles at the 13 core loci used by the FBI Combined DNA Index System (CODIS): CSF1PO, FGA, TH01, TPOX, VWA, D3S1358, D5S818, D7S820, D8S1179, D13S317, D16S539, D18S51, and D21S11 [25], are detected.

It is also contemplated that amplification may be performed to detect an allele by amplifying microsatellite DNA repeats, DNA flanking Alu repeat sequences, single nucleotide polymorphisms, or y-STR DNA, or any other known polymorphic region of DNA that can be distinguished based on the size of different alleles.

After PCR, the amplified DNA molecules may be separated using capillary electrophoresis. This process utilizes an electrical field to separate the molecules across a fluid-filled capillary tube. The rate at which they move is directly related to the size of the molecule. Larger molecules move more slowly than smaller molecules. Fluorescent dyes that are attached to each DNA segment are detected by laser excitation as they pass through the detector window. Their fluorescence is detected by sensors that measure the intensity of the fluorescence emitted by the molecule. The presence of a DNA fragment will ideally appear as a Gaussian-like peak in the collected data signal. The strength of the signal is measured in relative fluorescent units (RFU), and the fluorescent data are plotted with respect to scan-unit (a measurement proportional to a fixed time interval) producing an electropherogram of the DNA sample.

In an electropherogram, there is a large peak corresponding to the DNA primers (FIG. 1). The (right) end of this primer peak indicates the start of the region of interest (ROI), encompassing allelic peak data.

Electropherogram data may be acquired using either the ABI 310 or ABI 3100 Genetic Analyzer [1]. These units use capillary electrophoresis with multiplex color fluorescence detection. The four dyes used for COfiler and Profiler Plus kits are as follows: 5-FAM (blue), JOE (green), NED (yellow), and ROX (red). Identifiler uses the dyes named 6-FAM (blue), VIC (green), NED (yellow), PET (red), and LIZ (orange). Detectors with wavelengths tuned to each of the colors record the signal's relative fluorescence strength as the sample moves through the capillary detector window; however, there is fluorescence emission overlap among the different color wavelengths. To remove these overlapping contributions, a mathematical step using a color matrix is first applied to the multi-color channel electropherogram data. This is a stage where the ABI 310 and ABI 3100 process differs. The ABI 310 outputs the raw fluorescent measurement that has not gone through color separation, whereas the ABI 3100 outputs already color-separated fluorescent intensity data. The impact of color separation on peak fitting are discussed below.

Any method that separates amplification products based on size can be used to generate the raw DNA data. The amplification products may be separated by electrophoresis in a gel, or mass spectrometry. For example, a Beckman Biomek RTM 2000 Liquid Handling System can be used to generate the raw DNA data. Optical density or optical signal can be used to generate the raw DNA data after gel or capillary electrophoresis.

Furthermore, any other type of genetic analyzer may be used to generate raw DNA data. These types of genetic analyzers are well known to those of skill in the art and include, e.g., DNA chips.

The raw DNA data may be in an electropherogram, a chromatograph, it may be represented as spectral data, or any other type of graphical depiction that may be seen as exhibiting peaks.

Figure 2A:
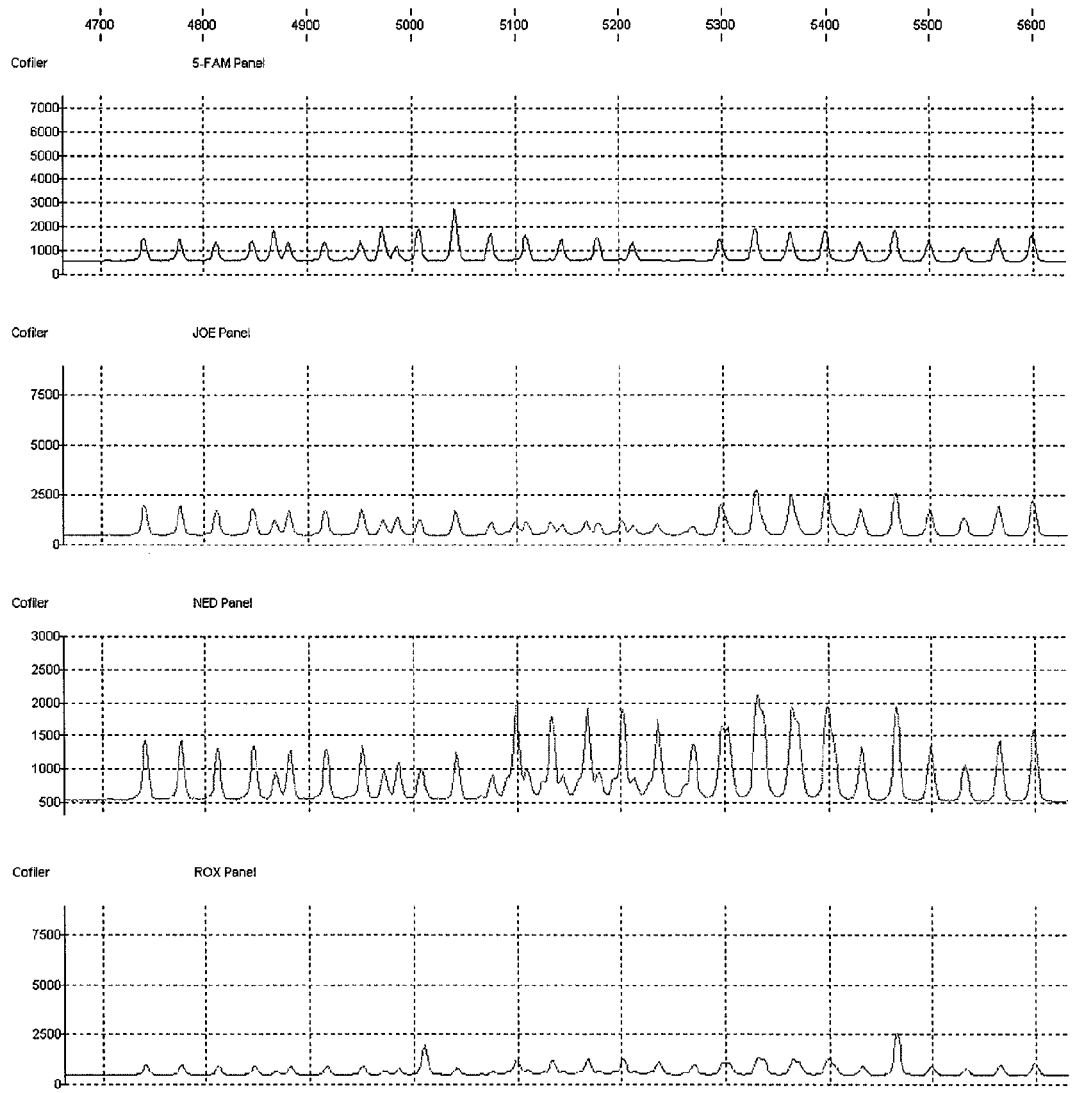
FIG. 2: The effect of color separation on the raw electropherogram data. The overlapping spectra can be observed by the large number of peaks in the data before color separation. After color separation, the contributions of the other dyes are removed from each channel. This reveals the peaks due to each dye/primer family alone. (a) Before color separation. (b) After color separation.
Figure 2B:
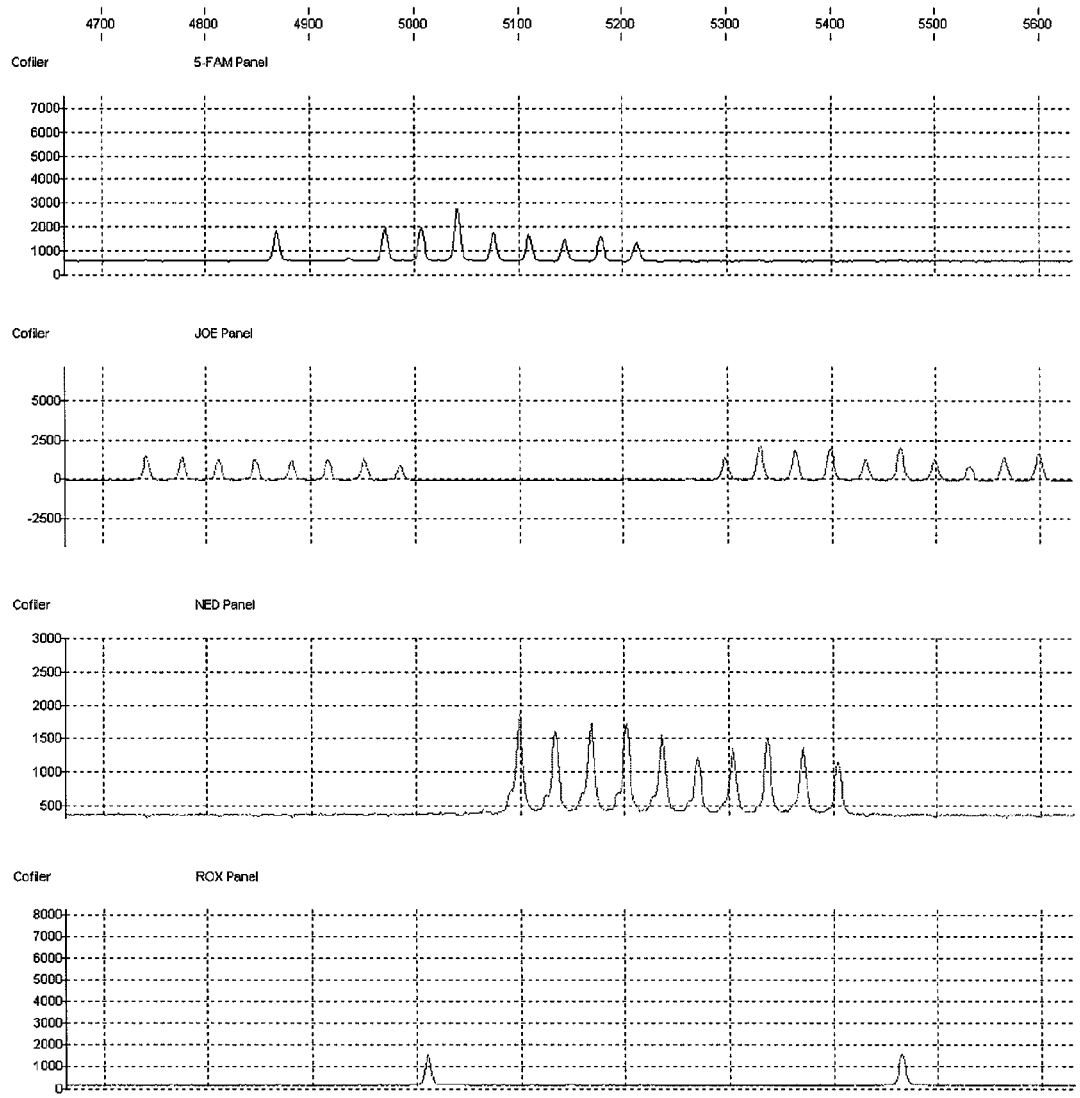

If the raw DNA data is present in an electropherogram, the electropherogram may need some data preprocessing before it can be analyzed. Color separation of the spectra may be performed first (in the case of ABI 310 data). FIG. 2 shows all four color channels before (a) and after (b) color separation. The overlapping spectral sensitivities of the detectors can cause additional peaks in each color panel. After separation, the contributions of dye signals across color channels are removed, revealing the peaks due to each dye/primer family.

Figure 3A:
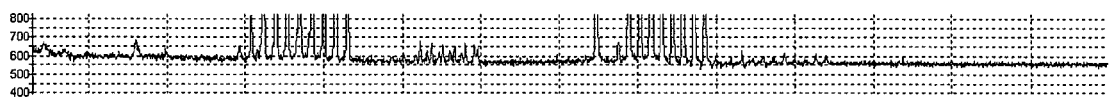
FIG. 3: The effect of baseline correction on the electropherogram data. Before baseline correction the data is above 550 RFU, which indicates the offset between the signal and the baseline. There is also a slight drift downward in the signal with respect to scan unit. These effects are removed by baseline correction by flattening the signal and bringing the baseline offset to approximately zero RFU. (a) Before baseline correction. (b) After baseline correction.
Figure 3B:

Frequently, the baseline drifts slowly with time over the course of each electrophoretic run for the electropherogram. In this case, the data should be adjusted to remove this effect. The expert system implements a windowing median filter to smooth this baseline. This median filter uses a sliding window that is significantly larger in size (in scan units) than the typical number of points in a peak. The points in this window are sorted, and a reference point is chosen that is below the median value. Since the window is larger than the peak size, peaks should not have an adverse effect on the reference points chosen. The reference point for each window is subtracted from the signal's value at the corresponding time to provide a baseline corrected plot. FIG. 3 shows electropherogram data before (a) and after (b) baseline correction. It can be observed that the baseline is shifted from approximately 600 to 0, removing the influence the baseline would otherwise have on the heights of the peaks. This step should be performed subsequent to color separation for ABI 310 acquired data because the color separation matrices are valid only for uncorrected data.

Allele peak parameters can be assessed from raw DNA data. Allele peak parameters include allele peak height, position, width, skewness or symmetry, and general shape or morphology. Other allele peak parameters that can be assessed from raw peak data are also considered and will be known by those of skill in the art.

Allele peaks may be ideal or non-ideal. Examples of non-ideal peaks include noise peaks, narrow peaks, saturated peaks, asymmetric peaks, dual peaks, and hybrid peaks.

While the invention has been described as useful for analyzing allele peak data it would be understood by one of skill in the art that the methods and apparatus described herein can be used to analyze any two-dimensional data which exhibits peaks.

Figure 51:
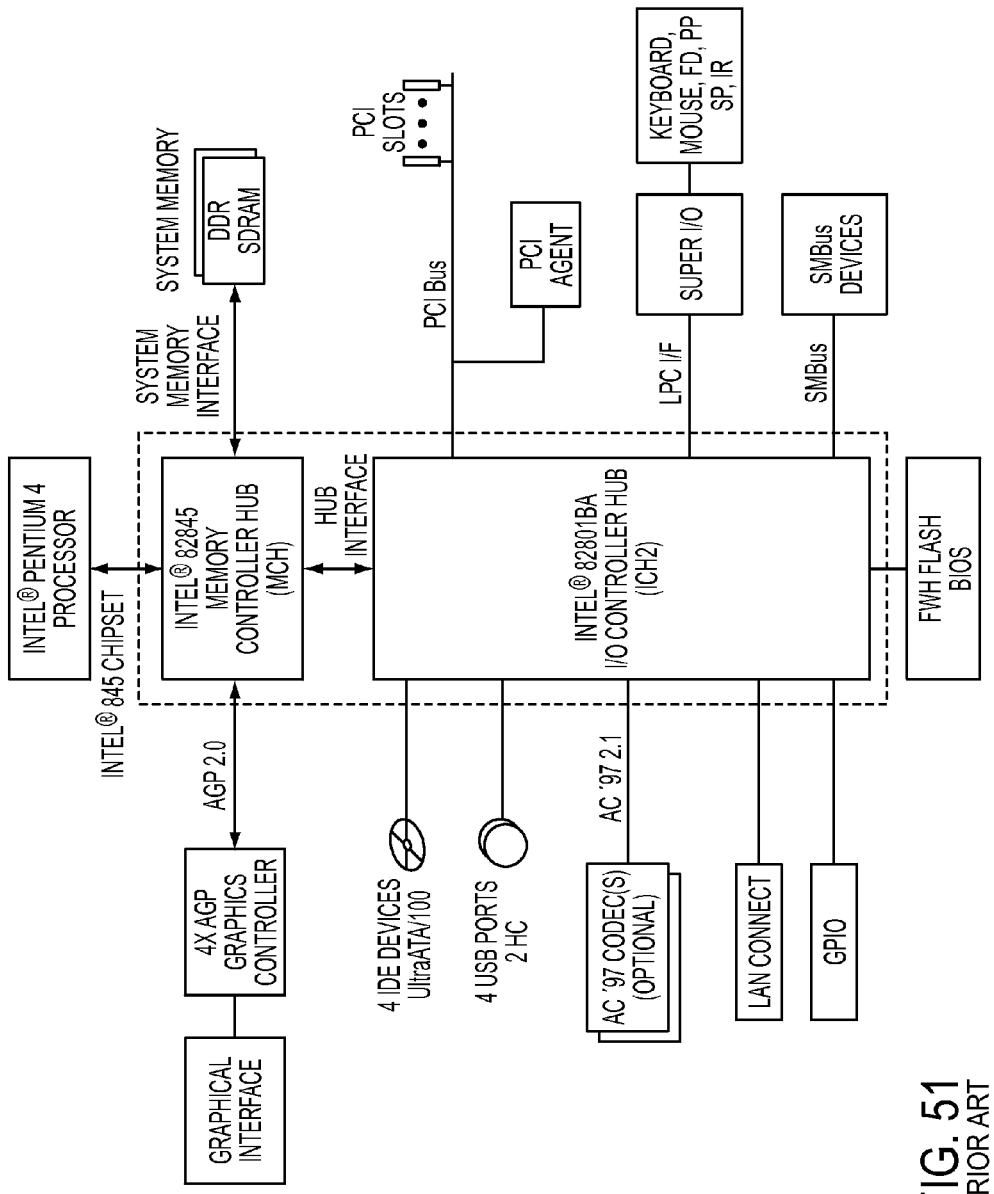
FIG. 51: PRIOR ART Pentium® 4 personal computer block diagram.

Analysis of allele peak data or other two-dimensional data may be performed using an apparatus. An apparatus may be, for example, a personal computer. An example of a personal computer that may be used to implement these analyses is a Pentium 4, 3 GHz class personal computer, for example, a "mainstream desktop" according to prior art FIG. 51, taken from FIG. 1, page 24, of a Feb. 2002, Intel design guide entitled: "Intel® Pentium® 4 Processor in 478-Pin Package and Intel® 845 Chipset Platform for DDR." Such a computer is capable of an average analysis through-put of approximately 500 samples per minute. Per FIG. 51, there are shown the Intel Pentium 4 Processor, a Graphics Controller for a graphical interface as described herein, an 845 Chipset, 4 USB ports, a PCI bus, a keyboard, a mouse, a LAN Connect communications interface and other well known Pentium 4 personal computer components circa 2002.

All patents and patent applications cited in this disclosure are expressly incorporated herein by reference. The above disclosure generally describes the present invention. A more complete understanding can be obtained by reference to the following specific examples which are provided for purposes of illustration only and are not intended to limit the scope of the invention.

EXAMPLE 1

Formulation of the Peak Fitting Problem

This example describes a formulation of the allele peak fitting problem. It provides a discussion on the measurement data that the peak fitter uses, presenting the ideal and non-ideal types of peaks that are to be encountered. The solution starts with a default fit by a Gaussian equation model whose parameters are arrived at by optimization. The optimization method and equation models that will be used are presented and limitations of the Gaussian model are described. If the default fit is deemed unacceptable, advanced models are sequentially evoked to provide a better fit. The development of criteria for triggering advanced fits and accepting results will be discussed.

EXAMPLE 1A

Allele Peak Detection and Fitting

The goal of peak detection is to identify a potential peak and return a window of sufficient width in scan units to contain the entire peak. This window can then be used by the peak fitter to fit the peak data by a selected model equation and return the peak attributes. A simple description of how the peak detector works is first described.

The peak detector is a complex state machine that iterates through raw DNA data, e.g., electropherogram data, looking for peaks. It utilizes a small window to track increases and decreases in area and height of data points and detect where potential peaks are present. The window uses thresholds to determine sufficient height and area measurements to trigger a peak detection event. When the area and height thresholds are exceeded, the peak detector records the current scan unit value as the start of a new peak window. It then iterates across the data until the area and height values corresponding to a subsequent scan unit value go below specified thresholds. This scan unit value is set as the end of the peak window. The start and end values are then extended by up to two scan unit points to the left and right, respectively, if their corresponding RFU data are monotonically decreasing. These new start and end points, in scan units, demarcate the window boundary for this peak, and the data points within this window are then sent to the peak fitter for fitting.

Figure 5:
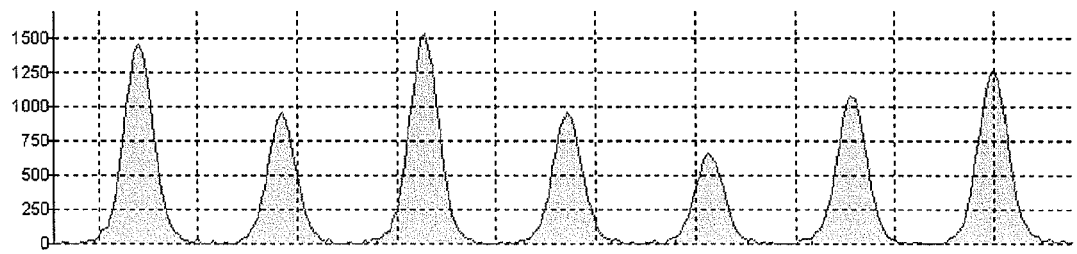
FIG. 5: Ideal Gaussian-shaped peaks. The majority of data will be of this smooth and symmetric shape.

A peak detection window corresponds to the shaded region under each peak in FIG. 5, which contains an array of the most commonly occurring peak type and shape in the data. In this figure, the peak outline is formed by connecting the dots between the peak data points. Ideal peaks like these are monotonically increasing or decreasing from the peak maximum and symmetric, with a shape similar to a Gaussian curve. The majority of data will be of this smooth and symmetric shape. The majority of the detected peaks are of this type, but a significant number of the peaks that will be described deviate from the ideal peak type. These less ideal peaks can be grouped into two categories: non-ideal peaks due to the inherent condition of the raw data and non-ideal peaks due to the characteristics of the data.

Figure 6:
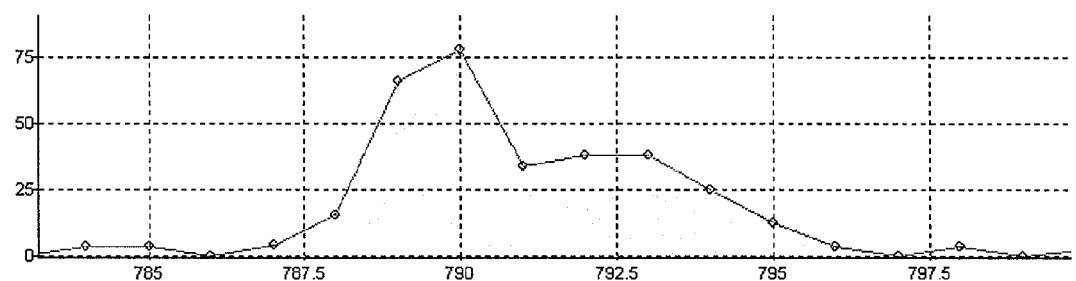
FIG. 6: An example of a low amplitude peak with noise. The peak shape is highly distorted by the noise threshold.
Figure 7:
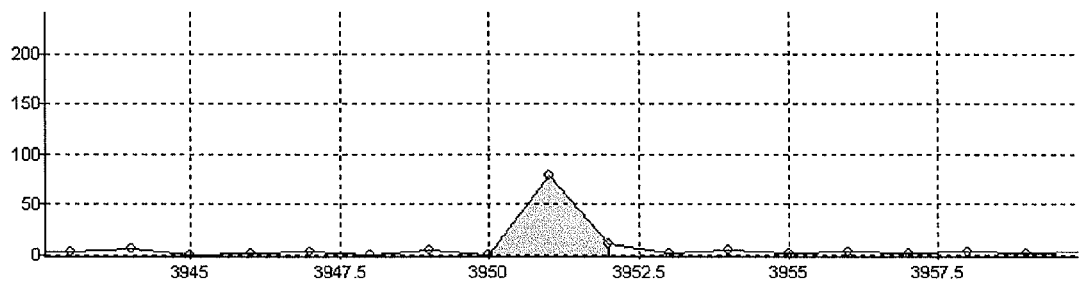
FIG. 7: An example of a narrow peak. The detection window contains only three points providing very little peak data.
Figure 8:
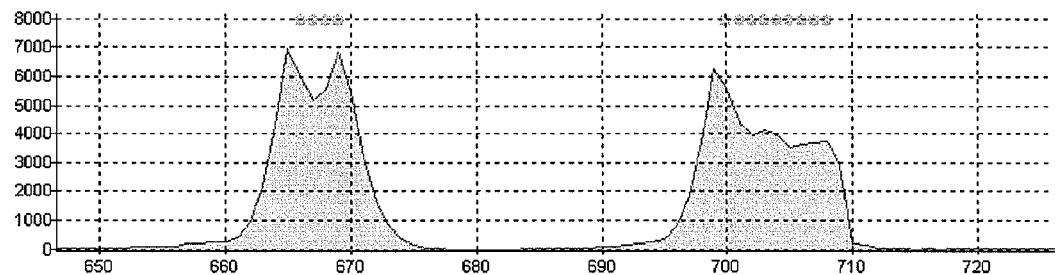
FIG. 8: An example of saturated peak data. The circles above the peak indicate saturated points before color separation.

Non-ideal peaks due to the inherent condition of the data are caused by an unexpected or undesired problem with the data, such as distortion by noise and saturation of data due to overloading of the sample. A sample noise peak as shown in FIG. 6 would be difficult to properly fit to an ideal peak shape because the noise may alter the shape or mask small amplitude peaks. Note the relatively low amplitude and narrow span of the noise peak. A normal peak has a typical span of 10-20 scan units. Peaks as in FIG. 7 that are narrow and contain only a few data points may also cause problems for fitting. This type of data appears to be a result of random, low amplitude noise that barely meets peak detection thresholds. On the other hand, saturated data from overloading of the DNA sample have wildly incorrect values after color separation at the previously saturated values (before color separation), resulting in a distorted peak shape, such as those shown in FIG. 8.

Figure 9:
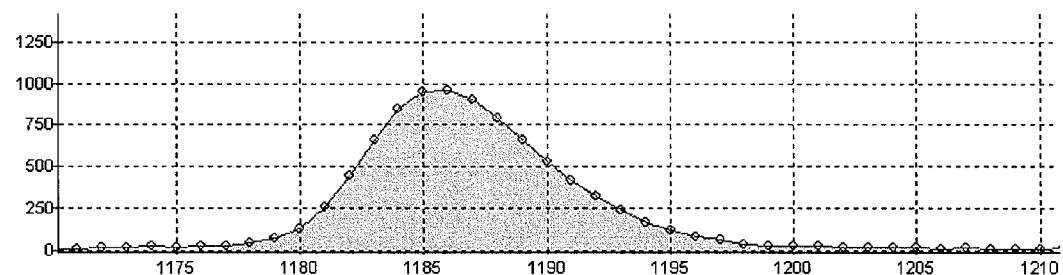
FIG. 9: An example of a highly skewed peak with pronounced tailing on the right side.
Figure 10:
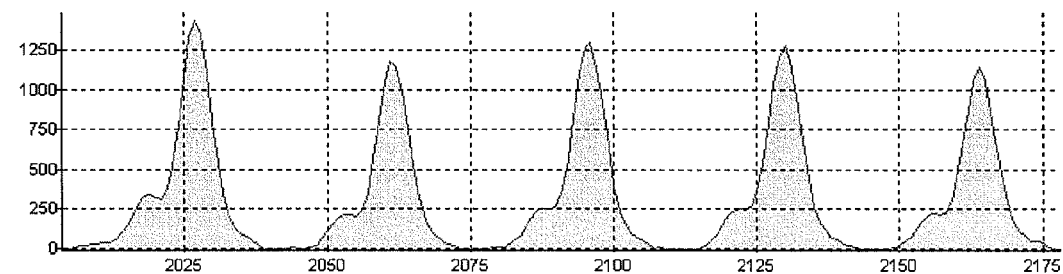
FIG. 10: An example of −A/+A peak data. The lower left shoulder is the −A form of the DNA fragment; the larger normal peak is the +A form. The peak window contains both peaks.
Figure 11:
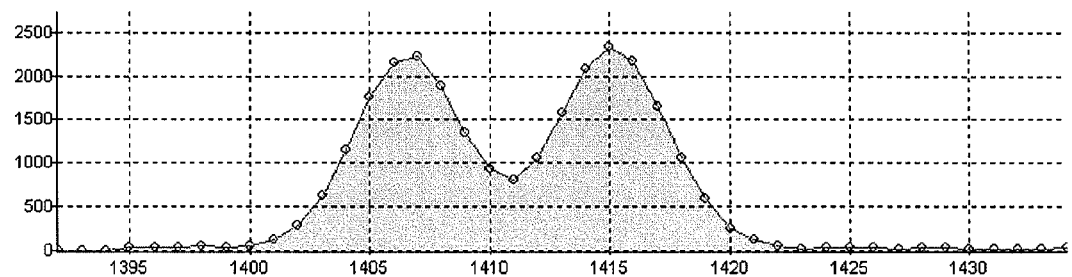
FIG. 11: An example of the 9.3/10 alleles of the TH01 locus contained in a single detection window; the two alleles overlap and are separated in size by 1 base pair.

Non-ideal peaks due to data characteristics arise from the electrophoretic process itself resulting in different peak shapes. Peak tailing results in peak asymmetry as shown in FIG. 9. This type of peak may have fronting or tailing, skewed to the left or right of the maximum, respectively. A second type of problem peak type is closely-spaced peaks separated by only one base pair, as in −A/+A peaks and the 9.3-10 alleles of the TH01 locus. These peaks can be detected in a single window containing both peaks and will be referred to as dual peaks. The −A/+A condition, as shown in FIG. 10, occurs when an extra nucleotide, adenine, is added at the ending base, resulting in the sequence being one base pair longer than it should be. This does not represent the presence of two alleles, but rather a mixture of PCR products, where some contain the extra nucleotide (+A) and others do not (−A). Butler states that commercially available STR kits promote the formation of the +A form so that ladders and samples will be consistent [9]. This implies that the +A peak should be considered the real allele and the −A peak should not be considered as part of the real allele, but the peak fitting method still needs to accommodate the −A leading shoulder. Another commonly occurring pair of closely spaced peaks exists: the 9.3 and 10 alleles of the TH01 locus, which are separated by one base pair and overlap, are shown in FIG. 11. These dual peaks need to be identified and fitted as two separate peaks. Accurate fitting of this type of dual peak is very important so as to give the appropriate respective peak center positions and heights.

EXAMPLE 1B

Solution Approach

The peak fitting problem may be formulated as a least squares error optimization problem. A peak model, which is a parameterized mathematical equation that predicts the measured signal intensity (RFU) as a function of the scan unit position, is postulated and tried. For any combination of specific values of the model's parameters, an error function can be defined as one-half of the sum of the squared differences (error) between the given measurement data and the predicted measurements calculated from the model at the array of scan unit values within the peak window. An optimization method is used to arrive at the optimal parameter values that minimize the error function. Many peak model families can be considered. The final choice of the model depends upon the required accuracy and computational efficiency. Once finalized and implemented, the optimization method becomes the main workhorse (the most important and computationally intensive element) of the fitter and should not be modified. The peak model, on the other hand, is intended to be easily replaced as required by the characteristics of the peak data at hand.

Gaussian Peak Model

Since the majority of the peaks appear to be symmetrical and approximately Gaussian in shape, the suitability and limitations of the Gaussian model are first investigated. The Gaussian peak model is described by a mathematical function $f(\chi_i, p)$, where $\{\chi_i\}_{i=1}^n$ is the array of positions in scan units where measurement data exist, n is the number of points in the data window, p is a vector in $\Re^m$ (with m components) of model parameters, and the function value $f(\chi_i, p)$ is the predicted measurement in RFU of the dye signal at the scan unit value $\chi_i$, evaluated using parameter vector p. For different values of the parameters contained in p, different peak shapes and heights are obtained, and the objective is to find a vector of parameters p in $\Re^3$ that produces a peak shape that most closely matches the given peak data in each data window.

The form of the Gaussian function is $$f(x, p) = Ae^{-(\frac{x-x_c}{\sigma})^2}, \qquad (4.1)$$

with $$p = [A, x_c, \sigma],$$

where A is the peak maximum height, $\chi_c$, the peak center location, and $\sigma$, a width measure.

Figure 12A:
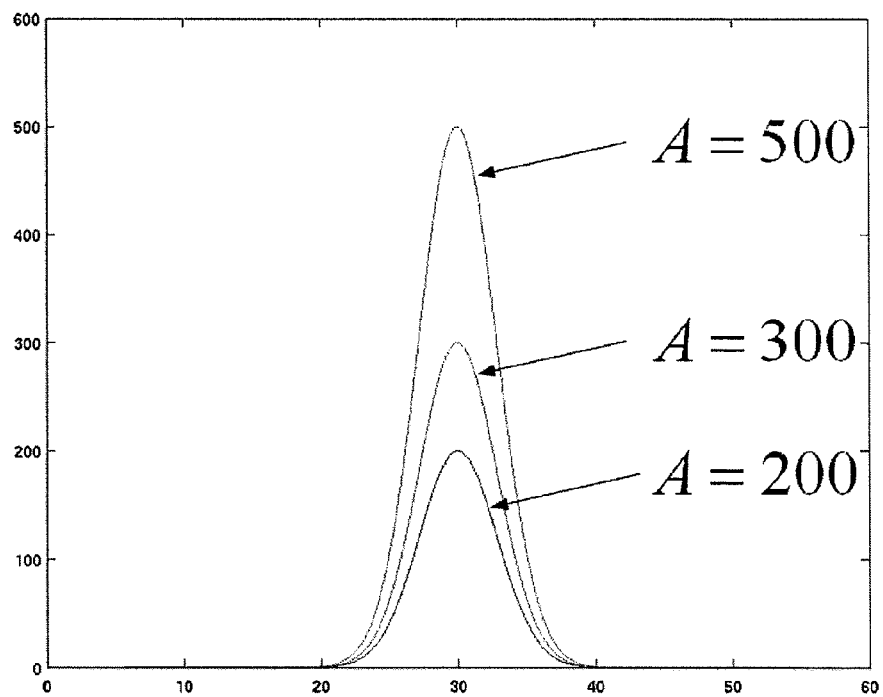
FIG. 12: Sample Gaussian curves with varying parameter values, showing the effect of each on the peak shape. (a) Varying A, keeping $\sigma=4$ and $x_c=30$; (b) varying $\sigma$, keeping $A=500$ and $x_c=30$; and (c) varying A and $\sigma$, keeping $x_c=30$.
Figure 12B:
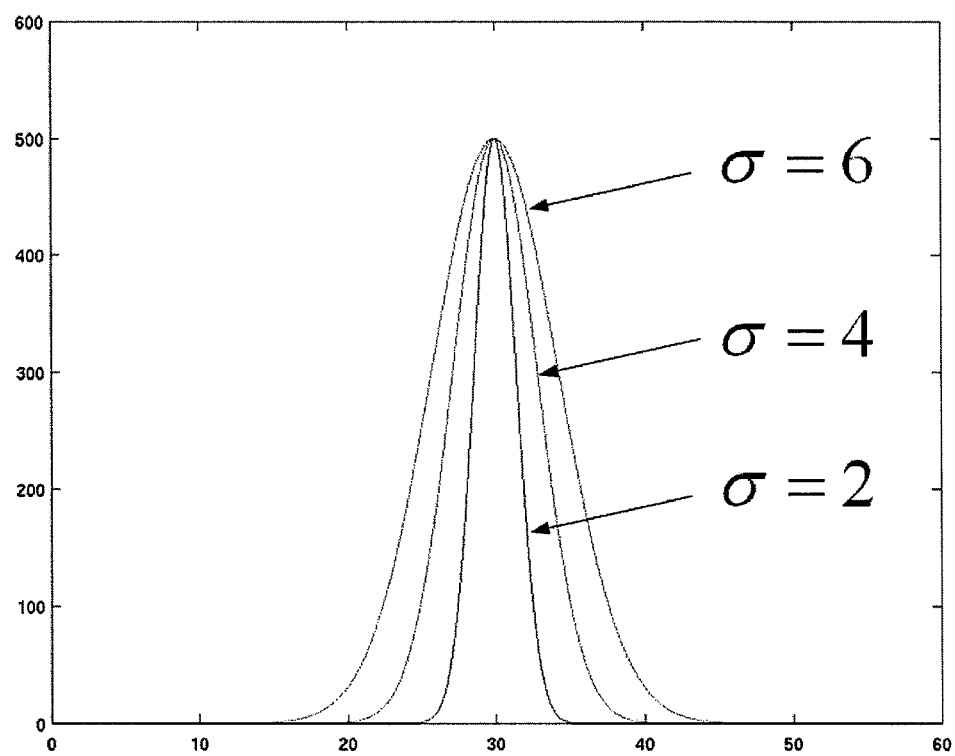
Figure 12C:
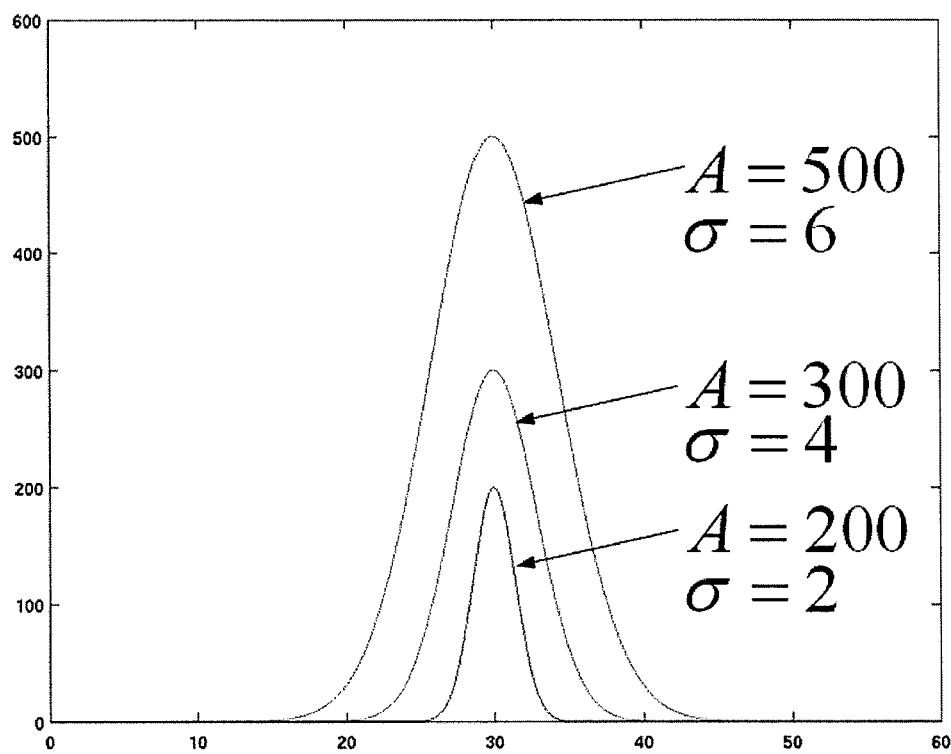
Figure 13:
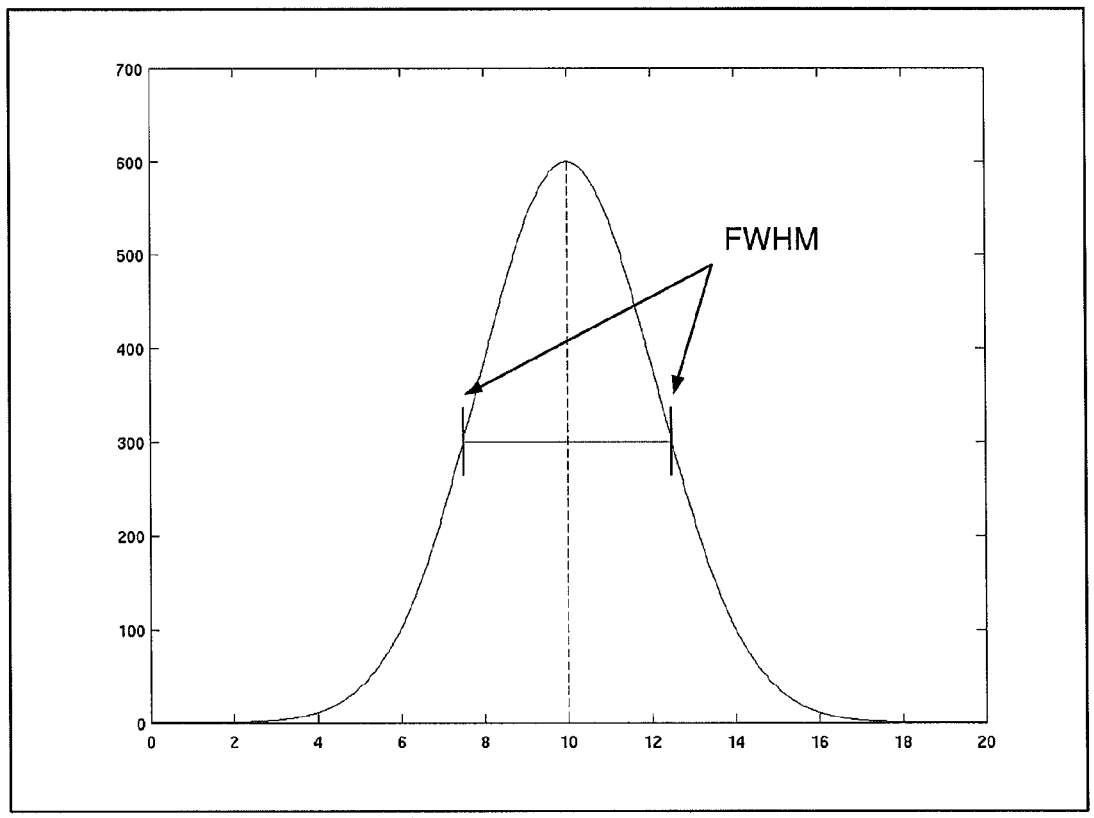
FIG. 13: Sample full width half max (FWHM) measurement for a Gaussian curve. The width measures the distance in the x-axis between the left and right sides of the curve at half of the curve maximum.

FIG. 12 illustrates an array of Gaussian curves with varying sets of parameter values to show the effect of the parameters on the resulting appearance of the peak. It is seen that the Gaussian function is symmetric about the point of maximum amplitude A, occurring at $\chi_c$. Therefore $\chi_c$ gives the center of the fitted curve. The center value will be regarded as the peak's location. The $\sigma$ value is directly related to the width of the peak and will be used to calculate the full width half maximum (FWHM) measurement. The FWHM corresponds to the horizontal distance in the x-axis in scan units between the points to the left and right side of the peak maximum whose values are half of the maximum height. The FWHM is used as a representative width measure because it is a standard measurement that can be used to directly interpret the width of peaks in terms of scan units, as shown in FIG. 13. The value is easy to determine both visually and analytically and provides a parameter that can be used directly by the expert system for determining if peaks are too narrow or broad. This value will be derived for all subsequent fits by different model equations and can be derived by setting the fit equation equal to $$\frac{1}{2}A,$$

solving for the two values of x, and finding the difference between them.

For the Gaussian model, the FWHM is $2\sigma\sqrt{\ln 2}$, a constant multiple of $\sigma$. The area under the Gaussian curve (from $-\infty$ to $\infty$) is $A\sigma\sqrt{\pi}$, which can be useful in fits where the given electropherogram data can not be directly used to calculate the area, if the area is desired to be known. Table 4.1 summarizes the Gaussian model equation.

TABLE 4.1

Summary table for Gaussian peak model equation.

| Fit model | Gaussian |
|---|---|
| Fit equation | $f(x, p) = Ae^{-(\frac{x-x_c}{\sigma})^2}$ |
| Optimization parameters | $A, x_c, \sigma$ |
| FWHM measure | $2\sigma\sqrt{\ln 2}$ |

Gauss-Newton Optimization Method

The least squared error optimization needed to fit the peaks may be solved by an unconstrained optimization procedure. Unconstrained optimization can find the same fit as that found by constrained optimization if the constrained optimal value is not on a constraint boundary. However, it is possible that the unconstrained optimal solution may not be feasible, and the resulting optimal parameters will be unrealistic for the given data or physically impossible in this case. The advantage of the unconstrained approach is that the optimization method is mathematically simpler and computationally more efficient, but the results must be verified by checking for feasibility.

In optimization problems of this type, the goal is to minimize a cost function J, which in this case is one-half of the total sum of squares of the errors between the fitted function, $f(\chi_i, p)$, and the given RFU peak data, $\{y_i\}$, where $y_i$ denotes the measurement data at the $\chi_i$ value. Given points $\{(\chi_i, y_i)\}_{i=1}^n$ to be fitted by an equation with parameter vector p∈z,67 $^m$, the cost function is defined as $$J(p) = \frac{1}{2}\sum_{i=1}^{n}(y_i - f(x_i, p))^2, \quad (4.2)$$

and the goal is to find p* such that $$J(p^*) \leq J(p) \forall p \in \mathbb{R}^m.$$

To find the parameter vector p* that minimizes the cost, the Gauss-Newton method is chosen to search for an optimum solution [8]. The vector function g(p) representing the individual fitting errors in each of its components is formed to simplify notation. Let $$g(p) = \begin{bmatrix} y_1 - f(x_1, p) \\ y_2 - f(x_2, p) \\ \vdots \\ y_n - f(x_n, p) \end{bmatrix},$$

then the objective is to $$\min J(p) = \min\frac{1}{2}\sum_{i=1}^{n}(y_i - f(x_i, p))^2$$

$$= \min\frac{1}{2}\|g(p)\|^2,$$

where $$\|g(p)\| = [g(p)_1^2 + \ldots + g(p)_n^2]^{\frac{1}{2}}.$$

The parameter vector p is updated iteratively from an initial guess using the relation $$p_{k+1} = p_k - \alpha_k[\nabla g(p_k)\nabla g(p_k)^T]^+\nabla g(p_k)g(p_k),$$

where k indicates the iteration number and '∇' denotes the gradient operator. ∇g(p) and $$\frac{\partial g(p)}{\partial p_i}$$

are calculated from the partial derivatives of f and g:

$$\nabla g(p) = \begin{bmatrix} \frac{\partial g(p)^T}{\partial p_1} \\ \frac{\partial g(p)^T}{\partial p_2} \\ \vdots \\ \frac{\partial g(p)^T}{\partial p_m} \end{bmatrix}$$

and

-continued $$\frac{\partial g(p)}{\partial p_i} = \begin{bmatrix} -\frac{\partial f}{\partial p_i}(x_1, p) \\ -\frac{\partial f}{\partial p_i}(x_2, p) \\ \vdots \\ -\frac{\partial f}{\partial p_i}(x_n, p) \end{bmatrix}.$$

The direction of descent is defined by $-[\nabla g(p_k)\nabla g(p_k)^T]^+ \nabla g(p_k)g(p_k)$, and the stepsize is determined by $\alpha_k$ where $\alpha_k \geq 0$. The '[...]⁺' operator in this expression represents the matrix pseudoinverse. The algorithm stops when the change in the sum of squared fitting error, Δ,l, between successive iterations is sufficiently small or a specified maximum number of iterations is reached.

For this application, the stepsize $\alpha_k$ will be chosen using the Armijo rule [8]. The advantage to this rule over other methods, such as various line minimizations, is that it tends to be less computationally intensive. The parameter update is then defined by $$p_{k+1} = p_k + \beta^{m_k}sd_k, \quad (4.4)$$

such that $m_k$ is the smallest nonnegative integer that satisfies $$J(p_k) - J(p_k + \beta^{m_k}sd_k) \geq -\sigma\beta^{m_k}s\nabla J(p_k)^T d_k, \quad (4.5)$$

where $$d_k = -[\nabla g(p_k)\nabla g(p_k)^T]^+\nabla g(p_k)g(p_k) \quad (4.6)$$

and $$\nabla J = \nabla g(p)g(p). \quad (4.7)$$

Here β, s, and σ are appropriately chosen scalars. Inequality 4.5 guarantees that the cost is improved with each iteration by a certain factor determined by the selectable scalars and $m_k$. When Inequality 4.5 is satisfied, $\beta^{m_k}sd_k$ is the term added to update the current optimal parameter vector. In the Armijo rule, $\beta^{m_k}s$ is the stepsize $\alpha_k$ that was described previously in Equation 4.3.

EXAMPLE 1C

Limitations of the Gaussian Peak Model

The Gaussian peak model described in the previous sections can accurately fit ideal peak data, but falls short to properly fit the non-ideal peak types. A set of figures is presented below that show non-ideal peak types fitted with a Gaussian peak model equation.

Figure 14:
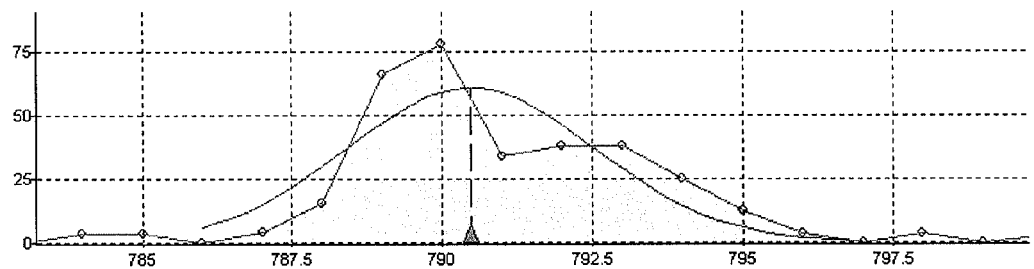
FIG. 14: An example of a low amplitude peak distorted by noise. The peak shape is highly distorted by the presence of noise and the fit does not accurately model the peak. It is uncertain where the peak center is.
Figure 15:
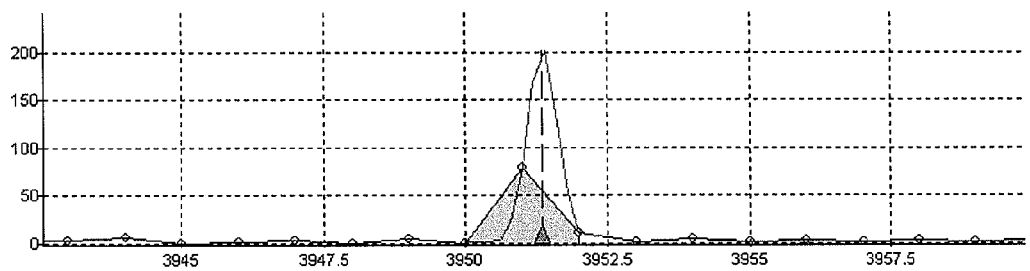
FIG. 15: Gaussian fit of a narrow peak. The fit has the minimum fitting error but does not describe the shape of the peak properly.
Figure 16:
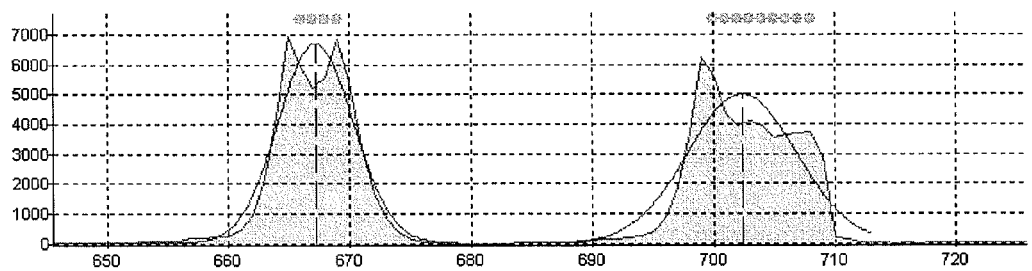
FIG. 16: Gaussian fits of two saturated peaks. The fits show that the saturated points in the peaks should not be used when a fit is attempted; it gives a peak maximum that is much lower than it should be based on the data points outside the saturated window.

Noise peaks, narrow peaks, and saturated peaks can nominally be fitted by the Gaussian model, but the data will require special treatment. FIG. 14 shows a noise peak fitted with a Gaussian curve. Because of the distortion of the raw peak shape, the Gaussian curve is unable to accurately calculate the position of the apparent height of the peak. A similar situation is the narrow peak shown in FIG. 15. Although the Gaussian curve displayed is the fit that yields the minimum error, the resultant curve does not give a good fit. The Gaussian equation can sufficiently model these peaks to obtain their center and height, but the method for finding the suitable model parameters needs to be adjusted, or preprocessing of the data needs to be performed. Narrow peaks can be directly assigned Gaussian model parameters (non-optimum) to ensure that the apparent maximum height and position in the window correspond to the fitted height in RFU and center position in scan units. Saturated points, being lower in height than the heights they would have attained had the saturation not occurred, cause the fitted maximum amplitude A to be lower than it should be as predicted from those unsaturated points lying outside the region of saturation in the window, as shown in FIG. 16. By excluding the saturated points from the fit, the Gaussian model can then be used to better fit the saturated peak.

Figure 17:
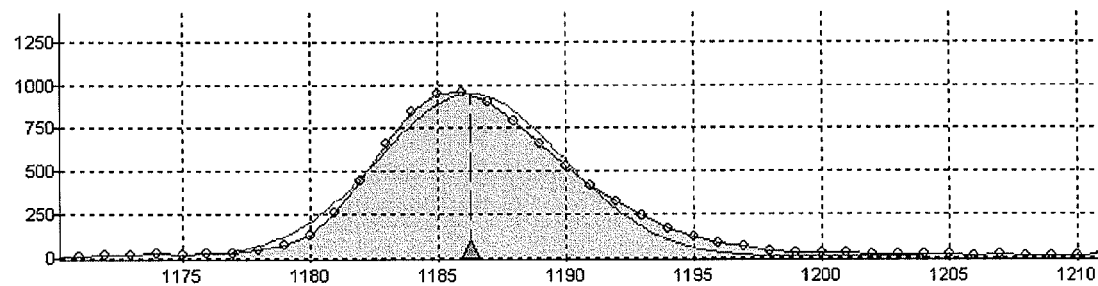
FIG. 17: Gaussian fit of a highly skewed peak. The fit is unable to model the apparent height and center due to the degree of asymmetry.

Highly asymmetric peaks and dual peaks are unsuitable for fitting by the Gaussian model equation if a high precision of the location and height of the peak maximum or resolution of multiple peaks is desired. The greater the skewness of the peak, the less accurate the parameters of the symmetric Gaussian model are in describing the peak location and height. FIG. 17 shows a skewed peak with a Gaussian fit where forced fitting by a Gaussian model leads to misaligned peak center positions (the point of maximum peak height).

Figure 18:
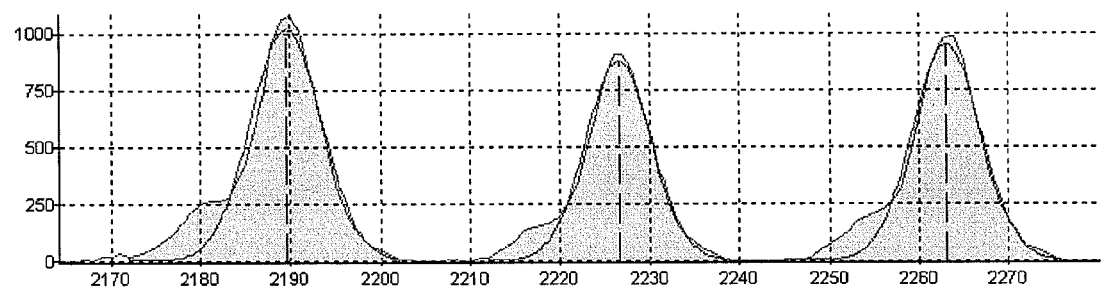
FIG. 18: Gaussian fits of −A/+A peaks. Although the −A peak does not need to be resolved if the +A peak can be accurately fitted, this example shows that a substantial −A contribution will cause a Gaussian model to be unable to find the apparent height and center of the +A peak.
Figure 19:
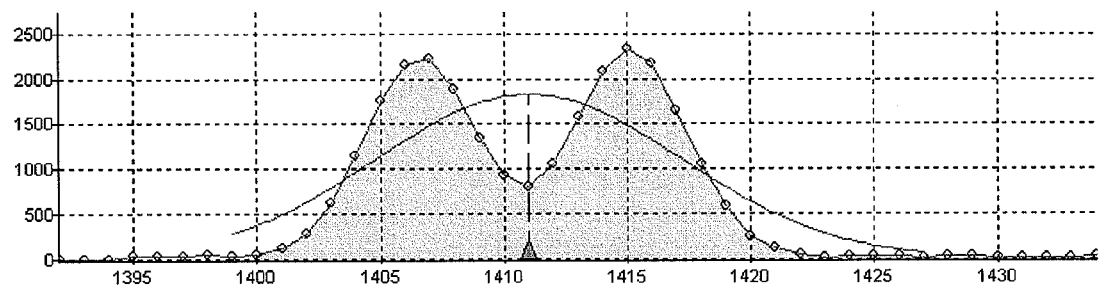
FIG. 19: Gaussian fit of 9.3/10 alleles of TH01 locus. The inability to resolve this window into peaks using the simple Gaussian indicates the need for a more advanced fit model.

Resolving two closely spaced peaks in a single detection window is another situation where the Gaussian model does not fit well. Two types of dual peaks need to be considered. The first is the −A/+A peaks with the −A peak appearing as a leading left shoulder preceding the main +A peak, as those shown in FIG. 18. It is the +A peak that corresponds to a true allele; the −A peak needs to be recognized as a superfluous peak, and it should be fitted as an independent peak so that its presence does not contribute to the fit of the +A peak. The second dual peak type is the alleles 9.3/10 pair of TH01, separated by only one base pair. These two alleles need to be recognized as two peaks and be fitted independently from each other, complete with their own peak center positions, maximum heights, and widths. Fitting by a simple Gaussian equation gives a completely erroneous picture, as that shown in FIG. 19.

It is clear that more advanced model equations need to be introduced to accommodate these types of non-ideal peaks. Example 1D presents the advanced models selected to fit these types of peaks and gives the mathematical properties of each.

EXAMPLE 1D

Advanced Equations

The majority of peaks can be fitted well with a simple Gaussian model equation, but for some non-ideal peaks, modified Gaussian models need to be considered. The non-ideal cases that require a model other than the simple Gaussian are the asymmetric and dual peaks.

Asymmetric Peak Model

Figure 20:
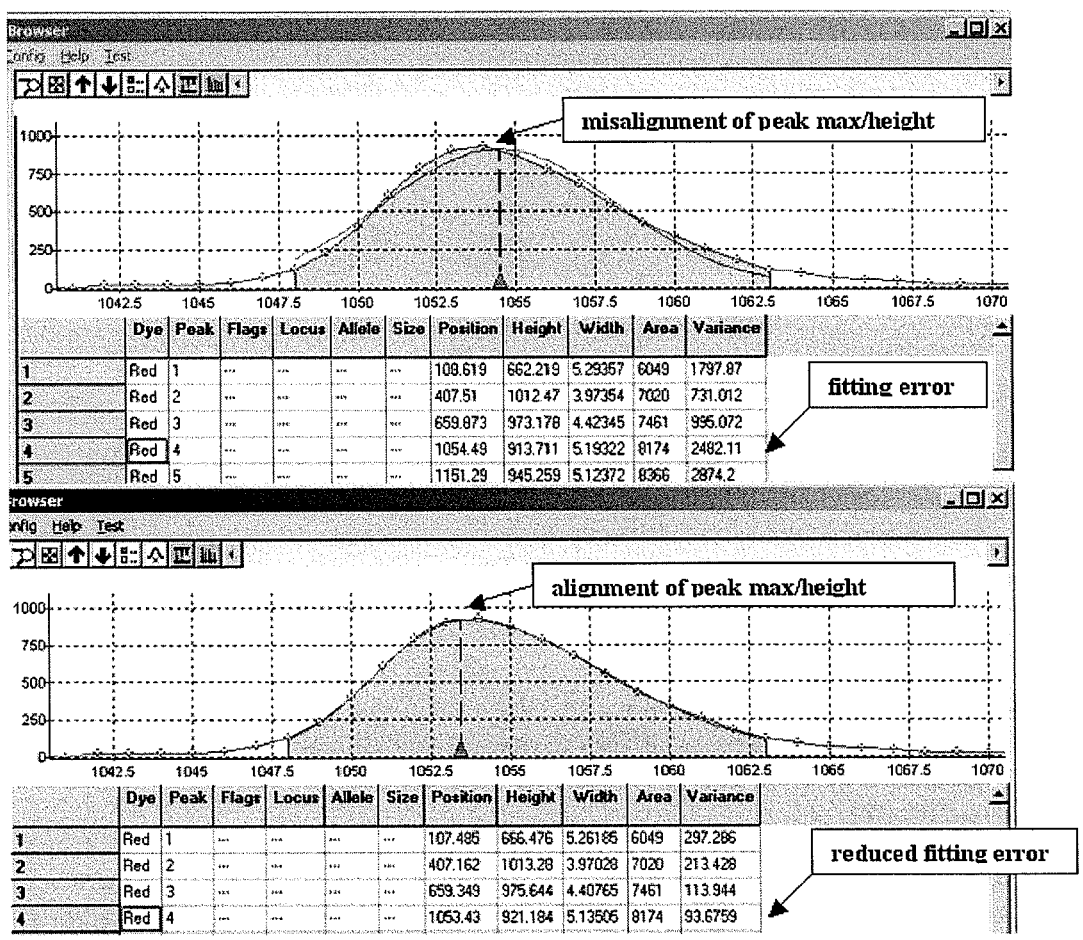
FIG. 20: Two-sided Gaussian applied to a skewed peak to reduce fitting error.

Asymmetry in a peak due to tailing or fronting requires the introduction of skewed models. To help reduce fitting error caused by the skewness, a two-sided Gaussian was initially tested in the C++ implementation. This model uses two Gaussian equations with different a parameter values to individually model the left and right half of the peak data. The two equations have the same peak height and center parameter values. FIG. 20 shows an example of the improvement using this model over that of the Gaussian fit. The misalignment of the peak center and fitting error are greatly reduced. Also note that the fitted peak positions differ by approximately 1 scan unit, which may be significant and lead to an erroneous allele call of this peak. Unfortunately, this equation tended to be numerically unstable in certain situations, so other asymmetric models were investigated.

Figure 21A:
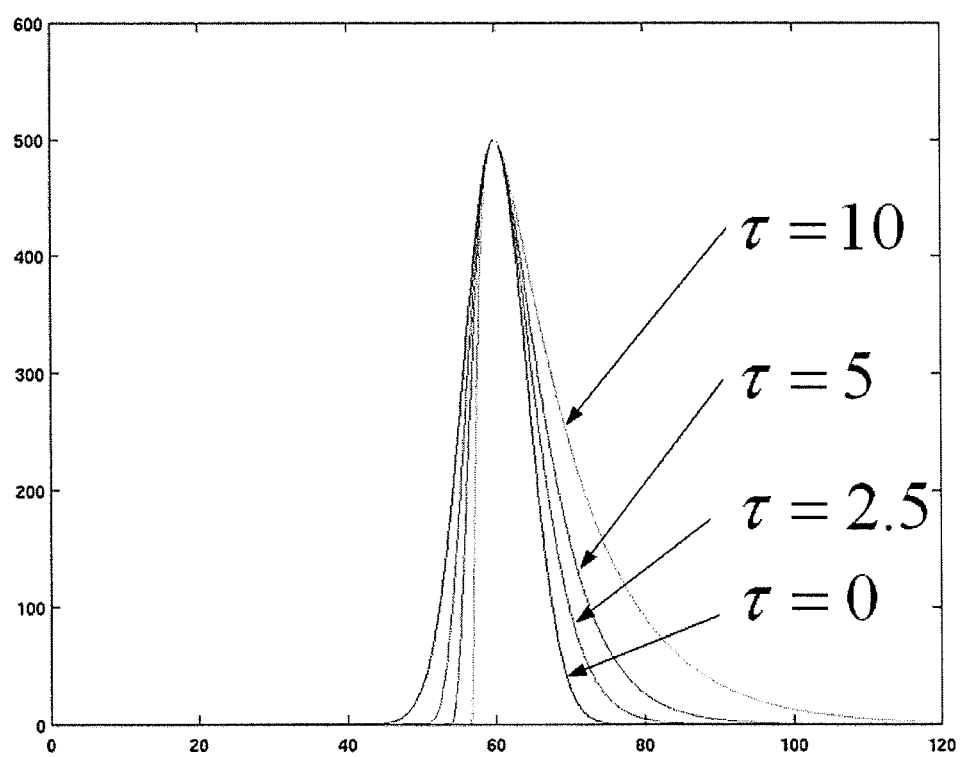
FIG. 21: Example Hybrid curves that show how the change in the skewness parameter affects the shape. (a) $\tau$ adjusted positively (tailing); $A=500$, $\sigma=6$, and $x_c=60$. (b) $\tau$ adjusted negatively (fronting); $A=500$, $\sigma=6$, and $x_c=60$.
Figure 21B:
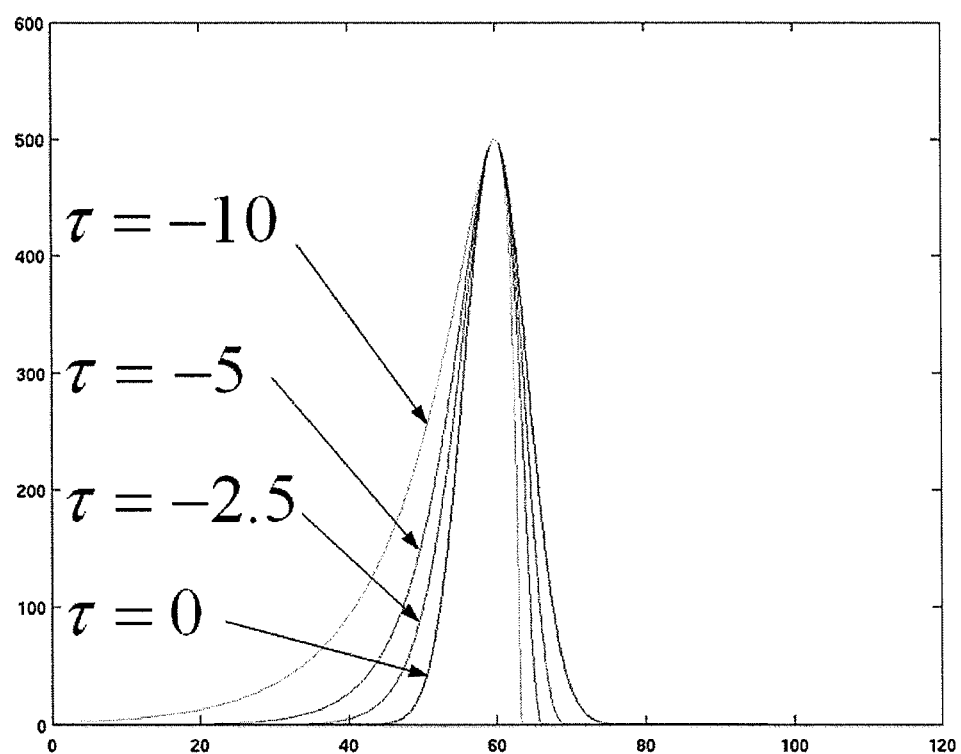

A relatively simple equation, using a Gaussian function with a modified exponential expression, has been found in the literature to be better in fitting skewed peaks [14]. It is often referred to as the exponential Gaussian hybrid function and will be called the Hybrid model in this text. This model is defined as $$f(x, p) = \begin{cases} Ae^{\left(-\frac{(x-x_c)^2}{\sigma^2+\tau(x-x_c)}\right)}, & \sigma^2 + \tau(x - x_c) > 0; \\ 0, & \sigma^2 + \tau(x - x_c) \leq 0; \end{cases} \quad (4.8)$$

with $$p = [A, x_c, \sigma, \tau],$$

where A is the maximum peak height, $\chi_c$ is the peak center position, $\sigma$ is a width measure, and $\tau$ is the peak skewness parameter. The parameter $\tau$ indicates peak tailing if positive and peak fronting if negative. A $\tau$ value of zero, representing no skewness, makes the model equivalent to a pure Gaussian. The half width is not symmetric in skewed peaks, and the $\tau$ parameter in conjunction with the $\sigma$ must be used to calculate the FWHM. To make the shape equivalent to the Gaussian model used in this research when $\tau$ is zero, the equation is modified slightly from the literature (changing $2\sigma^2$ to $\sigma^2$) [14]. However, the trade-off is that this model adds a skewness measure to the parameter list, thereby increasing the computational burden. FIG. 21 shows the relationship of the skewness parameter to the shape of the peak. Table 4.2 gives a summary for the Hybrid model equation.

TABLE 4.2

Summary table for Hybrid peak model equation.

| | |
|---|---|
| Fit model | Exponential Gaussian Hybrid |
| Fit equation | $f(x, p) = \begin{cases} Ae^{\left(-\frac{(x-x_c)^2}{\sigma^2+\tau(x-x_c)}\right)}, & \sigma^2 + \tau(x - x_c) > 0 \\ 0, & \sigma^2 + \tau(x - x_c) \leq 0 \end{cases}$ |
| Optimization parameters | A, $x_c$, $\sigma$, $\tau$ |
| FWHM measure | $\sqrt{(\ln 2\tau)^2 + 4\ln 2\sigma^2}$ |

Dual Peak Model

Figure 22A:
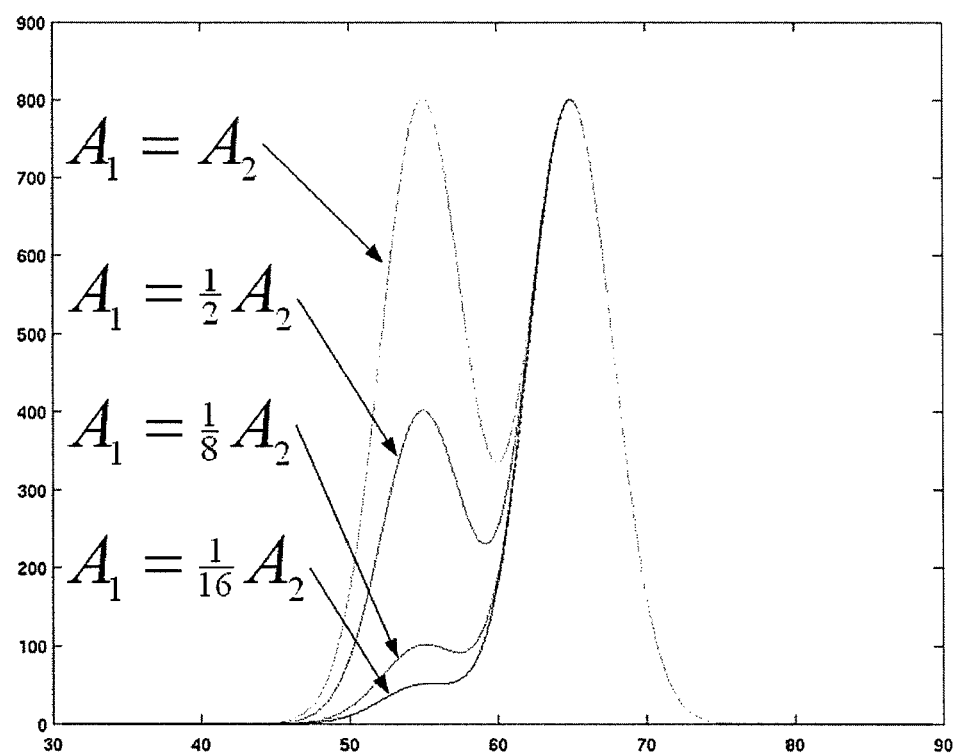
FIG. 22: Example dual peak curves as given by Equation 4.9 that show how the change in parameters affect the peak shape. (a) $A_1$ adjusted as a fraction of $A_2$ held at 800 with $\sigma_1=4$, $\sigma_2=4$, and $x_{c1}=55$, $x_{c2}=65$; (b) separation between $x_{c1}$, $x_{c2}$ adjusted, labeled as $\Delta x_c = x_{c2} - x_{c1}$, with $A_1=A_2=400$ and $\sigma 1=\sigma 2=4$.
Figure 22B:
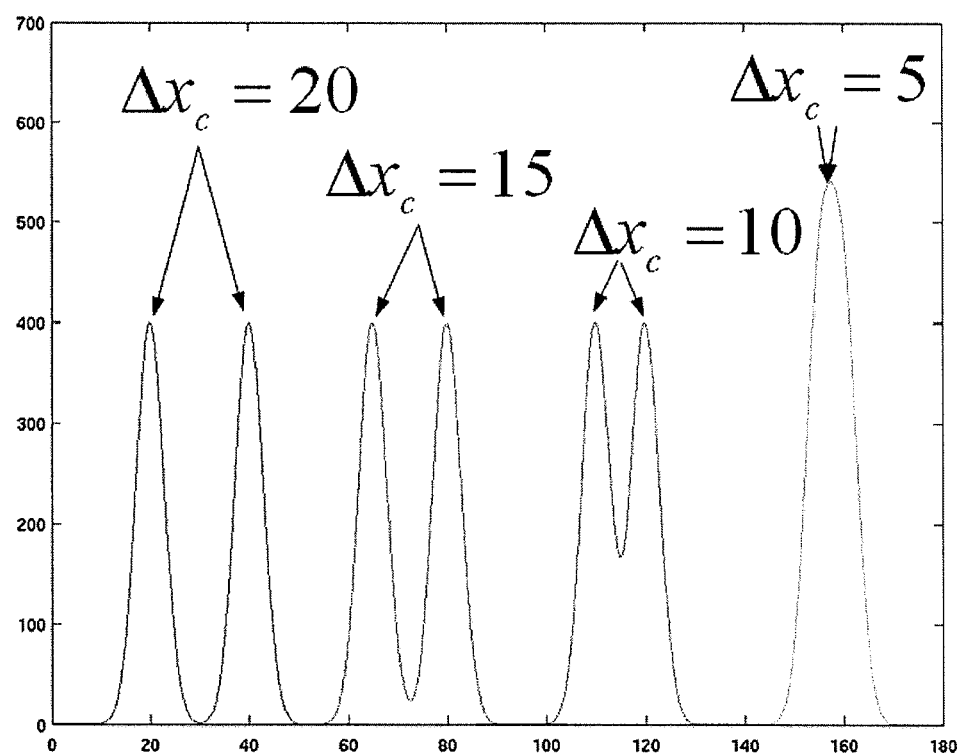

Two closely occurring peaks in the same detection window need to be resolved for −A/+A and TH01 9.3/10 peaks. This requires that one model have the ability to fit the data inside the window as two separate peaks, with peak parameter sets. The previous fit types only fit one peak per window. For dual peak fitting, a modified Gaussian equation with two terms is considered [23]. Each term represents a peak, which is superimposed onto the fit given by the other term. The two terms have independent center, width, and height parameters. The Dual peak model is presented below.

$$f(x, p) = A_1 e^{-\left(\frac{x-x_{c1}}{\sigma_1}\right)^2} + A_2 e^{-\left(\frac{x-x_{c2}}{\sigma_2}\right)^2}, \quad (4.9)$$

with $$p = [A_1, x_{c1}, \sigma_1, A_2, x_{c2}, \sigma_2],$$

where $A_1$ and $A_2$ are the peak maximum heights, $\chi_{c1}$ and $\chi_{c2}$ the peak centers, and $\sigma_1$ and $\sigma_2$ the width measures of the two peaks, respectively. Note that six parameters are required to model the peaks adequately using this approach. FIGS. 22 (a) and 22 (b) show the versatility of the model based on these parameters. The ability to model a shouldered peak as in −A/+A peaks is demonstrated in FIG. 22 (*a*) by adjusting the relative heights of the two peaks. Different degrees of overlap are demonstrated in FIG. 22 (*b*) by modifying the distance between the relative center position of the peaks. These sample overlap curves apply to the 9.3/10 alleles or other peaks that contain some degree of overlap. Note that at closest proximity shown ($\Delta_{xc}$=5), the Dual peak model begins to appear as a single Gaussian peak but with a broader overall FWHM width measure. Table 4.3 summarizes the Dual peak model.

TABLE 4.3

Summary table for Dual Gaussian peak model equation.

| Fit model | Dual Gaussian |
|---|---|
| Fit equation | $f(x, p) = A_1 e^{-\left(\frac{x-x_{c1}}{\sigma_1}\right)^2} + A_2 e^{-\left(\frac{x-x_{c2}}{\sigma_2}\right)^2}$ |
| Optimization parameters | $A_1, x_{c1}, \sigma_1, A_2, x_{c2}, \sigma_2$ |
| FWHM measures | $2\sqrt{\sigma_1^2 \ln 2}, 2\sqrt{\sigma_2^2 \ln 2}$ |

Trade-Off Between Model Complexity and Improvement of Fit

As described in the literature review, there are a multitude of equations that can be used to model peaks. Incorporation of additional parameters, however, increases the amount of computation required to find the optimal fit. The improvement in fit must outweigh the increase in computation to justify using a more complicated model. The use of multiple peak models is supported in the expert system by implementing multiple fit types that can be applied to any given peak window. Choosing which fit type to evoke for a given window of peak data is an important issue that requires analysis of the data and results from fits. Since all peaks processed by the expert system will first be fitted using the peak fitter, it is important to choose the fit that not only provides a suitable fit to allow for correct allele calls, but also minimizes the amount of required computation in order to increase the throughput of the DNA profiles interpreted by the expert system. A simple Gaussian fit will be more efficient than a fit using the Hybrid or the Dual model, but it may not be sufficient to yield an accurate set of peak parameters. The suitable fit type to accept should be automatically chosen by the peak fitter routine by applying criteria to trigger the evoking of the next fit type when the current fitting has been judged unsatisfactory. The next subsection will describe the need for developing criteria and the sequential flow of peak fitting by the various peak models.

EXAMPLE 1E

Need for Developing Criteria for Triggering Subsequent Fit Type and for Accepting Fit Results The fitting processes do not have the intelligence to determine what type of model is more appropriate to use for the given data; either the optimization step converges, or it does not. Different fits with a variety of peak model equations acting on the same set of data produce different outcomes. Interpretation of these results is necessary to assess if the fit returns parameters giving a suitable fit. This includes checking the validity of the parameters and calculating the error in the fit. Validity implies that the parameters are reasonable given the peak window and model type. Parameters that will cause the peak center position to fall outside the peak window should be discarded because detection windows should contain the peak maximum height and center position within its boundaries. Interpretation of error measurements is slightly more complicated and needs to be closely analyzed to be used effectively. The locations of data values that contribute significantly to fitting error with respect to peak location need to be identified in order to determine where the fit equation fails to model the data adequately, thereby evoking the next fitting model type.

Because the location and height resulting from a fit are the most important parameters for a peak, the peak window is split into a primary region and a secondary region. The primary region contains points near the peak maximum and above a certain threshold, at a fraction of the fitted peak height, while the secondary region contains all points below that threshold. The threshold is selected to encompass the points that, if closely fitted to the data, will provide an accurate position and maximum height for the peak.

The concept of an excursion as a measure of misfit will now be explained. An excursion refers to a deviation of the measurement data point from its fitted counterpart on the curve. Error envelopes, bounding the fit deviations between the measured data and fitted values will be developed to detect unacceptable excursions. The excursions will be divided into two classes: primary and secondary. The error envelope for the primary region will be tighter than the secondary region that flanks the central primary region. Excursions in these regions will be logged and used to identify where the fitting deviations are relatively large.

The mean squared error (MSE) of the peak fit will also be used as a measure of the quality of fit by a specific model. MSE refers to the average sum of squared error between the measurement data and the corresponding fitted data inside a selected window. Two different MSE measurements will be made: a MSE across the entire peak window and a primary MSE using just points inside the primary region. MSE gives an indication of how closely the fit is to the given measurement data and can be used to compare fits that use different peak model equations.

The fit quality assessment criteria utilize a heuristic approach to decide the subsequent fit type to trigger and ultimately to accept. Upon inspection of the data points in the peak detection window, certain peak fitting decisions are obvious, such as fitting peaks that have too few points or contain saturated data. These two non-ideal peaks require direct fit modes to accommodate the data. Development of criteria to trigger fits for other peak types such as for asymmetric (skewed) peaks or dual peaks are more complicated. In this situation, the criteria will involve sequentially attempting the different peak model equations (Gaussian, Hybrid, and Dual) in order of increasing complexity. As each fit model is used to fit the data, the excursions will be used to determine the quality of fit and whether the fit is accepted. If none of the three models is accepted, another set of decisions takes place. The fit model from the previously mentioned three models that resulted in the least value of MSE (assuming the parameters are valid and the optimization method converged for the model) is accepted. If none of the models attempted can be accepted using this condition, a direct fitting of the parameters is then performed. The specific fit types that will be used and a more detailed description of the flow are described in Example 2.

EXAMPLE 2

Development of Peak Fitter

This examples describes the development of the expert system peak fitter implementation.

EXAMPLE 2A

Initial Implementation of Peak Fitter

The peak fitter was developed in stages. First, a MATLAB [3] implementation was designed to check feasibility of fitting peaks using Gaussian-like model equations and to determine whether optimization techniques could be applied to fitting peak data. Once feasibility of the approach was established, a C++ implementation was written and embedded into the expert system program. This initial development focused on the basic peak fitting method described in Example 1.

Determination of Feasibility of Problem Using MATLAB

The built-in routines in the MATLAB Optimization Toolbox [5] were first used to test the feasibility of fitting peak data using the Gauss-Newton optimization method applied to several peak model equations. The 'lsqcurvefit' fitting function was used to identify the existence of a 'best fit' set of parameters for the peak models. This built-in function can be set by choosing the appropriate option to use the Gauss-Newton method.

Gaussian, Lorentzian, and Gaussian-Lorentzian peak models [17] were tested with respect to their ability to model ideal symmetric peaks. The latter two models have the ability to accommodate peaks with relatively higher fronting and tailing shoulder points.

The forms of these three equations are presented below. The Gaussian model is defined by the equation $$f(x, p) = A e^{-\left(\frac{x-x_c}{\sigma}\right)^2}, \quad (5.1)$$

with parameters p=[A,$x_c$,σ] defined below. The Lorentzian model is defined by the equation $$f(x, p) = \frac{A}{4\left(\frac{x-x_c}{\sigma}\right)^2 + 1}, \quad (5.2)$$

TABLE 5.1

Parameter summary table for Gaussian, Lorentzian, and Gussian-Lorentzian peak equation models used in MATLAB.

| | |
|---|---|
| A | Height of the peak |
| $x_c$ | Center position (location) of the peak |
| σ | Width measure for the peak |
| M | Fraction Lorentzian (Only applies to Gaussian-Lorentzian model) | with the same parameters p=[A,$x_c$,σ]. The Guassian-Lorentzian model is defined by the equation $$f(x, p) = (1-M)A e^{-\left(\frac{x-x_c}{\sigma}\right)^2} + M \frac{A}{4\left(\frac{x-x_c}{\sigma}\right)^2 + 1}, \quad (5.3)$$

with parameters p=[A,$x_c$,σ,M], where 0≤M≤1 is a parameter that determines the relative weight given to the Lorentzian component of the model. The parameters for these equations are given in Table 5.1

In this test setup, the data used were obtained from raw ABI 310 data containing a large number of symmetric peaks given as RFU as a function of scan unit. Raw data were color separated, baseline corrected, and detected into data windows before fitting by the peak models. Static windows of 20 points were taken around detected peaks. The optimal parameters for each equation were found using the 'lsqcurvefit' MATLAB optimization function, which requires a fit equation model, an initial parameter vector guess, the scan unit values, and the RFU values of the points in a data window. The results obtained from each of the three equation models were then compared.

Figure 23:
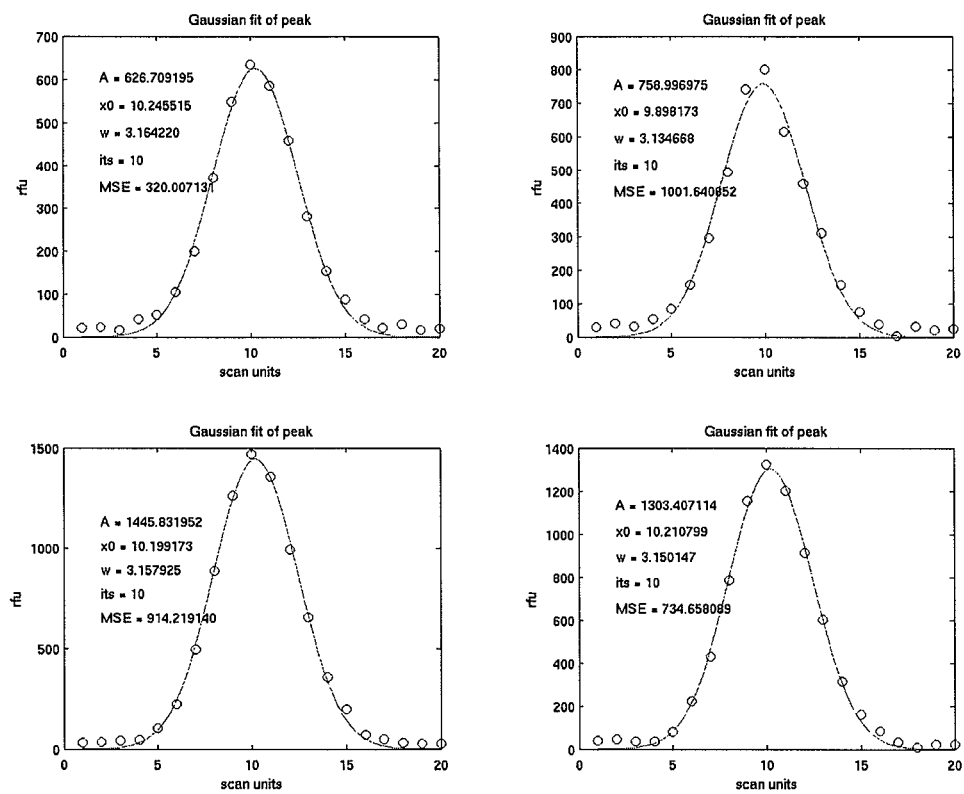
FIG. 23: Gaussian fits using the MATLAB lsqcurvefit built-in function of four peak data sets from raw ABI 310 data after color separation and baseline correction.
Figure 24:
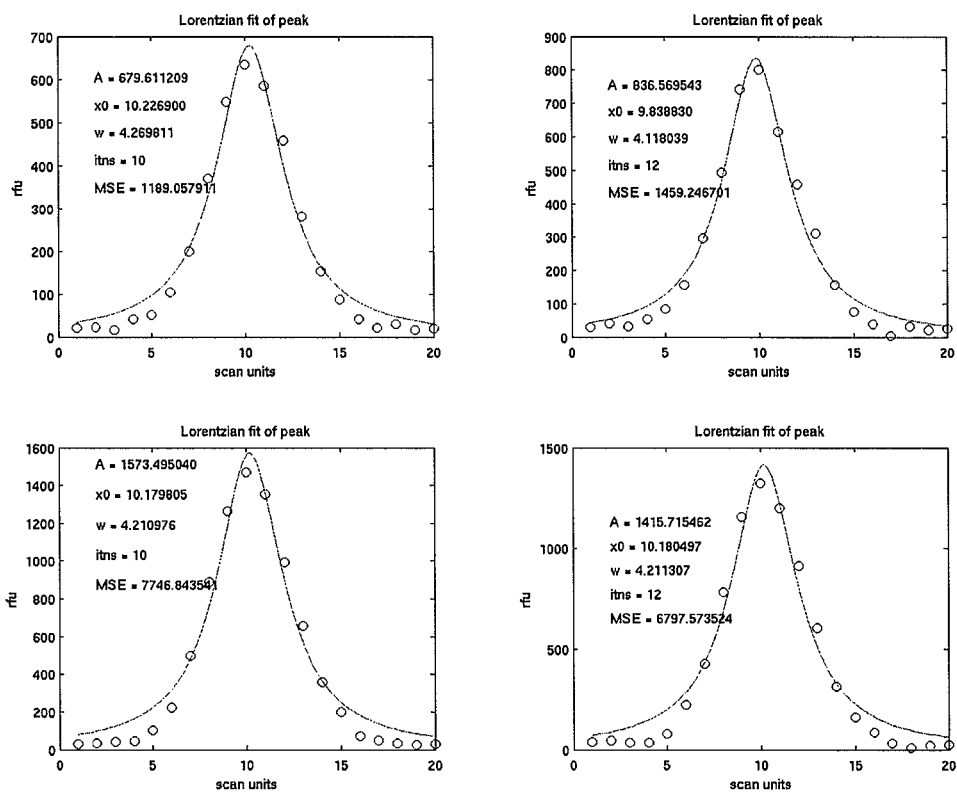
FIG. 24: Lorentzian fits using the MATLAB lsqcurvefit built-in function of the same data set as that shown in FIG. 23. Note that the low lying points are not fitted well by this model.
Figure 25:
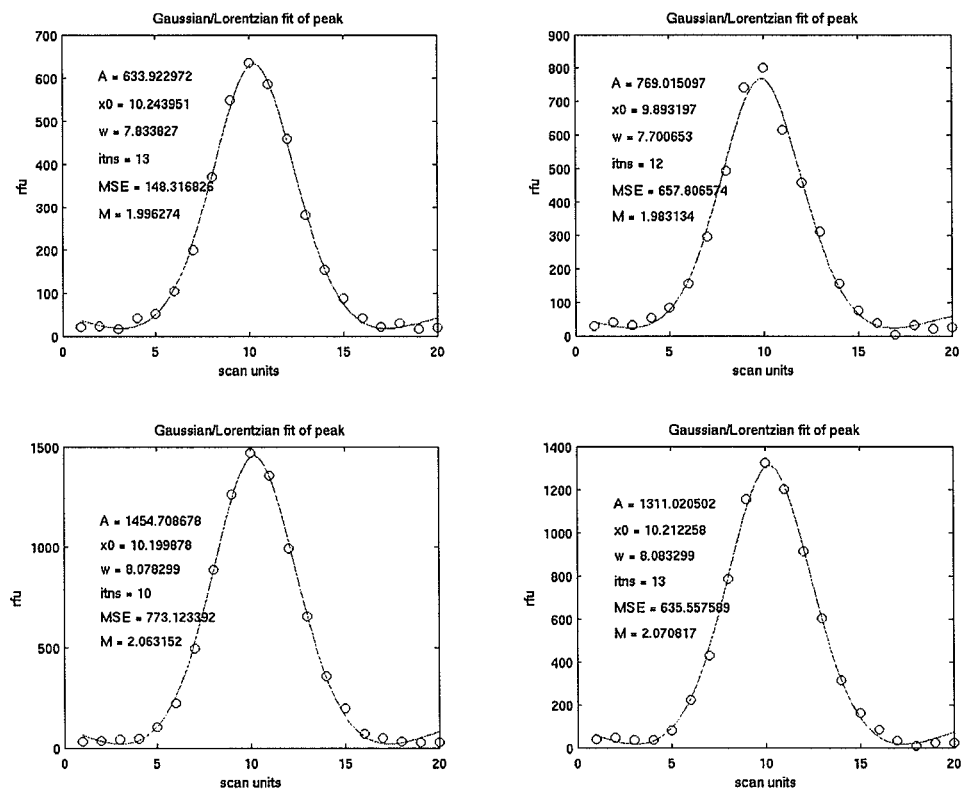
FIG. 25: Gaussian-Lorentzian mix fits using the MATLAB lsqcurvefit built-in function of the same data set as that shown in FIGS. 23 and 24. Note the improved fit but curled front and tail.

FIGS. 23, 24, and 25 contain four sample peaks fitted by the Gaussian, Lorentzian, or Gaussian-Lorentzian mix model equations, respectively. Each figure contains four fitted peaks with the corresponding optimized model parameters, the number of iterations required to converge, and the mean squared error of the fit for the data contained in the entire peak window. The same four peaks are fitted by each model and the results are summarized in Table 5.2.

Visually, the Gaussian and Gaussian-Lorentzian models seem to fit better than the Lorentzian model. The apparent peak height and the tails of the Lorentzian fits contain a larger amount of error compared to the Gaussian and Gaussian-Lorentzian models, evidenced by the correspondingly large MSE values. The Lorentzian fit overshoots the apparent height by close to 10\% in the example fits shown. The MSE of the Gaussian-Lorentzian model fits are lower than that of the Gaussian model, but the leading and trailing tail points of the mix model curl upwards near the baseline. This is due to the model's compensating for the nonzero baseline of the peaks and results in M parameter values near two. A value of two for M implies that the peak is a summation of a negative Gaussian of height A and a positive Lorentzian of height 2A (see Equation 5.3, above). Although this enables a closer fit at the tails than the Gaussian, both models give similar fits at the upper part of the peak. Since the main objective is to properly fit the peak height and position, it is not necessary to use the more complicated Gaussian-Lorentzian mix model to achieve the same quality of fit in the region of interest. The number of required iterations for each model was not conclusive for deciding the time to convergence, as they all required around twelve iterations on average. The mix model, however, would require more computations than the Lorentzian and Gaussian models per iteration due to its additional number of parameters involved in the optimization. Based on these results, the Gaussian model was determined to be a suitable model for fitting the ideal peaks as described in Section 4.1. It was chosen over the other two models for its simplicity compared to the Gaussian-Lorentzian mix model and performance over the Lorentzian model. The feasibility of using the Gauss-Newton method to fit peaks was also established and the proposed solution approach could then be developed in C++.

TABLE 5.2

Summary table of MATLAB results using the Gaussian,
Lorentzian, and Gaussian-Lorentzian mix model equations
to fit peak data using the Gauss-Newton method.

|  |  | Gaussian | Lorentzian | G/L Mix |
|---|---|---|---|---|
| Peak 1 | A | 626.709192 | 679.611209 | 633.922972 |
|  | $x_c$ | 10.245515 | 10.226900 | 10.243951 |
|  | $\sigma$ | 3.164220 | 4.269811 | 7.833827 |
|  | M |  |  | 1.996274 |
|  | its | 7 | 10 | 13 |
|  | MSE | 320.007131 | 1189.057911 | 148.316826 |
| Peak 2 | A | 758.996975 | 836.569543 | 769.015097 |
|  | $x_c$ | 9.898173 | 9.838830 | 9.893197 |
|  | $\sigma$ | 3.134668 | 4.118039 | 7.700653 |
|  | M |  |  | 1.983134 |
|  | its | 13 | 12 | 12 |
|  | MSE | 1001.640852 | 1459.246701 | 657.806574 |
| Peak 3 | A | 1445.846335 | 1573.495040 | 1454.708678 |
|  | $x_c$ | 10.199177 | 10.179805 | 10.199878 |
|  | $\sigma$ | 3.157992 | 4.210976 | 8.078299 |
|  | M |  |  | 2.063152 |
|  | its | 13 | 10 | 10 |
|  | MSE | 914.218834 | 7746.843541 | 773.123392 |
| Peak 4 | A | 1303.409294 | 1415.715462 | 1311.020502 |
|  | $x_c$ | 10.210821 | 10.180497 | 10.212258 |
|  | $\sigma$ | 3.150168 | 4.211307 | 8.083299 |
|  | M |  |  | 2.070817 |
|  | its | 13 | 12 | 13 |
|  | MSE | 734.658052 | 6797.573524 | 635.557589 |

The data set corresponds to that used in FIGS. 23, 24, and 25. The data indicate that Gaussian and Gaussian-Lorentzian mix model fits produced comparable height and center results. The Lorentzian model fits contain large MSE values compared to the other two model fits.

TABLE 5.3

Summary table for parameters used in the Gauss-Newton method.

| Max Iterations | 500 |
|---|---|
| $\gamma$ | 1e-10 |
| $\beta$ | .5 |
| $\sigma$ | .1 |
| s | 1 |

The $\gamma$ and Max Iterations parameters are used for the stopping criteria. $\beta$, $\sigma$, and s are scalars used in the Armijo stepsize rule as described in Example 1B.

Basic Implementation of Gaussian Fitter Using C++

The MATLAB implementation demonstrated feasibility of the approach. Because the expert system is written in the C++ programming language, the peak fitter must be developed in C++ as well for integration. A C++ implementation of the Gauss-Newton method described in Example 1B was developed into a standalone program. The code is modular so that the peak model equations can be easily modified without changing other aspects of the implementation; the initial implementation was carried out using the Gaussian model. The software required development of two major parts: the Gauss-Newton algorithm and Gaussian model fitting.

The Gauss-Newton methodology is an iterative optimization method that continues until a stopping criteria is reached. The stopping criteria was determined by either reaching a specified maximum number of iterations or observing a small enough change in the cost, $\Delta J$, between successive iterations. The method will continue until the inequality, $\Delta J > \gamma J$, is no longer true, where $\gamma$ represents the scaling factor (chosen by the user) applied to the current cost. Coding the algorithm is straightforward but is slightly complicated by the use of matrices. The update equation, Equation 4.3, requires a matrix pseudoinverse to be performed. This was accomplished through the use of the singular value decomposition (SVD) function that was available in the C++ Template Numerical Toolkit (TNT) using the JAMA/C++ Linear Algebra Package [4]. The pseudoinverse could then be calculated by using the equation $A^+ = V \Sigma^+ U^T$, where V, $\Sigma$, and U are matrices from the SVD result, and $\Sigma^+$ denotes the pseudoinverse of $\Sigma$. The rest of the computations required are calculated using the built-in C++ math library. Table 5.3 summarizes the constants used in the Gauss-Newton implementation. The values used for the Armijo scalars are the default parameters suggested by Bertsekas [8]. These values are set when the method is instantiated.

TABLE 5.4

Comparison of Gaussian fits obtained using C++ and MATLAB.
The four peaks show negligible difference in optimized parameters.

| Peak # | Param | MATLAB | C++ | % difference |
|---|---|---|---|---|
| 1 | A | 626.709192 | 626.709195 | 4.30e-07 |
|  | $x_c$ | 10.245515 | 10.245515 | 4.45e-06 |
|  | $\sigma$ | 3.164220 | 3.164220 | 4.56e-06 |
| 2 | A | 758.996975 | 758.996975 | -9.44e-09 |
|  | $x_c$ | 9.898173 | 9.898173 | -2.56e-06 |
|  | $\sigma$ | 3.134668 | 3.134668 | -2.56e-06 |
| 3 | A | 1445.846335 | 1445.831952 | -9.95e-04 |
|  | $x_c$ | 10.199177 | 10.199173 | -4.03e-05 |
|  | $\sigma$ | 3.157992 | 3.157925 | -2.11e-03 |
| 4 | A | 1303.409294 | 1303.407114 | -1.67e-04 |
|  | $x_c$ | 10.210821 | 10.210799 | -2.19e-04 |
|  | $\sigma$ | 3.150168 | 3.150147 | -6.73e-04 |

The Gaussian model as described by Equation 4.1 requires its partial derivatives with respect to each of the parameters to be also specified in the code when used with the Gauss-Newton method. Expressions for the partial derivatives were calculated from the original $f(x,p)$ function using MATLAB and then included in the C++ implementation.

The Gauss-Newton method was designed to handle equations with an arbitrary number of parameters.

Figure 26:
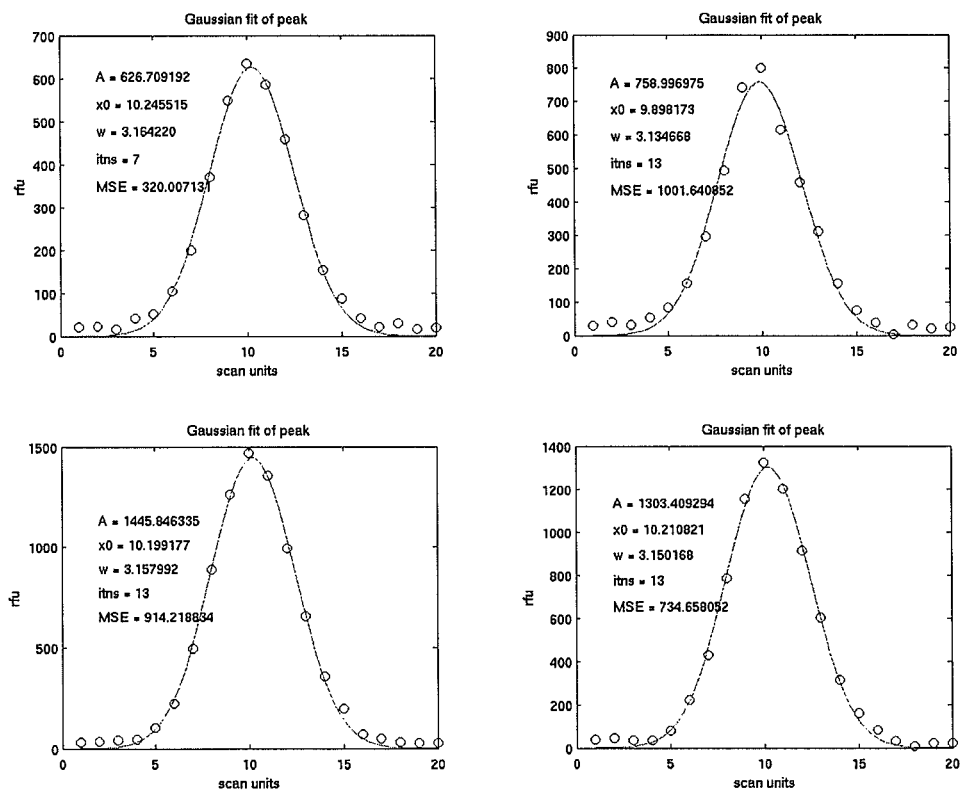
FIG. 26: Gaussian fits using C++ implementation of the peak fitter. Data are the same as that used in FIG. 23.

The first implementation was a standalone C++ program used to verify that the Gauss-Newton method was correctly coded and that the Gaussian model equation was properly integrated. The same sample data used in Example 2A for the MATLAB testing were used to test the C++ implementation of the fitter. Fitting results are shown in FIG. 26 and are compared to the MATLAB results from FIG. 23. Results shown in Table 5.4 indicate that the C++ implementation provides comparable fitting accuracy to that of the MATLAB routine. Parameters obtained using MATLAB and C++ for the Gaussian model are the same to within .002%. The varying % difference in the different peaks could be due to the MATLAB and C++ implementations potentially using different stopping criteria. The C++ optimization terminates after fewer iterations than the MATLAB implementation for the peaks with larger % difference. This could be due to the cost change $\Delta J$ as opposed to parameter change $\Delta n$ between iterations being used for the stopping criteria for C++ and MATLAB, respectively. The small difference in peak parameters could also be attributed to the stepsize determination rule used. The C++ implementation uses the Armijo rule, while the MATLAB built-in function uses a mixed quadratic and cubic polynomial interpolation and extrapolation line search algorithm [5].

After verifying that the Gauss-Newton method implementing the Gaussian peak model fit was properly implemented in a standalone form, it was integrated into the expert system application. Because the expert system is based on an object oriented design, the Gaussian fitter was implemented as a C++ class object from a derived peak fitter class. This allows different fit models to be easily created and incorporated by producing new derived classes as needed.

EXAMPLE 2B

Implementation of Fitter Framework

In order to better fit the various types of peaks that will be encountered, a framework is given that will attempt fits using different peak equation models and, based on the results, automatically choose the best fit type for the peak. The initial implementation using the Gaussian model can only handle symmetric ideal peaks properly. Non-ideal peaks can be fitted but may result in large amounts of error, or in some cases do not converge. Non-ideal peaks such as narrow, noise, and saturated peaks can still be modeled with the Gaussian peak equation, but the optimization does not always properly identify the peak parameters using the initial implementation. Additional peak models were described in Example 1 to better model asymmetric and dual peaks. In addition to the Gaussian peak model, the Hybrid peak model (Equation 4.8) and Dual peak model (Equation 4.9) were added. With these three models implemented, multiple fit types were developed to accommodate the various kinds of expected peaks in the measurement data. The logic required to call a specific fit type and to assess the fitting results, along with the details of each fit type, are described below.

The peak fitter framework used in the expert system incorporates multiple stages of analysis to determine the most appropriate fit to be used for a peak. Narrow, Saturated, Default (Gaussian), Hybrid, Dual, and Direct are the available fit types that are implemented. Four special functions exist that contain the intelligence of the fitter in deciding the flow of the fit logic: Check Peak, Check Fit, Revert, and Update Peak. These functions use the peak window data and fitted parameter values obtained from the current fit type to determine which fit type to call subsequently or which fit type to accept. The basic goal of the fitter is to efficiently calculate a peak fit with an emphasis on the accuracy of peak center and height parameters. The system automatically tries fits until a suitable fit is found among the fit types that satisfies a specified set of acceptance criteria. This is done in a way to minimize computation by performing simpler fits first.

Figure 27:
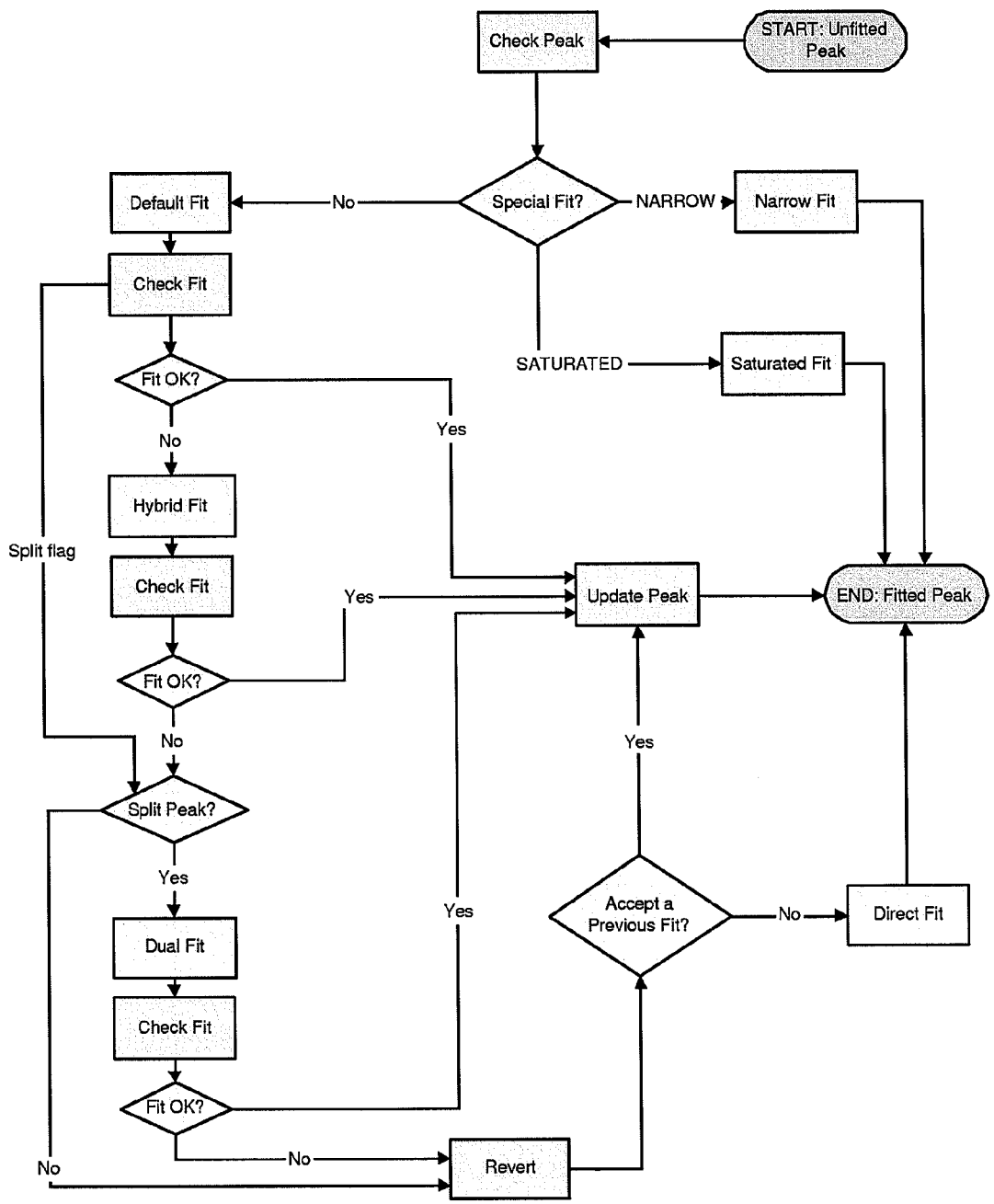
FIG. 27: Flow of the advanced C++ peak fitter framework. An unfitted peak data window enters the peak fitter. An initial scan determines if a Narrow or Saturated fit is to be performed. If not, other fits are tried in sequence until one is accepted. If none is accepted in the first pass, the revert function chooses the best of the fits attempted so far. If none are suitable, the Direct fit is then applied as the last resort.

The flow diagram for the peak fitter framework is shown in FIG. 27. The following sections explain the flow step by step and describe the decision that triggers a particular subsequent fit type.

Fit Type Functions

Figure 28:
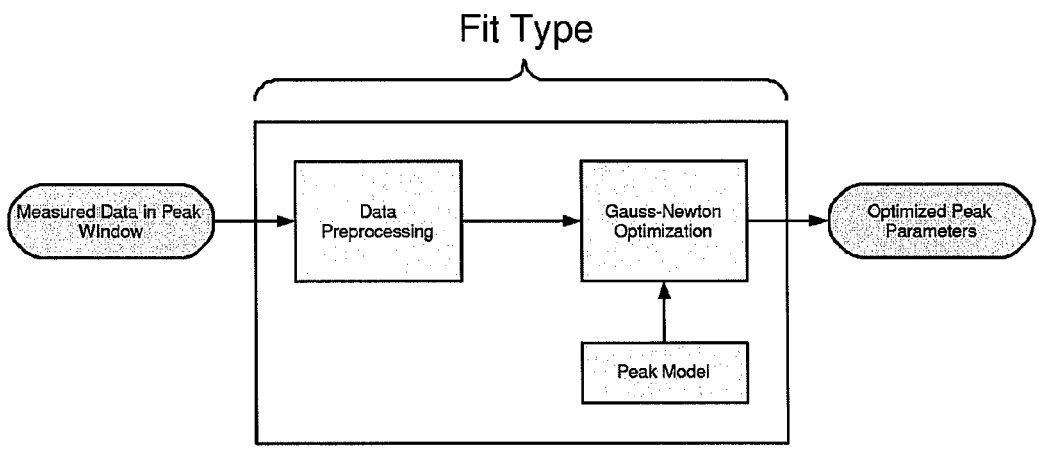
FIG. 28: Generic fit type block diagram showing the inputs and outputs of a generic fit type. Measured data enter in peak window; some form of preprocessing is applied to the window, a peak model is chosen to be optimized by the Gauss-Newton method, and the optimized peak parameters are returned.

This section describes each of the fit types and the Check Peak, Check Fit, Update, and Revert functions used to make flow decisions in the implementation of the framework. The various fit types are implemented by the following functions: Narrow, Saturated, Default, Hybrid, and Dual. An additional type, the Direct fit type is a 'catch all' fit performed when none of the previously stated fits is acceptable. FIG. 28 gives the generic flow for the fit type functions. Each fit type uses one of the three peak model equations discussed in Example 1 to model the data (Equations 4.1, 4.8, and 4.9). All of the fit types use the Gauss-Newton optimization method to determine the final model parameters, except for the Narrow and Direct fit types in which the parameters are directly determined algebraically based on the peak window data. A certain amount of window data preprocessing takes place to prepare the data for optimization depending on which fit type is being used. For the Default fit, Hybrid fit, and Dual fit functions, the peak parameters are returned after optimization and subsequently analyzed by the Check Fit function for acceptance. The peak fit types are described in the order in which they occur during the peak fitting framework, and the conditions under which they are called and the corresponding fit results accepted are also given.

Check Peak Function

After a peak detection window is formed, the first step in the peak fitter framework is the initial check of the measurement data using the Check Peak function. The Check Peak function performs a scan of the peak data to determine if either of the two special fit types is appropriate (Narrow fit or Saturated fit). It looks among the peak data for the existence of only a few points that lie above the peak detection threshold for a narrow peak or the presence of saturated points in the corresponding raw electropherogram data (before color separation) for a saturated peak. If either of these two conditions is detected, the fit type is set to Narrow or Saturated accordingly. For all other peak types, the function determines the 'fit window'. The fit window is a subwindow of the peak window, containing all points above the peak fit threshold to the left and right of the peak window maximum. The peak fit threshold (PEAK_FIT_THRESH) is a parameter set in the EXPERT SYSTEM application in order to ignore data points that lie at the bottom N % of the peak window (with respect to the maximum RFU value) in order to keep noisy baseline data from entering the fit, where N is typically less than 10%. If the calculated fit window would cause the peak to be classified as a narrow peak (too few points), then the entire peak window is used. The reduced fit window is only used for the Default and Hybrid fits; all other fit types use the entire peak window.

Narrow Peak Fit Function

When a peak window has too few points or there are not enough points in the proximity of the peak maximum, the Check Peak function asserts that a Narrow Peak fit by a simple Gaussian model must be performed. Peaks of this type do not contain enough information to be properly fitted using an optimization method and must have their Gaussian model parameters algebraically computed directly from the peak data.

The height A and center location $x_c$ assigned to the peak are the RFU and scan unit values of the peak window's maximum point, respectively. The peak width measure $\sigma$ is calculated based on the size of the peak window. The FWHM value is set as half of the peak window size, in scan units, and is used to calculate $\sigma$ by the relation $$\sigma = \sqrt{\frac{w_{FWHM}^2}{4\ln 2}}.$$

Figure 29:
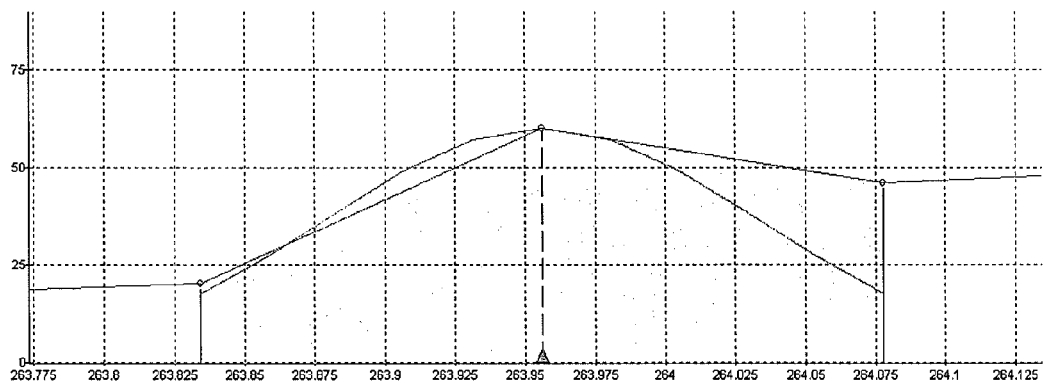
FIG. 29: Direct fit of a narrow peak to a Gaussian equation where the model parameters are calculated directly from the peak data.

The Narrow fit is self sufficient in that it sets all peak attributes independently instead of using the Update Peak function, which is described later. A sample Narrow fit can be seen in FIG. 29. Table 5.5 shows a summary of the Narrow fit.

TABLE 5.6

Summary table for Saturated fit.

| Fit model | Gaussian |
|---|---|
| Fit equation | $f(x, p) = Ae^{-(\frac{x-x_c}{\sigma})^2}$ |

TABLE 5.6-continued

Summary table for Saturated fit.

| | |
|---|---|
| Optimization parameters | p = [A, $x_c$, σ] |
| FWHM measure | 2σ√ln2 |
| Fit window | All unsaturated points |

Saturated Peak Fit Function

When the Check Peak function indicates there are saturated data, this function removes the saturated data points (points at maximum RFU value before color separation) and performs a fitting using the simple Gaussian model. The initial guess for the parameter vector uses the following values: the maximum possible RFU value(8,192) for the A, half of the window length in scan units minus one for $x_c$, and a constant value for the σ (4 currently used). If there are not enough points left (6 minimum) after the saturated points are removed or if the fitter fails to converge, a Default fit is then attempted. If the default fit fails to converge or results in invalid parameters, a Direct fit is then applied.

Figure 30:
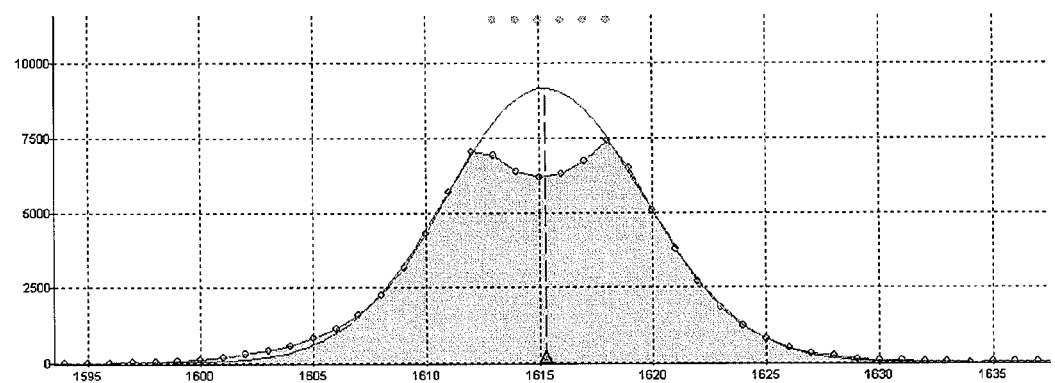
FIG. 30: Fit of a saturated peak. The saturated points are discarded in fitting and the remaining window data points are fitted with a Gaussian model. The fitted curve reconstructs the saturated region.

It must be stressed that saturated fits are performed merely to give an idea of what the peak may look like visually to the user, but EXPERT SYSTEM should not use them as valid peaks to attempt for an allele call. Additionally, the Saturated peak fit will only apply to data that are not previously color separated because the presence of saturation is only detected from the raw electropherogram data before color separation since saturated intensity is clamped at 8,192 RFU, the maximum detection limit by the instrument. Since the raw ABI 3100 data are already color separated, saturated data can not be detected, and this fit can not be performed. A sample fit using the saturated fitter is shown in FIG. 30. Although the measurement data are distorted by the saturated points, the fitter is able to reconstruct the peak. Table 5.6 shows a summary of the Saturated fit. This fit type is self sufficient in that it sets all peak attributes independently instead of using the Update Peak function as described.

Default Peak Fit Function

Figure 31:
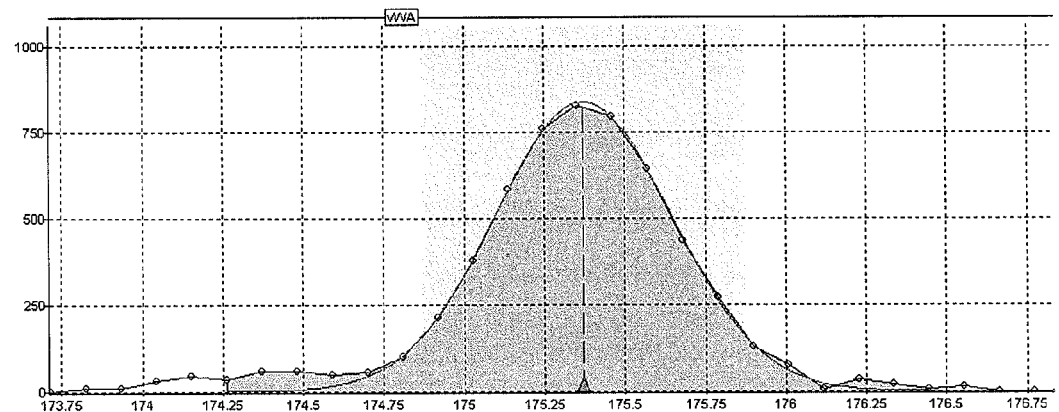
FIG. 31: Default fit of an ideal peak by a simple Gaussian model. The fit window used leaves out data in the lower 10% of the peak relative to the peak maximum value and allows the optimization to closely fit the top of the peak without being negatively impacted by the noise at the tails of the peak.

If the Check Peak function does not trigger a Saturated or a Narrow fit, the Default fit is attempted next. This fit uses the Gaussian peak model and is performed first among the family of main fit types (Default, Hybrid, and Dual) because it is the simplest. The fit window determined in the Check Peak function is used for this fit type. Symmetric ideal peaks can be adequately fitted by this fit type. The initial guess for the parameter vector uses the peak window maximum value and position for A and $x_c$, respectively. The initial σ is given a constant value (4 currently used). After the optimization is performed, the quality of the fit is determined by the Check Fit function. If the Check Fit function fails or the optimization does not converge, a Hybrid fit function is evoked next. Otherwise, the fit is accepted and the peak attributes are set in the Update Peak function. FIG. 31 shows an example of fit using this routine. Table 5.7 shows a summary of the Default fit.

TABLE 5.7

Summary table for Default fit.

| | |
|---|---|
| Fit model | Gaussian |
| Fit equation | $f(x, p) = Ae^{-(\frac{x-x_c}{\sigma})^2}$ |
| Optimization parameters | p = [A, $x_c$, σ] |
| FWHM measure | 2σ√ln2 |
| Fit window | Points above PEAK_FIT_THRESH |

Check Fit Function

The Check Fit function is implemented after a Default, Hybrid, or Dual fit is carried out. The purpose of the Check Fit function is to determine if the current fit is appropriate for the given peak data. It checks first if the returned peak parameters are valid. For parameters to be valid in Default and Hybrid fits, the peak center must be contained within the peak window, the height must be a nonnegative value above the minimum peak height and below the maximum possible RFU value (8,192), and the width must be under a specified maximum threshold ($\sigma_{max}$=20). Dual fits use the same set of constraints and in addition require that the two peak centers be separated by a specified number of scan units (currently 4). If any of the returned fit parameter values is invalid, then the fit type is automatically rejected.

If all the parameters are deemed valid, error envelopes are then applied to detect the presence of unacceptable excursions in the residuals between the fitted and the measured peak data. Because the center and height are the most important characteristics to extract, two error excursion envelope bounds are established, based on the maximum peak height. The objective is to penalize more excursions occurring in the region of the peak closer to the peak maximum. The primary fit zone is determined by a parameter specifying the percentage of the top of the peak to include in the primary region (The default is the top 40% of the peak set by the PEAK_PRIM_FIT_ZONE parameter). All points equal to or above this threshold are considered primary and all points less than the threshold are considered secondary. Each zone has its error envelope independently established (PEAK_PRIM_ERR_ENV and PEAK_SEC_ERR_ENV). This gives the system the ability to enforce a tighter bounding envelope on the primary points in the peak for a closer fit and place less emphasis on the fits of the tailing points. Excursions that occur in the primary region and left and right secondary regions are all recorded separately. Note that instead of using primary and secondary regions, Dual fits use a single constant bounding envelope across the entire window bounded by the split peak envelope (PEAK_SPLIT_ENVELOPE).

Figure 32:
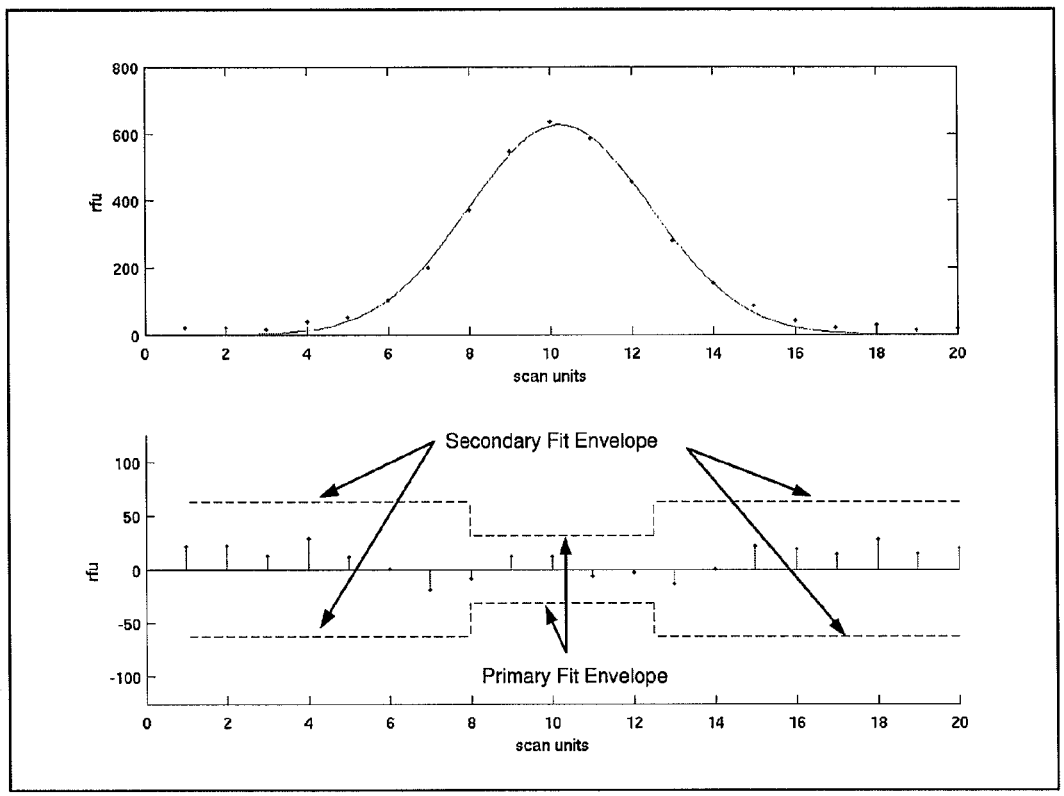
FIG. 32: Error and error bounding envelopes for a sample peak. The top part of the figure shows a peak window fitted using a Gaussian model. The bottom contains the corresponding residual between the fitted and the original points.

FIG. 32 shows an sample Default fit and its corresponding residual and error envelopes. If there are no excursions beyond the bounding envelope, as in this example, the peak parameters and fit type will be accepted. If any unacceptable excursions are detected, the fit is deemed inappropriate and the next fit type function will be evoked and attempted.

In addition to checking validity of the parameters and detecting unacceptable excursions, Check Fit also determines the disposition of the 'Split' flag and calculates the MSE measurement. When Check Fit is applied to the Default fit parameters, the Split flag setting will be determined to indicate if a Dual fit should be attempted. This flag will be set if the fitted peak window maximum RFU value is greater than the minimum dual height (PEAK_MFIT_THRESHOLD) and the number of alternating (in sign) envelope excursions is less than the maximum number allowed (PEAK_MAX_EXCURSIONS). These two parameters, described in detail in Example 2B, are used to prevent the Dual fit from being triggered on small or noisy peak shapes. The MSE is calculated and stored for use by the Revert function if it is called.

Hybrid Peak Fit Function

Although the Gaussian model provides a good general fit for the majority of peaks, peaks with asymmetric characteristics require a different model. The Hybrid model described in Example 1D is used in this fit type to improve the fit when a Default fit fails. Similar to the Default fit, the Hybrid fit uses the fit window that was determined by the Check Fit Function. The initial guess for the parameter vector uses the peak window maximum value and the position for A and $x_c$, respectively. The initial $\sigma$ is given a constant value (4 currently used). After the optimization step converges, the Check Peak function is again used to determine if the fit is acceptable. If Check Fit determines the peak fit is good, the peak attributes are set by the Update Peak function and the fitting is complete. If Check Fit fails, a Dual fit will automatically be performed next if the Split flag was also set by the Check Fit function after the Default fit. Otherwise, the Revert Function will be called to review all previous fits and pick the best from them as the final fit.

Figure 33:
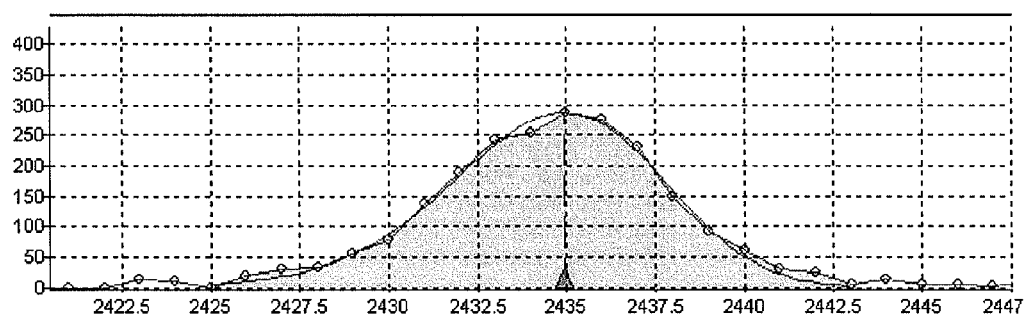
FIG. 33: Hybrid fit of a skewed peak. The fit window used leaves out data in the lower 10% of the peak relative to the peak maximum value and allows the optimization to closely fit the top of the peak without being negatively impacted by the noise at the tails of the peak.

A sample peak fitted by the Hybrid fit is shown in FIG. 33, in which the asymmetry parameter $\tau$ is found to be −0.6 indicating a longer left shoulder. Table 5.8 gives a summary for the Hybrid fit.

Dual Peak Fit Function

Figure 34:
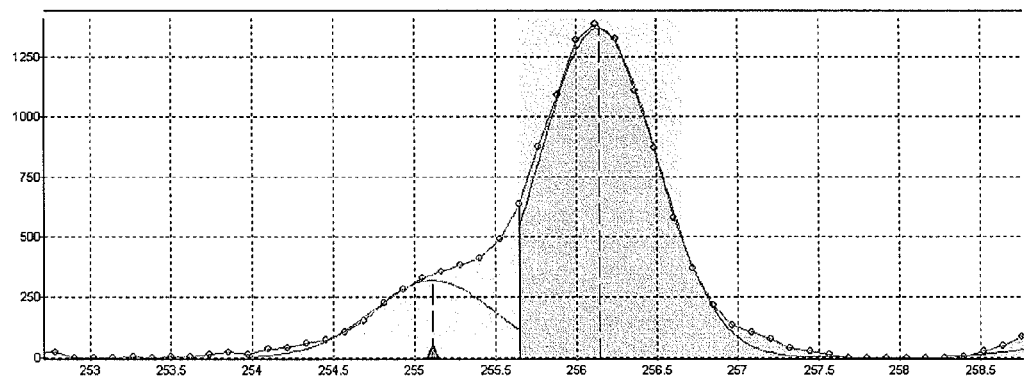
FIG. 34: Dual fit of a −A/+A set of peaks in which two Gaussian curves with separate peak maximum, center, and width measure are applied to fit the data. The solid line in-between the peaks indicates the peak window boundary between the two peaks.
Figure 35:
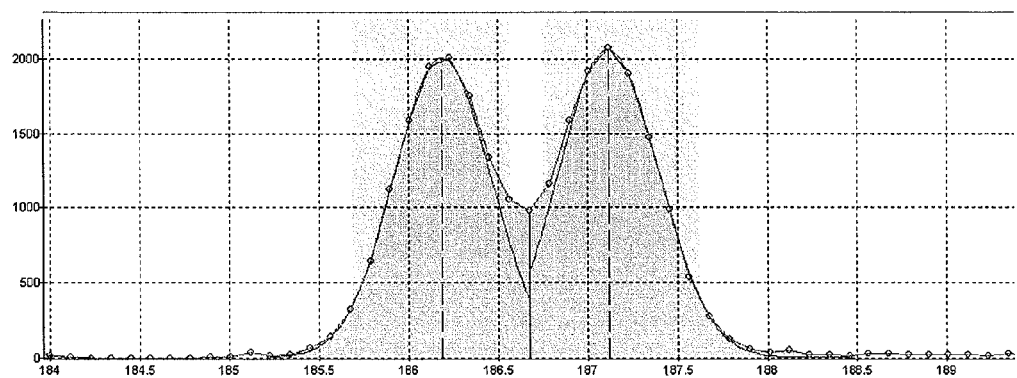
FIG. 35: Dual fit of TH01 9.3/10 allele peaks in which two Gaussian curves with separate peak maximum, center, and width measure are applied to fit the data. The solid line in-between the peaks indicates the peak window boundary between the two peaks.

Dual peak fitting is required to resolve −A/+A peaks and to separate 9.3/10 TH01 peaks in which both are separated by only one base pair. The previous fit types can only handle one peak per window. This function uses the dual peak model described in Example 1D and is evoked when the Check Fit function determines that the data in the window meet the split criteria. However, the Dual fit will then only be performed if both the Default and the Hybrid fits have been evoked and failed. The actual flow of the Dual fit requires two separate prior regular Gaussian fits to acquire two sets of initial parameters in order for the dual fitter to commence iteration. To start the two regular Gaussian fits, a sub-window of the peak window is formed by collecting all points that are monotonically decreasing away from the window's maximum (to the left and right). This is intended to identify and separate the larger of the peaks in the window. After performing a Gaussian fit using only the points in this sub-window, the fitted points as predicted by the model are then subtracted from the data points in the original window. With the major peak subtracted off, a second Gaussian fit is performed on the resultant data over the whole window. The intention is that the residual will correspond to the minor or smaller peak. These fits will not accurately extract the correct dual peak parameters, but they will provide a good starting point for the subsequent Dual fit. After the optimization is performed using the calculated initial parameters as the starting points, the Check Fit function determines whether the Dual fit results are acceptable. If the parameters are valid and there are no excursions based on the split peak boundary envelope determined by PEAK_SPLIT_ENVELOPE, the Update Peak function separates the peaks into two Gaussian modeled peaks; otherwise it is sent to the Revert Function. Two sample Dual peak fits can be seen in FIGS. 34 and 35 showing fits for −A/+A and TH01 9.3/10 peak data, respectively. Table 5.9 gives a summary of the Dual fit.

TABLE 5.8

Summary table for Hybrid fit.

| Fit model | Exponential Gaussian Hybrid |
|---|---|
| Fit equation | $f(x, p) = \begin{cases} Ae^{\left(-\frac{(x-x_c)^2}{\sigma^2+\tau(x-x_c)}\right)}, & \sigma^2 + \tau(x - x_c) > 0 \\ 0, & \sigma^2 + \tau(x - x_c) \leq 0 \end{cases}$ |
| Optimization parameters | $p = [A, x_c, \sigma, \tau]$ |
| FWHM measure | $\sqrt{(\ln 2\tau)^2 + 4\ln 2\sigma^2}$ |
| Fit window | Points above PEAK_FIT_THRESH |

TABLE 5.9

Summary table for Dual fit.

| Fit model | Gaussian |
|---|---|
| Fit equation | $f(x, p) = A_1 e^{-\left(\frac{x-x_{c1}}{\sigma_1}\right)^2} + A_2 e^{-\left(\frac{x-x_{c2}}{\sigma_2}\right)^2}$ |
| Optimization parameters | $p = [A_1, x_{c1}, \sigma_1, A_2, x_{c2}, \sigma_2]$ |
| FWHM measure | $2\sigma_1\sqrt{\ln 2}, 2\sigma_2\sqrt{\ln 2}$ |
| Fit window | All points |

Revert Function

In the event that none of the fit types of Default, Hybrid, and Dual fits is initially accepted by the Check Fit function, the Revert function takes action. This function looks at the previous fits and attempts to choose the best one.

The peak fit that has converged, resulted in valid parameters, and has the lowest MSE measurement is chosen as the best fit. For parameters to be valid in Default and Hybrid fits, the peak center must be contained within the peak window, the height must be nonnegative values above the minimum peak height threshold (PEAK_THRESH) and below the maximum possible RFU value (8,192), and the width must be under a maximum threshold (currently 20). Dual fits use the previous constraints and in addition require that the two peak centers be separated by a minimum set number of scan units (currently 4) and that the MSE be improved from the other fits by a certain percentage (PEAK_SPLIT_IMP). Note that the Revert function is active only after all the fits attempted previously have failed to be accepted by the Check Fit function. The Revert function is deciding which is the "best of the worst" fit for the given peak data. If none of the peak fits is chosen to be the 'best' by the Revert function, a Direct fit will then be performed on the data as a last resort. Otherwise, one of the fits is chosen and the peak is updated appropriately using the Update Peak function.

Update Peak Function

This function updates the peak attributes based on the peak type accepted by the Check Fit or the Revert function (Default, Hybrid, or Dual). It uses the peak parameters from the optimization and extracts and calculates all of the pertinent values. For Dual fits, it creates a second peak and splits the main window into two with a subwindow boundary at halfway between their peak centers. A summary of the attributes set by this function is given in Table 5.10.

TABLE 5.10

Attributes assigned by Update Peak function.

| Attribute | Description |
|---|---|
| fit type | Ultimate fit type used for the peak |
| height | Fitted height of the peak in RFU |
| center | Fitted center of the peak (location) in scan units |
| $\sigma$ | Fitted width for the peak |
| $\tau$ | Fitted skew for the peak (Zero for non Hybrid fits) |
| $\omega_{FWHM}$ | Calculated FWHM value |
| iterations | Number of iterations required to converge |
| area | Calculated peak area |

Direct Peak Fit Function

Direct fitting is the last type of peak attempted by the fitter. This type of fit is performed on data that have resulted in unacceptable results for all other fit types attempted. The Gaussian model is applied and the parameter values are chosen based on the basic characteristics found by scanning the peak window. The height and center location are the RFU and scan unit value of the window data maximum, respectively. The FWHM is set as half of the window length (in scan units) and used to calculate σ by the equation $$\sigma = \sqrt{\frac{w_{FWHM}^2}{4\ln 2}}.$$

Figure 36:
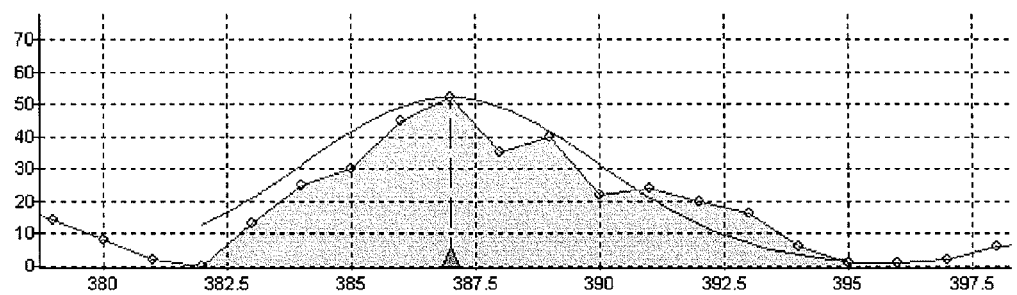
FIG. 36: Direct fit of peak data. Parameters directly assigned based on the maximum point in the window and the window size.

This routine does not undergo an optimization step. Results show that the majority of the peaks that are fitted with this method are noise peaks that just barely rise above the peak threshold. The Direct peak fit is self sufficient in that it sets all peak attributes independently instead of using the Update Peak function. A sample Direct fit can be observed in FIG. 36. Table 5.11 shows a summary of the direct fit.

TABLE 5.11

Summary table for Direct fit.

| | |
|---|---|
| Fit model | Gaussian |
| Fit equation | $f(x, p) = Ae^{-\left(\frac{x-x_c}{\sigma}\right)^2}$ |
| Parameters | $p = [A, x_c, \sigma]$ |
| FWHM measure | $2\sigma\sqrt{\ln 2}$ |
| Fit window | All points |

Fitter Configuration Parameters

The peak fitter uses a set of heuristically derived criteria that mimic the processes a human expert would use to decide the fit type to apply and accept. These parameters are used among all the Fit type functions. The criteria may be tuned by adjusting the values of a set of configuration parameters to control the stringency of the decision process. Table 5.12 shows the set of configuration parameters that have been developed, along with their default values. A description of each parameter is presented below.

PEAK_THRESH—Sample peak detection threshold. This is the minimum allowable height in RFU for a peak height. Peaks with fitted heights that fall below this height after a fit is accepted are discarded (checked outside of peak fitting framework).

PEAK_FIT_THRESH—Peak fit threshold (fraction of maximum height). When applied to the apparent RFU maximum of a peak window, all points below this fraction of the maximum height are ignored when fitting. This parameter enables the Default and Hybrid fits to exclude noisy baseline data from the fit, resulting in a tighter fit at the top of the peak.

PEAK_MFIT_THRESHOLD—Minimum peak height in RFU in the whole data window for Dual fit attempt. This keeps small amplitude noise peaks from improperly triggering Dual fits.

PEAK_MAX_EXCURSIONS—Maximum number of alternating peak envelope excursions allowed to consider a Dual fit. This keeps noisy peaks from improperly triggering Dual fits. Alternating excursions imply that the residual between the fitted peak data and the measurement peak data change signs for adjacent data points.

PEAK_PRIM_FIT_ZONE—Primary fit zone for the peak (fraction of maximum height in the peak window). Points equal to or above the threshold are considered primary points and points below the threshold are secondary points. This value separates the peak window for analysis of error bounding using the primary and secondary envelopes. This parameter enters in the determination to see if a fit is acceptable.

PEAK_PRIM_ERR_ENV—Primary error envelope factor in the primary fit region. Residuals between the fitted peak data and the measurement peak data exceeding this fraction of the peak height are considered primary excursions. Primary excursions are weighted more in determining the accuracy of the peak center and height, so this value should be smaller than or equal to the secondary error envelope factor value.

PEAK_SEC_ERR_ENV—Secondary error envelope factor in the secondary fit region as a percentage of the peak maximum. Residuals between the fitted peak data and the measurement peak data exceeding this fraction of the peak height are considered secondary excursions. This envelope is applied to the points inside the secondary region.

This value should be set to a larger value than the primary error envelope factor value.

PEAK_SPLIT_ENVELOPE—Error envelope factor used for whole peak window in Dual Fits. Residuals between the fitted peak data and the measurement peak data exceeding this fraction of the maximum of the peak heights are considered excursions. Typically this value is set to the secondary error envelope value, but it can be adjusted for refinement of Dual Fit performance.

TABLE 5.12

Default analysis parameters for the peak fitter. They can be adjusted in the application to modify the behavior of the fitter.

| Parameter | Description | Default | Range |
|---|---|---|---|
| PEAK_THRESH | Sample peak detection threshold in RFU | 30 | ≥0 |
| PEAK_FIT_THRESH | Peak fit threshold | 0.10 | [0, 1] |
| PEAK_MFIT_THRESHOLD | Minimum peak height in RFU for Dual fit attempt | 300 | ≥0 |
| PEAK_MAX_EXCURSIONS | Maximum number of alternating peak envelope excursions allowed (for dual) | 6 | ≥0 |
| PEAK_PRIM_FIT_ZONE | Primary fit zone for the peak | 0.40 | [0, 1] |
| PEAK_PRIM_ERR_ENV | Primary error envelope factor in primary fit region | 0.05 | [0, 1] |
| PEAK_SEC_ERR_ENV | Secondary error envelope factor in secondary fit region. | 0.10 | [0, 1] |
| PEAK_SPLIT_ENVELOPE | Error envelope used for whole peak window in Dual Fits | 0.10 | [0, 1] |
| PEAK_SPLIT_IMP | Dual peak squared error improvement factor | 0.40 | [0, 1] |

PEAK_SPLIT_IMP—Split peak fit square error factor (fraction improvement). This is the fraction by which the mean square error must improve from the previously attempted fits to have a Dual fit be accepted when reverting. Any peak fit can be improved by modeling with two Gaussian peaks due to a larger number of model parameters to optimize over. This minimum improvement factor is used to prevent peaks that are not true dual peaks from being separated when the Revert function is used.

EXAMPLE 3

Testing the Peak Fitter Framework

Example 3 presents results and discussion from testing the peak fitter framework. It provides a description of the application of the peak fitter framework to a large data set, including the application parameters used, peak attributes recorded, and data used. Results also contain a comparison between the fitting results of peaks fitted by the fitter framework with the automatic flow of fit type decisions and a simple Gaussian fitter. Statistics on the peak fitter framework performance on a large data set (15,000+ peaks) is also given. Tabular and graphical results of the fitter performance are included. Limitations and problems encountered are also discussed.

EXAMPLE 3A

Applying the Peak Fitter Framework Using a Large Data Set

Results reported in this chapter are collected from software implementation of the peak fitter framework, as described in Example 2, that is integrated into the EXPERT SYSTEM expert system. All figures are extracted from the EXPERT SYSTEM graphical interface unless otherwise noted, and all peak attribute information is obtained through a peak export utility function. This export utility outputs all desired peak attributes to a text file for analysis. Table 6.1 lists the attributes that are obtained from the peak export file.

The fitter configuration parameters as described in Example 2B were set at their default values for the study. These parameter values have been listed in Table 5.12. A large set of peak data from COfiler and Profiler Plus runs was fitted by the framework.

EXAMPLE 3B

Evaluating the Effectiveness of the Design

The appropriateness of using advanced model equations was first evaluated by a comparison of the results of the full fitter framework to a simple Gaussian fitter based on a large data set. A set of basic statistics containing fitter results as a whole is also described. Sample figures demonstrating the advantages of using the framework with decision logic over a simple Gaussian fitter are given. The full fitter framework and simple Gaussian fitter will be abbreviated as FFF and SGF, respectively.

TABLE 6.1

Peak attributes obtained from the STRESP peak export function, after applying the peak fitter framework on a peak.

| Attribute | Description |
|---|---|
| run | Name of sample |
| dye | Fluorescent dye |
| locus | Locus name |
| allele | Allele name |
| revert | Flag indicating if fit selection is reverted |
| fit type | Type of accepted fit used on peak |
| iterations | Number of iterations for fit to converge |
| size | Size in base pairs |
| center | Fitted peak center location (scan units) |
| height | Fitted peak maximum height (RFU) |
| FWHM | Full width half max (scan units) |
| skewness | Measure of $\tau$ in Equation 4.8 |
| area | Calculated area of peak |
| MSE | Mean squared error |

TABLE 6.2

List of basic statistics of fit outcomes from the SGF and FFF or 20,834 peak windows.

| Attribute | SGF | FFF |
|---|---|---|
| number of peaks successfully fitted | 16598 | 17377 |
| maximum iterations | 501 | 399 |
| average iterations | 7.7886 | 8.3261 |
| maximum MSE | 1892480 | 1199540 |
| average MSE | 2.9490e+03 | 1.4882e+03 |
| maximum width | 100.6610 | 45.9451 |
| average width | 5.9622 | 5.8599 |
| maximum height | 4.9527e+04 | 1.5232e+04 |
| average height | 1.0248e+03 | 998.4727 |

Table 6.2 summarizes the statistics that support the claim that the FFF has a superior performance. The first value to notice is the total number of peaks successfully fitted by each approach. The SGF was able to fit 779 fewer peaks than the FFF, while both fitters receive 20,834 peak data windows. This is due to the SGF's inability to resolve dual peaks and properly fit low amplitude noise peaks. The peak parameters generated by the FFF also are more realistic in peak height and width. In contrast, the SGF produces for some peaks unrealistic maximum values of a 100 scan unit width (too wide) and a 49,000 RFU peak height (much too tall). The average values between the two fitters are similar, with the exception of the average MSE, which is twice as high in the SGF compared to the FFF. This implies that the fits are generally tighter in the FFF fitted peaks. Although these values indicate trends in fitting by the two approaches for the data set as a whole, they are not as useful in indicating the improvement in fit for each type of peak using the FFF. The next few paragraphs describe differences between the fits by the SGF and those by the FFF with respect to their performance in fitting various peak types.

Sample fits by both the FFF and SGF are given for each type of ideal and non-ideal peak as those described in Example 1A. These figures show examples of the various fit types that were implemented in the FFF and the improvement over that of a pure Gaussian fit.

The first set of figures contains fit types using the direct Gaussian fit decided by the FFF and the simple Gaussian fit in the SGF. Although a Gaussian model is used in both the FFF and SGF for these sample peaks, the peak data pre-check and optimal peak parameter validity checking in the FFF allow for the choice of a better fit of the given data by the resultant Gaussian model of the FFF with a different set of model parameters.

Figure 37A:
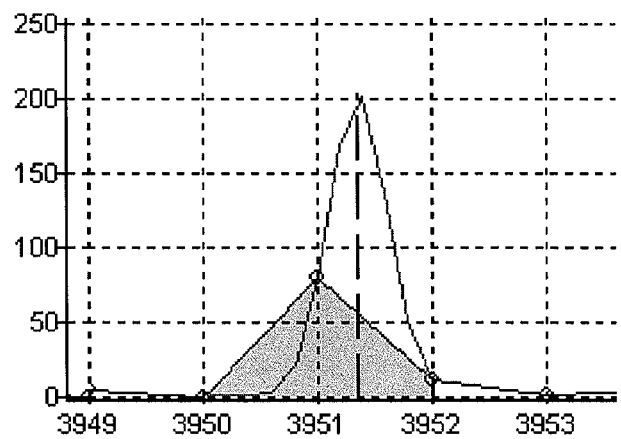
FIG. 37: Comparison of SGF to FFF for a narrow peak with too few points where the FFF properly evoked a Narrow fit. (a) The resulting SGF fit contains low fitting error but fails to model the peak height and position. (b) The resulting FFF fit is able to properly find the peak height and position.
Figure 37B:
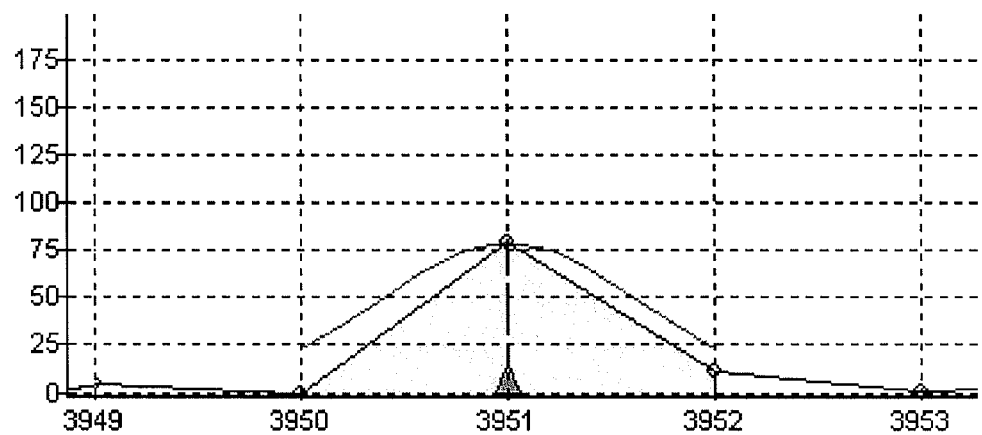
Figure 38A:
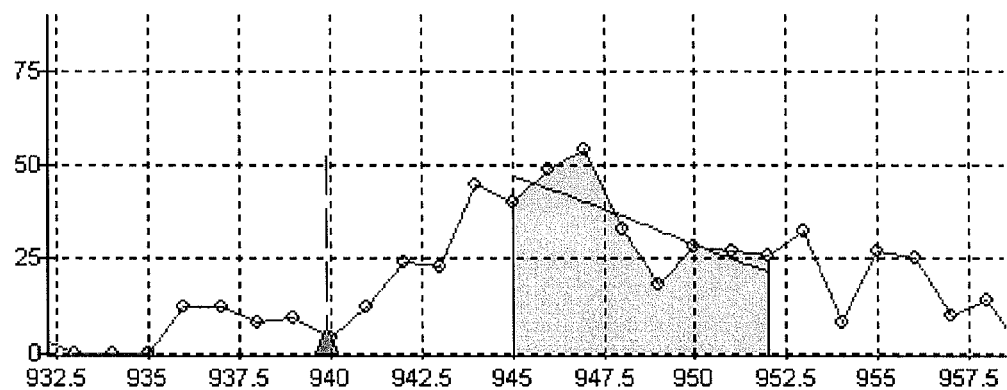
FIG. 38: Comparison of SGF to FFF for a low amplitude noise peak where the FFF properly evoked a Direct fit. (a) The resulting SGF fit converges on parameter values outside of the peak window. (b) The resulting FFF fit is able to effectively find the peak height and center given the window.
Figure 38B:
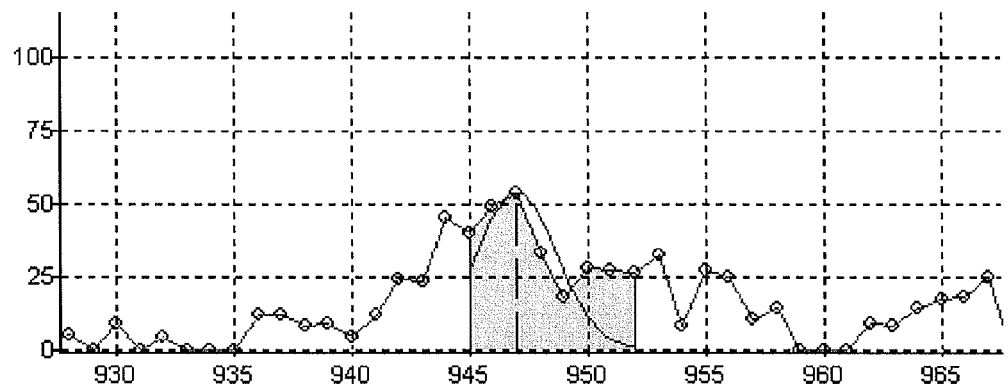
Figure 39A:
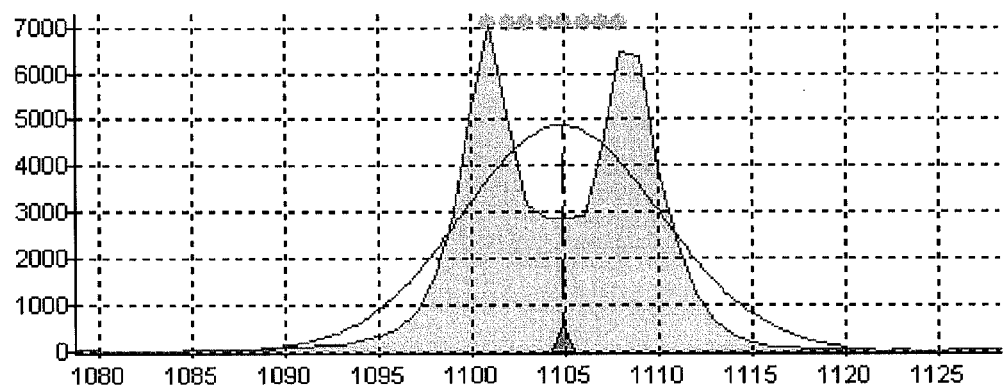
FIG. 39: Comparison of SGF to FFF for a saturated peak where the FFF properly evoked the Saturated fit type. (a) The resulting SGF fit contains a low height due to the inclusion of the distorted saturated points. (b) The resulting FFF fit is able to reconstruct the saturated peak by discarding the points that were saturated in the raw data.
Figure 39B:
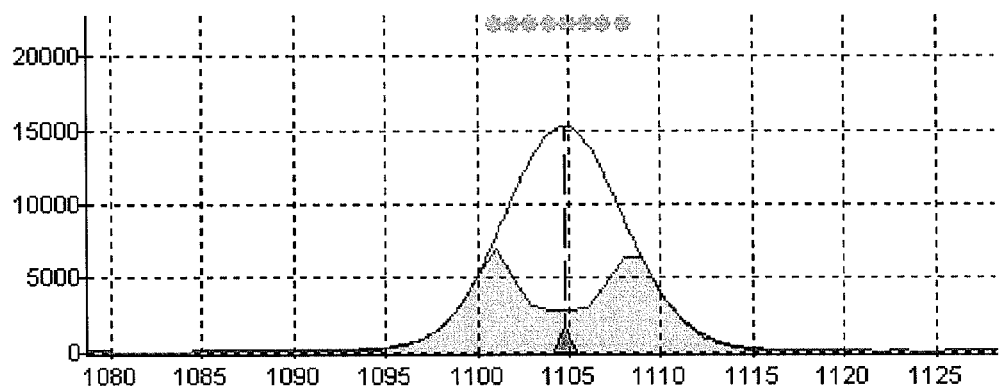

A narrow peak with a window containing too few points, in this case only three points, is first shown in FIG. 37. The SGF minimizes the error by fitting the points in the window but fails to model the actual peak shape (FIG. 37 (*a*)). The direct assignment of numerical values to narrow peaks' Gaussian model parameters by the FFF allows the fit to more closely model the apparent peak maximum height and center location (FIG. 37 (*b*)). FIG. 38 demonstrates the advantage of directly fitting noisy low amplitude peak data by a Gaussian model. The data contained in the peak window shown in this example cause the SGF fit to converge on parameters that are unrealistic (invalid). By directly assigning values to the parameters for this noise peak, the fit is better able to identify the peak height and center. An example of a saturated peak fitted by the FFF and SGF is given in FIG. 39. The decision by the FFF to ignore points in the saturated region (before color separation) allows the fitter to reconstruct a reasonable peak shape in the missing region. In contrast, the SGF fit of the data gives a height more than 10,000 RFU below that of the FFF fit because the saturated points are directly included in the data used by the fitter and bias the resultant peak height toward a much lower value.

TABLE 6.3

Statistics for the final fit types for all peaks in the study (17,377 peak fits).

| Fit Type | Avg. # Iterations to Convergence | # of Occurrences | Percent of Total |
|---|---|---|---|
| Total | 8.3 | 17377 | 100.00 |
| Direct | 0.0 | 350 | 2.01 |
| Default | 5.5 | 12709 | 73.14 |
| Hybrid | 23.6 | 2799 | 16.11 |
| Dual | 10.7 | 716 | 4.12 |
| Saturated | 17.7 | 61 | 0.35 |
| Narrow | 0.0 | 742 | 4.27 |

Figure 40A:
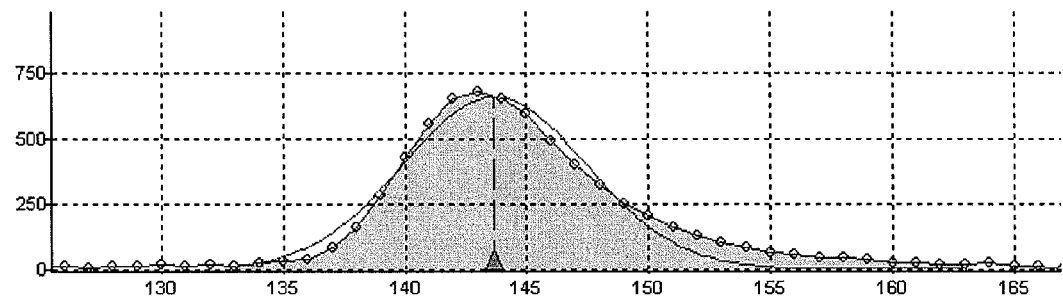
FIG. 40: Comparison of SGF to FFF fits for a skewed peak where the FFF properly chooses a Hybrid fit. (a) The resulting SGF fit has peak height and position values that deviate from the apparent height and maximum due to the peak skewness. (b) The resulting FFF fit is able to model the skewness of the peak using the Hybrid model. The peak height and position are much improved from the SGF fit.
Figure 40B:
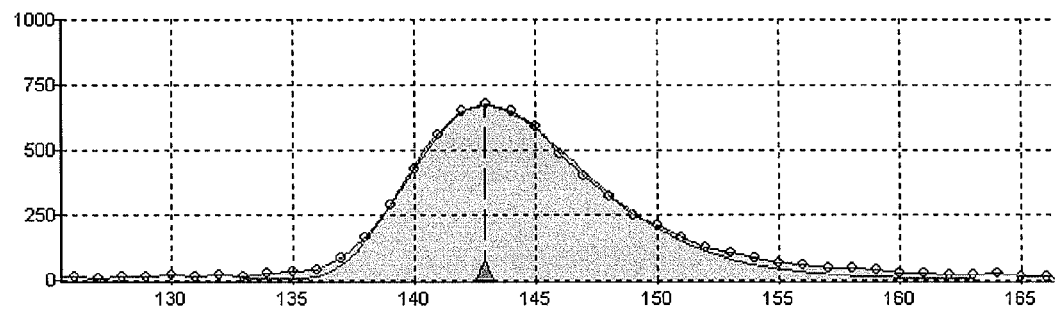
Figure 41A:
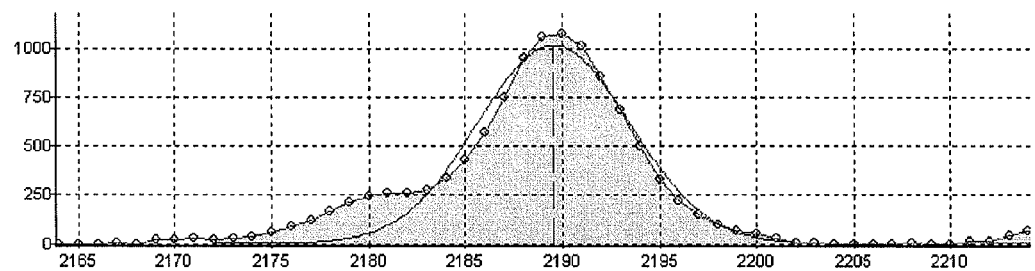
FIG. 41: Comparison of SGF to FFF for a −A/+A peak where the FFF properly evoked a Dual fit. (a) The resulting SGF fit has peak height and position values that deviate from the apparent height and maximum due to the −A peak. (b) The resulting FFF fit is able to properly identify and resolve the −A and +A peaks. The accuracy of the +A peak height and position are improved from that of the SGF fit.
Figure 41B:
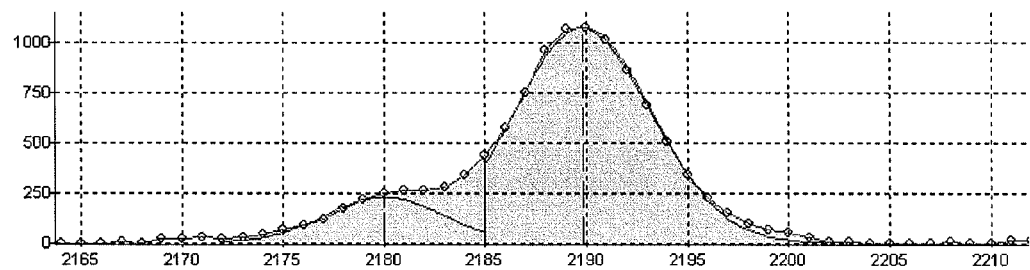
Figure 42A:
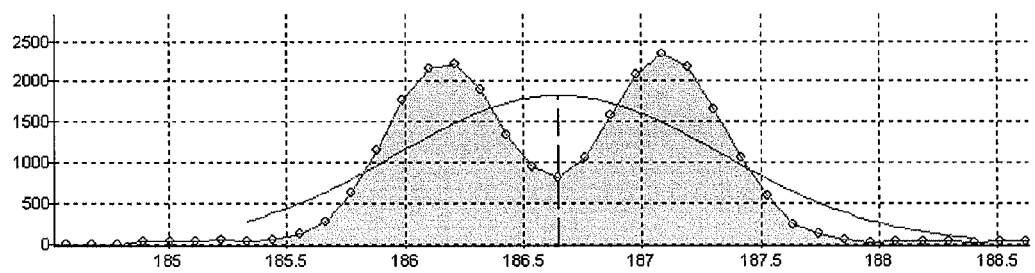
FIG. 42: Comparison of SGF to FFF fits for a dual peak where the FFF properly evoked a Dual fit. This window contains 9.3/10 alleles of the TH01 locus. (a) The resulting SGF fit is unable to resolve the two peaks into its two components. (b) The resulting FFF fit splits the dual peak separating the window into its two component peaks.
Figure 42B:
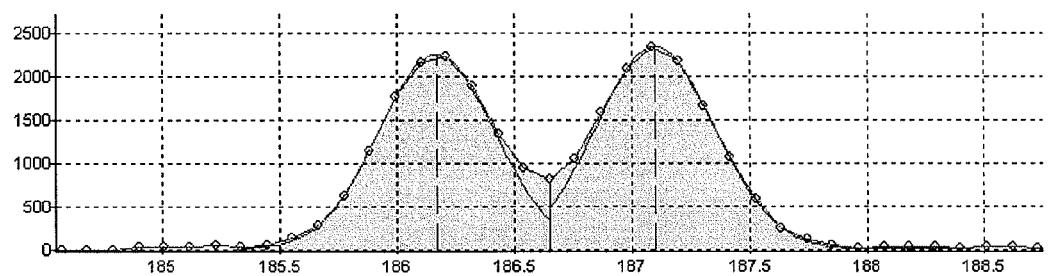
Figure 43:
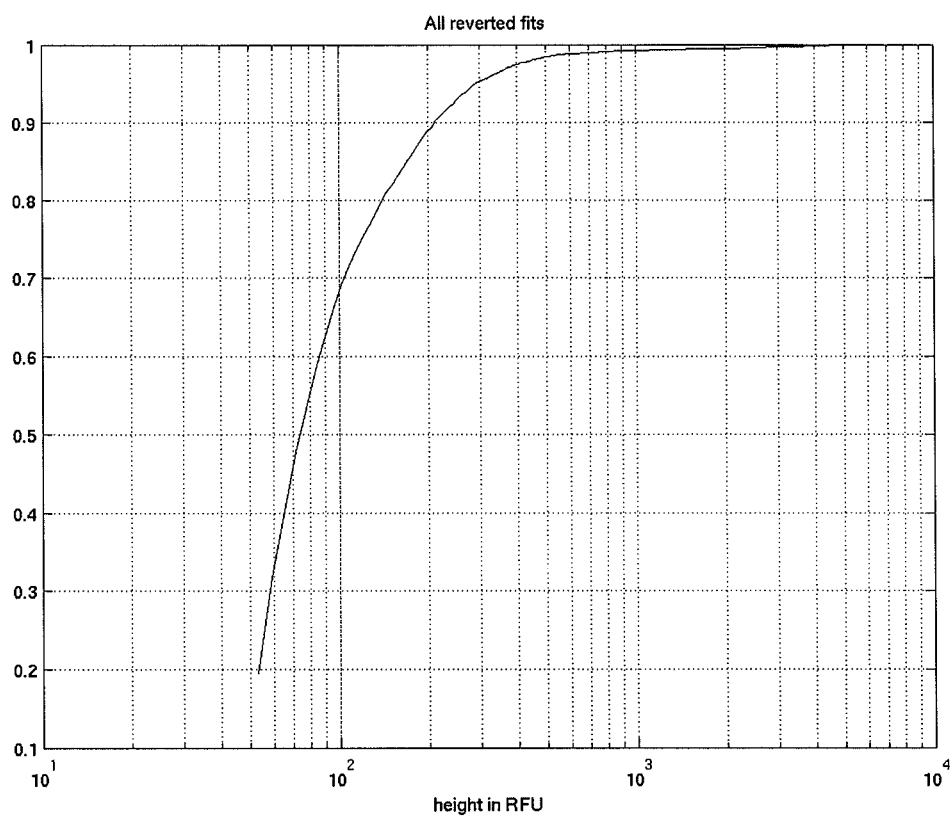
FIG. 43: Peak height distribution for all reverted peaks. The y-axis indicates the cumulative fraction of peaks that are below the corresponding peak height value shown in the x-axis. Among all reverted peaks, approximately 70% are under 100 RFU in height, 90% under 200 RFU, and 95% under 300 RFU. This indicates that the majority of peaks that are reverted are relatively small in amplitude and may be noise peaks in nature.

The next set of figures show the ability of the FFF to evoke a more advanced peak type to fit data with asymmetric and dual peaks. The improvement in the fit of asymmetric peaks is displayed in FIG. 40. The peak center position is improved by 0.75 scan units and the height is improved by 12 RFU. These differences are relatively small, but even a slight difference in the position and height of a peak can sometimes result in the wrong identification of an allele after the EXPERT SYSTEM expert rules are applied. A similar improvement occurs in the resolution of −A/+A dual peaks as shown in FIG. 41, which shows that two peaks (as they should be) are used to model the data in the overall data window which exhibit a pronounced left shoulder hump due to the presence of the −A peak. An essential ability that the fitter must possess is the ability to resolve overlapped peaks (when both peaks represent true alleles). FIG. 42 shows a fit of a data window containing the 9.3/10 allele peaks of the TH01 locus. In this type of situation, the inability to separate the peaks will cause more than just fitting error. The inability of the SGF to resolve the data into the two component peaks may cause DNA ladders to fail to be properly called or peaks to be completely missed.

EXAMPLE 3C

Statistics of Peak Fitting Results

The statistics from applying the fitter framework to over fifteen thousand peaks have been analyzed to determine the ability of the framework to satisfactorily fit real STR DNA data. The following discussion summarizes the statistics. The peak fits are discussed as a whole and then divided into two sets: regular fits and reverted fits. A regular fit refers to the fit that is accepted by the fitter framework after the fit type is evoked for the first time. A reverted fit refers to the fit type that is chosen from among all of the previously attempted fit types only after all of the fit types have failed to be accepted the first time each is evoked.

Table 6.3 gives the distribution of the final chosen fit types for all 17,377 peaks fitted in this study. It is evident that the majority of the peaks, 73%, are fitted satisfactorily by the Default (Gaussian) fit. The Hybrid fit, able to accommodate asymmetric peaks, was the chosen fit type for 16\% of the peaks. The Dual fit, which provides the ability to resolve overlapping peaks, was the chosen fit for 4% of the peaks.

The Narrow and Direct fit types comprised 4.3% and 2%, respectively of the total peak fits. The Saturated fit, which is only performed on the small amount of saturated data in the data set, was performed less than 1% of the time.

TABLE 6.4

Statistics for the fit types for all regular peaks in the study. The Default, Hybrid, and Dual fits make up 12,565 of the total 17,377 peaks, or 72.3%, The Saturated and Narrow fits comprise 803 out of the total 17,377 peaks, or 4.6%.

| Fit Type | Avg. # Iterations to Converge | # of Occurrences | Percent of Total |
|---|---|---|---|
| Total | 5.9 | 13368 | 100.00 |
| Direct | — | 0 | 0.00 |
| Default | 5.3 | 11421 | 85.44 |
| Hybrid | 23.8 | 460 | 3.44 |
| Dual | 10.1 | 684 | 5.12 |
| Saturated | 17.7 | 61 | 0.46 |
| Narrow | 0.0 | 742 | 5.55 |

The statistics are further broken down to give insight into the quality of the fit that was obtained for each fit type. Dividing the count of each fit type into regular and reverted fits allows more specific conclusions to be drawn. Table 6.4 contains the distribution statistics for the regular fits. These peak fits, with the exception of the Narrow and Saturated peaks, were accepted based on the peaks being able to be fitted by the respective fit type the first time it is evoked. This implies that the peak data are of high quality (fit residuals are within error envelope bounds), exhibiting very little unusual behavior that cannot be captured adequately by the respective peak model evoked. Overall, 72.3% of all peaks were fitted successfully under this criteria for the Default, Hybrid, and Dual fits combined. The quality of these peaks should be considered good because the center region of the peak (primary region) is within 5% of the primary envelope bound and the outside region of the peak (secondary region) is within 10% of the secondary error envelope bound on the initial attempt of the respective fit for Default and Hybrid fits, or 10% across the whole window for Dual fits. Saturated and Narrow fits are not included in this percentage count since they are not accepted based on their fit merit but evoked directly after Check Peak determines that they are the appropriate fit type based on the condition of the data. These statements do not imply that the other 27.7% of peak fits were unsuccessful, only that the peaks exhibit some characteristics that cannot be described well by the respective model equation along with the imposed acceptance criteria. However, these remaining peaks may still be adequately modeled by the final peak type chosen for it by the Revert function.

The reverted fits are a result of the Default, Hybrid, and possibly Dual fits containing excursions beyond the specified error envelope bounds, thereby failing to meet the fit acceptance criteria (Dual fits are only performed when a peak window matches the split criteria as set by the Check Fit function, see Example 2B). The Revert function then chooses the best of these three fits previously attempted, based on the one with the minimum MSE value. If none of the fit types converged or resulted in valid parameters, then the Direct fit function is called as a last resort. The distribution of the fit types as a result of having triggered the Revert function is shown in Table 6.5.

TABLE 6.5

Statistics for the fit types for all reverted peaks in the study. The reverted peaks make up 4,009 out of the total 17,377 peak fits attempted, or 23.1%

| Fit Type | Avg. # Iterations to Converge | # of Occurrences | Percent of Total |
|---|---|---|---|
| Total | 16.4 | 4009 | 100.00 |
| Direct | 0.0 | 350 | 8.73 |
| Default | 7.7 | 1288 | 32.13 |
| Hybrid | 23.5 | 2339 | 58.34 |
| Dual | 23.4 | 32 | 0.80 |
| Saturated | — | 0 | 0.00 |
| Narrow | — | 0 | 0.00 |

This table indicates that 90% of the reverted fits settle on the Default and Hybrid fit types. Note that the large percentage of Hybrid peaks results from the increased variability of the Hybrid model over the Gaussian model. Low amplitude peaks can often be better fitted with this model. Additionally, asymmetry in real peak data is sometimes not perfectly modeled by the Hybrid equation and small amplitude excursions may have occurred, even if the overall fit is fairly good. Less than 10% of the reverted peaks required a Direct fit of the peak. A smaller number of Direct fits is desirable since the Direct fit does not use an optimization to find its parameters. Only a very small number of dual peaks were the chosen fit type by the Revert function (less than 1%), which is expected since reverting to a dual fit requires a reduction of at least 40% in the MSE compared to the Default and Hybrid fits.

Because the reverted fits are chosen from the "best of the worst" previously attempted fits, it is difficult to determine their quality based on these statistics alone. Many of the fits contained in this set are peaks that contained a single excursion due to a noisy data point or a peak shape slightly deviating from the models' ability to accommodate it. Therefore, being a reverted peak does not automatically imply that the peak has something wrong with it or that the chosen model fit is not appropriate.

Figure 48:
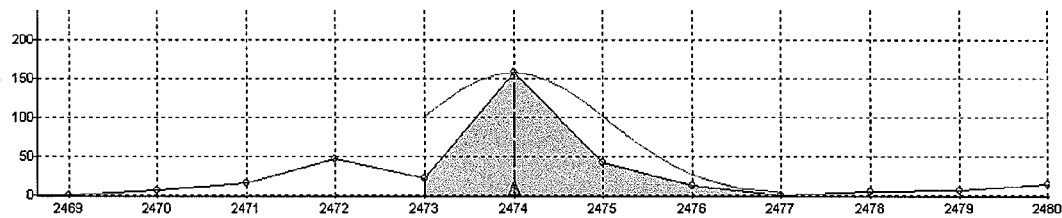
FIG. 48: Wide fitting of a narrow peak. Although the apparent peak height and center are fit will, the width is fitted too high based on the Direct fit using the size of the peak window to calculate the width.

FIG. 48 shows the distribution of reverted peaks with respect to their peak height to see if they can be low amplitude noise peaks. Noise peaks usually exhibit inconsistent peak data patterns that render a fit by an analytical model equation difficult.

Figure 44:
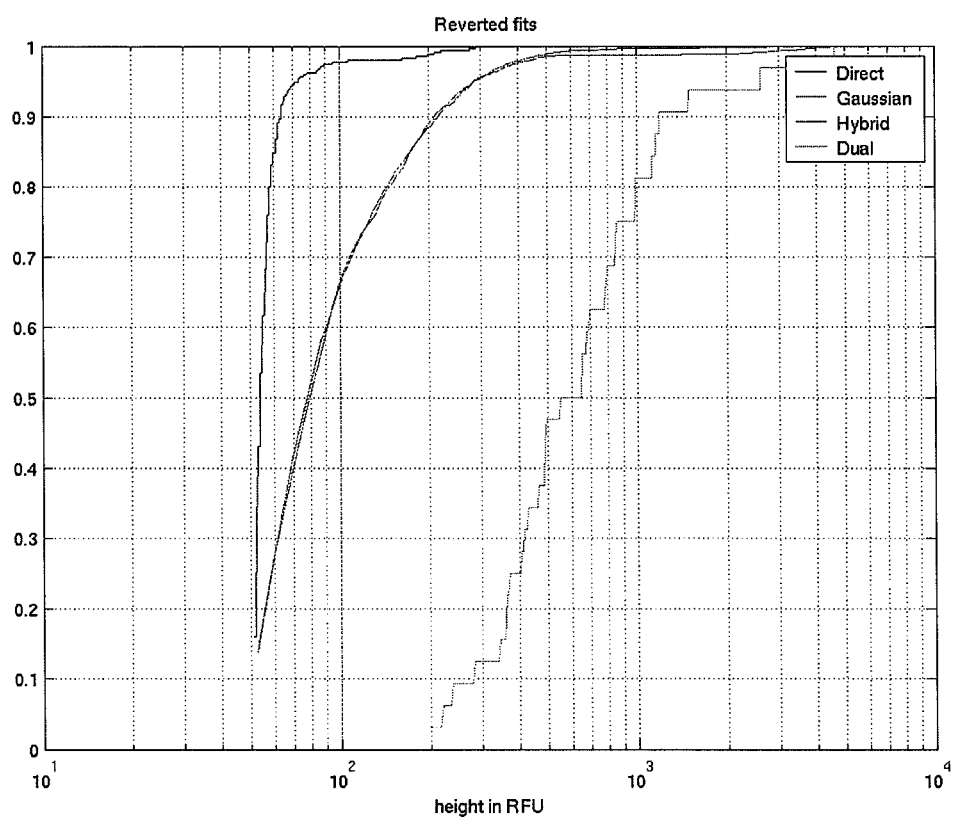
FIG. 44: Peak height distribution for reverted peaks of each fit type. The y-axis indicates the cumulative fraction of peaks that are below the corresponding peak height value shown in the x-axis. The majority Direct fits fall between 50 and 100 RFU, where the Gaussian and Hybrid fits are predominately under 300 RFU. Dual peaks, which represent only a small number of the reverted peaks, are higher in height and require an improvement over the Hybrid and Default fits in MSE in order to be chosen as the final fit type.
Figure 45:
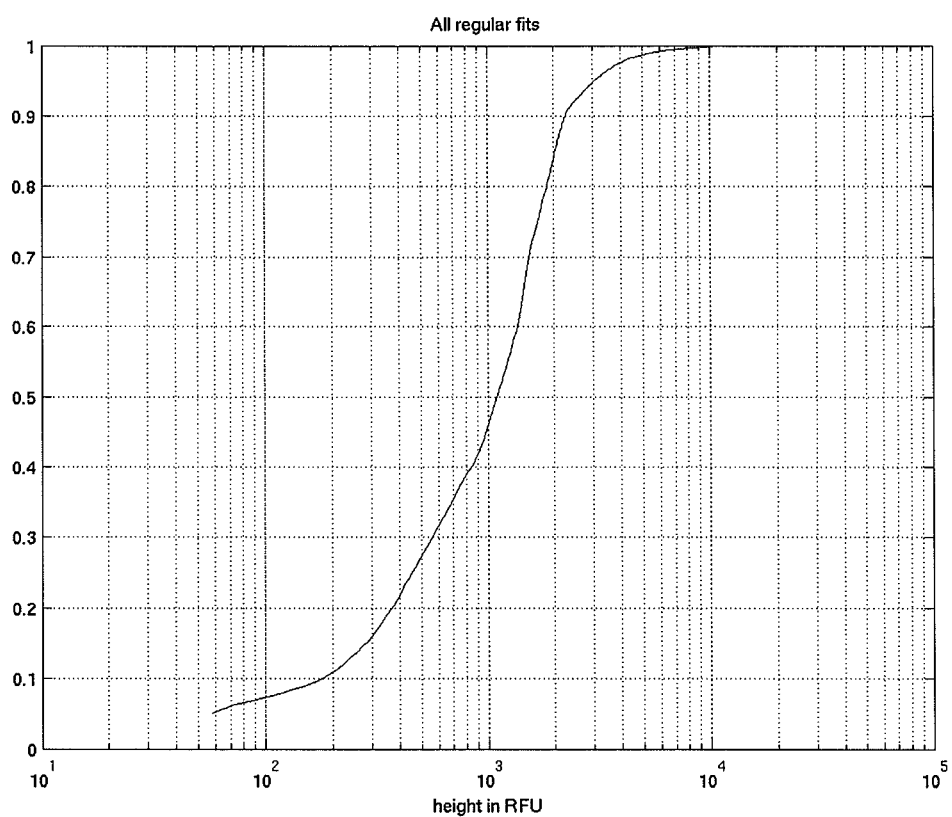
FIG. 45: Peak height distribution for all regular peaks. The y-axis indicates the cumulative fraction of peaks that are below the corresponding peak height value shown in the x-axis. Compared to the reverted peaks, the average height of the regular peaks is much higher. The height average is close to 1,000 RFU as compared to less than 100 RFU for reverted peaks.
Figure 46:
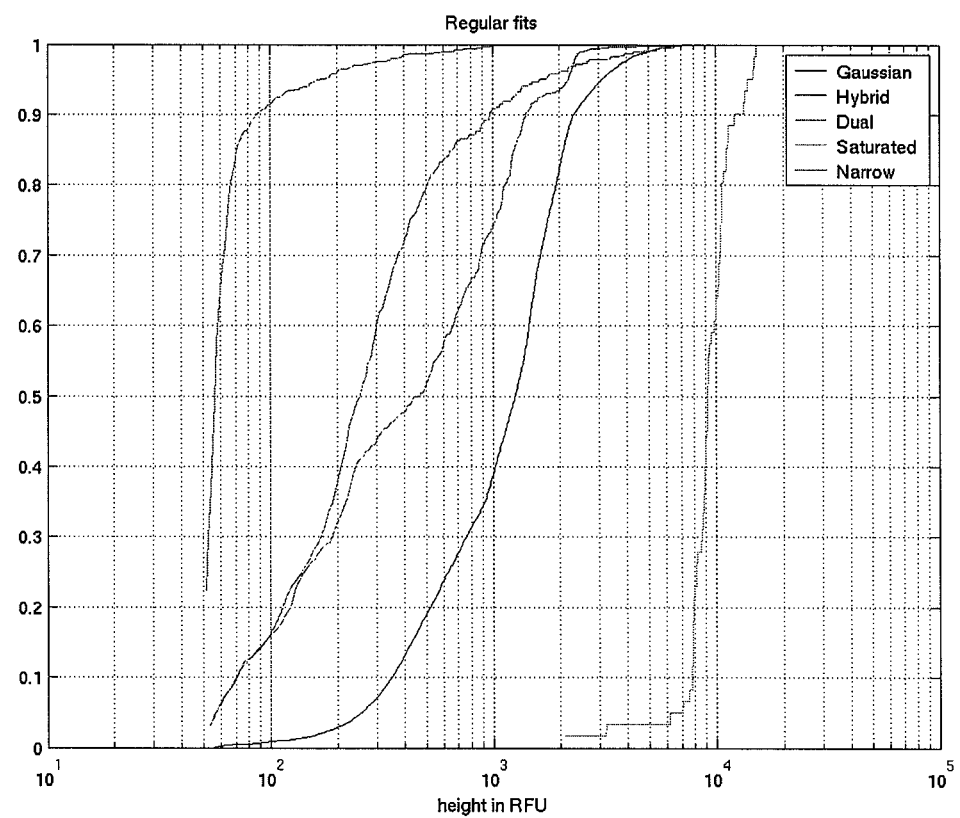
FIG. 46: Peak height distribution for regular peaks of each fit type. The y-axis indicates the cumulative fraction of peaks that are below the corresponding peak height value shown in the x-axis. The Narrow fits have very small heights in RFU and the Saturated fits very large heights in RFU, as would be expected. The Default, Hybrid, and Dual fits fall somewhere in the middle.

The majority of reverted peaks (around 95%) are found to be under 300 RFU in height compared to an average peak height of 1,000 in this study. FIG. 44 shows the respective distributions for each fit type reverted to (Default, Hybrid, Dual, and Direct). These distributions illustrate that the Gaussian and Hybrid reverted peaks are typically around a few hundred RFU while Direct peaks are generally under 100 RFU. As a comparison, the distributions for the regular peaks (including Saturated and Narrow fits) are given in FIGS. 45 and 46. It can be observed that the majority of regular peaks are above a few hundred RFU, with the average being closer to 1,000 RFU.

It can be seen that, in both the reverted and regular peaks, the directly fitted peaks (Narrow and Direct fits) are predominately very small in peak height. These generally correspond to the noise peaks that just barely exceed the 50 RFU peak detection threshold. Most of these are not true peaks and can be ignored.

TABLE 6.6

Effect of increasing the peak height threshold on the percentage of high quality fits. Considering all peaks (50 RFU height threshold) results in 72.3% of the data being of high quality fit. Raising the threshold to 200 RFU increases this to 95%.

| Height Threshold | % High Quality |
|---|---|
| 50 | 72.3 |
| 100 | 89.5 |
| 150 | 93.4 |
| 200 | 95.6 |
| 250 | 96.9 |
| 300 | 97.6 |
| 500 | 98.6 |

To test this postulate, an analysis was performed with the peak detection threshold raised from 50 to 200 RFU. Of the 17,377 peaks, 12,407 (71.4%) were found to be greater than 200 RFU in height. Of the 12,565 high quality fits (Default, Hybrid, and Dual), 11,863 are over 200 RFU. This means that 11,863/12,407, or 95.6%, of the peaks with peak height above 200 RFU are non-noise peaks and have high quality peak characteristics, all of which are able to be fitted well the first time that the appropriate peak type is evoked. With increasingly higher peak detection thresholds, an increasingly higher percentage of peaks are found to be of high quality. Results are shown in Table 6.6.

EXAMPLE 3D

Limitations of the Designed Fitter Framework

Figure 47:
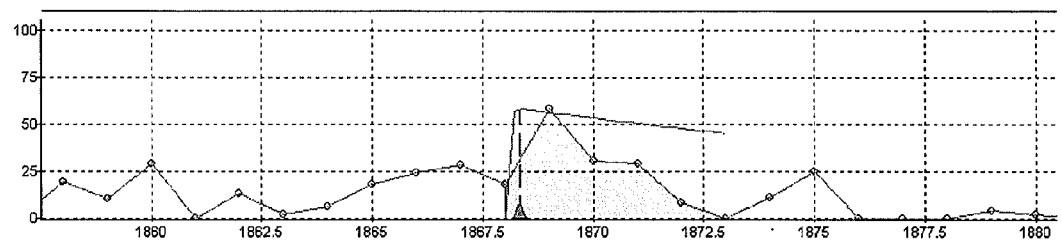
FIG. 47: Noise peak resulting in highly skewed peak fit.
Figure 49:
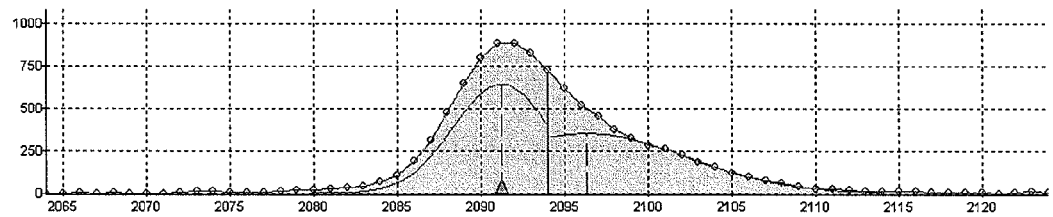
FIG. 49: Dual fit performed on a highly asymmetric peak. It is difficult to tell what type of fit is appropriate for this peak.
Figure 50:
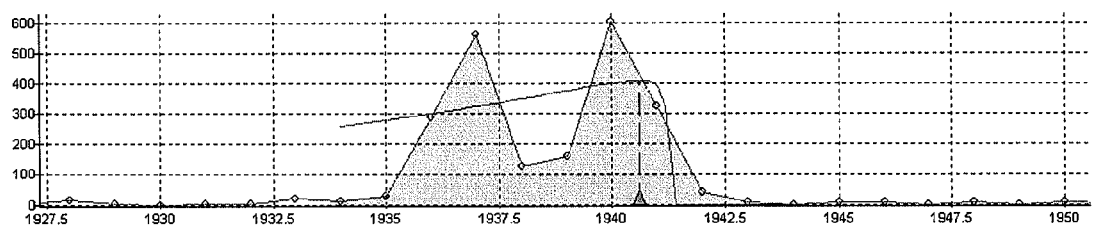
FIG. 50: Poorly fitted spike peak. The small number of points and highly atypical peak shape cause this type of peak to be difficult to model with any of the give peak models.

Although the fitting framework works fairly well, especially as the minimum peak threshold in RFU is raised, there are situations in which it does not function as desired. Small peaks and occasional spikes may not be fitted ideally but at least can be assigned peak parameters that generally describe the peak. FIG. 47 shows an example of a noise peak that results in a highly skewed Hybrid fit by the fitter framework. Although a Gaussian curve may visually model the peak slightly better, the Hybrid model gave a lower fitting error as measured by their MSE values. Peaks as that in FIG. 48 show the limitation of direct fitting (both Direct and Narrow fit types) to yield peak parameters based directly on the data contained in the window. The width assigned is too large for the peak given; however, the peak maximum height and position values appear to be appropriate. A more problematic issue is possible false triggering and accepting inappropriate fit types. FIG. 49 shows an example of a highly skewed peak, which has been fitted and resolved into two peaks by the peak fitter framework because data met the split peak criteria and were best fitted by the Dual peak model with respect to the specified fitting configuration parameter settings (see Example 2B). Although, with visual inspection, it is difficult to conclude if this peak can be regarded instead as a highly asymmetric peak. Unpredictable spikes or other anomalous peaks can also result in poor fit, as seen in FIG. 50.

Some of the less desirable fits, especially those of low amplitude noise peaks, are more of an issue with the peak detector functionality performed prior to peak fitting. A balance between the detector and the fitter must exist. For a given peak, the detector must gather a suitable number of points to represent that peak for the fitter to function well. If too few points are collected into the data window, the resulting fit may not represent the shape well. If too many points are collected, the peak fitter may be attempting to fit data not associated with the real peak or to fit potentially too many peaks present in the window. It should be noted that these non-desirable fits are in the minority and often are easily reconciled upon inspection by a human. If they occur too often, then they may be the result of poor quality data from bad experimental runs. Criteria developed for acceptance of peak fits and triggering of the next fit type are heuristic and can be tuned to accommodate different types of data. Fitter configuration parameters can be changed to trigger dual fits more conservatively if false Dual fits occur frequently. The parameters also govern to what degree of error fits are accepted.

Conclusions

Nonlinear fitting with a variety of peak model equations formed the basis for the fitting.

The Gaussian peak model was able to sufficiently fit the majority of the peaks, but non-ideal peaks required more advanced models. Two additional models were utilized, Hybrid and Dual, for the fitting of asymmetric and dual peaks, respectively. Fit types were developed to accommodate specialty peaks, such as narrow and saturated peaks. The flow of the fitting involved a sequential trying of different fits, until one was deemed acceptable based on a set of heuristic criteria. The concepts of error bounding envelopes and excursions were introduced as part of the criteria for triggering the next fit type. If no fit was accepted on the first pass, the fit would be reverted to the best of the fits previously tried. If still no fit could be used, the peak would be fitted directly without an optimization step.

Over fifteen thousand peaks were fitted using the fitter framework and results were analyzed. Results indicated that most peak data could be fitted satisfactorily using one of the three models on the first attempt (Default, Hybrid, or Dual).

BIBLIOGRAPHY

[1] http://www.appliedbiosystems.com
[2] http://www.solver.com
[3] http://www.mathworks.com
[4] http://www.math.nist.gov/tnt/index.html
[5] *Optimization Toolbox User's Guide*. The Math Works, Inc., 1999. Natick, Mass.
[6] F. Alsmeyer and W. Marquardt. Automatic generation of peak-shaped models. *Society for Applied Spectroscopy*, 58:986-994, 2004.
[7] J. J. Baeza-Baeza and M. C. García-Alvarez-Coque. Prediction of peak shape as a function of retention in reversed-phase liquid chromatography. *Journal of Chromatography A*, 1022:17-24, 2004.
[8] D. P. Bertsekas. *Nonlinear Programming: Second Edition*. Athena Scientific, 1999. Belmont, Mass.
[9] J. M. Butler. *Forensic DNA Typing*. Academic Press, 2001. San Diego, Calif.
[10] R. D. Caballero, M. C. García-Alvarez-Coque, and J. J. Baeza-Baeza. Parabolic-Lorentzian modified Gaussian model for describing and deconvolving chromatographic peaks. *Journal of Chromatography A*, 954:59-76, 2002.
[11] R. C. Eanes and R. K. Marcus. Peakfitter—an integrated Excel-based Visual Basic program for processing multiple skewed and shifting Gaussian-like spectral peaks simultaneously: application to radio frequency glow discharge ion trap mass spectrometry. *Spectrochimica Acta Electronica*, 55:403-428, 2000.
[12] C. Gomez (Ed.). *Engineering and Scientific Computing with Scilab*. Birkhauser, 1999. Boston, Mass.
[13] G. L. Erny. E. T. Bergström, and D. M. Goodall. Electromigration dispersion in capillary zone electrophoresis. Experimental validation of use of the Haarhoff-Van der Linde function. *Journal of Chromatography A*, 959:220-239, 2002.
[14] K. Lan and J. W. Jorgenson. A hybrid of exponential and Gaussian functions as a simple model of asymmetric chromatographic peaks. *Journal of Chromatography A*, 915:1-13, 2001.
[15] K. Levenberg. A method for the solution of certain problems in least squares. *Quarterly of Applied Mathematics*, 2:164-168, 1944.
[16] J. Li. Comparison of the capability of peak functions in describing real chromatographic peaks. *Journal of Chromatography A*, 952:63-70, 2002.
[17] V. B. Di Marco and G. G. Bombi. Mathematical functions for the representation of chromatographic peaks. *Journal of Chromatography A*, 931:1-30, 2001.
[18] D. Marquardt. An algorithm for least-squares estimation of nonlinear parameters. *SIAM Journal on Applied Mathematics*, 11:431-441, 1963.
[19] P. Nikitas, A. Pappa-Louisi, and A. Papageorgiou. On the equations describing chromatographic peaks and the problem of the deconvolution of overlapped peaks. *Journal of Chromatography A*, 912:13-29, 2001.
[20] S. C. Pai. Temporarily convoluted Gaussian equations for chromatographic peaks. *Journal of Chromatography A*, 1028:89-103, 2004.
[21] T. L. Pap and Zs. Pápai. Application of a new mathematical function for describing chromatographic peaks. *Journal of Chromatography A*, 930:53-60, 2001.
[22] B. Steffen, K. P. Müller, M. Komenda, R. Koppmann, and A. Schaub. A new mathematical procedure to evaluate peaks in complex chromatograms. *Journal of Chromatography A*, 1071:239-246, 2005.
[23] S. Walsh and D. Diamond. Non-linear curve fitting using Microsoft Excel Solver. *Talanta*, 42:561-572, 1995.
[24] J. Butler, *Forensic DNA typing*, Academic Press, 2001
[25] B. Budowle, "Probabilities of Alleles Distribution at 13 Loci," Personal Communication in January 2002.

We claim:

1. A computer implemented method of calling an allele by analyzing one of predetermined electrophoretic, chromatographic, and spectral two-dimensional graphic data input to a predetermined computer for implementing an expert system peak fitter framework, the computer outputting data to a graphical interface for display in which the graphic data of the display exhibit peaks, the computer implemented method to determine a fit of the graphic data to a peak data model comprising a default fit mathematical model, a hybrid peak model and a dual fit model, the expert system peak fitter framework comprising the default fit mathematical model and a check fit function for each of the default fit mathematical model, the hybrid peak model and the dual fit model, the computer implemented method comprising:

detecting a first peak of a plurality of peaks of said graphic data by identifying a potential peak as the first peak of said graphic data and an associated peak window of sufficient width to contain the first peak;

fitting the graphic data to the default fit mathematical model comprising one of a Gaussian and a Gaussian-Lorentzian model, wherein the default fit model determines an initial set of peak parameters to fit said graphic data within said associated peak window, the set of peak parameters comprising a peak height and a peak center location within said associated peak window;

using a check fit function to check said fit of said graphic data to said default fit mathematical model and, if peak parameters fall within an acceptable range, then, accepting an associated peak fit type and updating the determined set of peak parameters for the graphic data based on the fit to said default fit model;

if the associated peak fit type is not accepted, fitting the graphic data to said hybrid peak model, said hybrid peak model comprising a modified exponential Gaussian hybrid model for using the graphic data within said associated peak window that exceeds a peak height threshold of a predetermined per cent of a detected peak height maximum value, calculating a skewness parameter for the associated peak window, and fitting the first detected peak of the plurality of peaks if the skewness parameter indicates one of peak fronting and tailing;

using a check fit function to check said fit of said graphic data to said hybrid peak model and, if peak parameters fall within an acceptable range, then accepting an associated hybrid peak fit type, and updating the determined set of peak parameters for the graphic data based on the fit to said hybrid peak model;

if the associated hybrid peak fit type is not accepted, fitting the graphic data to said dual fit model comprising detecting first and second proximate peaks of said graphic data within said associated peak window;

checking the fit of the graphic data to said dual fit model within the associated peak window; if peak parameters fall within an acceptable range, then accepting an associated dual peak fit type, and updating the determined set of peak parameters for the graphic data based on the fit to said dual fit model;

if the associated dual peak type is not accepted, applying a revert function to determine the best fit from the default fit mathematical model, hybrid peak model, and dual fit model; and repeating the fitting and checking the fit for a next detected peak of the plurality of peaks within a next associated peak window to identify a peak fit and accept an associated peak fit type the graphic data within the next associated peak window;

the analysis of said graphic data resulting in automatic peak processing, by the expert system peak fitter framework, the analysis of the two-dimensional graphic data being carried out on the predetermined computer.

2. The method of calling an allele according to claim 1, said determined set of peak parameters comprising the detected peak height maximum value, the peak center location, and a peak width, said updating comprises determining a parameter vector that minimizes cost calculated at one-half of the total sum of squares of errors between the two-dimensional graphic data within an associated peak window and an applied peak data model.

3. The method of calling an allele according to claim 1, the method further comprising:

analyzing non-ideal peak types by applying one of the hybrid peak model for determining the peak skewness parameter indicative of the one of peak fronting and tailing and said dual fit model for determining the peak heights, the peak center locations, and peak widths for first and second peaks occurring proximate to one another within said associated peak window, the dual fit model comprising a dual Gaussian peak model adapted for resolving a −A/+A peak.

4. The method of calling an allele according to claim 1, comprising further graphic data processing for detecting and fitting a saturated peak, said graphic data comprising an electropherogram, the method further comprising graphic data processing to indicate a start of a region of interest encompassing allelic peak data within said associated peak window of the detected saturated peak, the method comprising: determining the start of the region of interest of the graphic peak data within said associated peak window of the detected saturated peak, discarding saturated points of the graphic peak data and reconstructing a saturated region of the saturated points of the saturated peak using the Gaussian model.

5. The method of calling an allele according to claim 1, further comprising data conditioning, said data conditioning including performing baseline correction before color separation and identifying an end of a primer peak indicative of a start of allelic information.

6. The method of calling an allele according to claim 1, further comprising applying a color matrix to multicolor channel electropherogram data.

7. The method of calling an allele according to claim 2, said peak width determined by calculating a full width half maximum value related to a horizontal distance between points to a left side and to a right side of a peak where a signal value is half its peak height maximum value.

8. The method of calling an allele according to claim 1, the method further comprising:

analyzing non-ideal peak types by applying one of the hybrid peak model for determining the peak skewness parameter indicative of the one of peak fronting and tailing and said dual fit model for determining the peak heights, the peak center locations, and peak width for first and second peaks occurring proximate to one another within said associated peak window, the dual fit model comprising a dual Gaussian peak model adapted for resolving a TH01 9.3/10 peak.

9. The method of calling an allele according to claim 6, further comprising calibrating a size of DNA fragments using an internal sizing standard on one of at least two dye channels by capillary electrophoresis.

10. The method of calling an allele according to claim 1, further comprising detecting allele loci via one of short tandem repeat or Y-type short tandem repeat.

11. The method of calling an allele according to claim 5, said baseline correction comprising a windowing median filter having a sliding window larger in size than a typical number of points of a peak of the plurality of peaks within said associated peak window, the baseline correction comprising choosing a reference point below a median value and subtracting a value of signal at the reference point to provide a baseline corrected graphical plot.

12. The method of calling an allele according to claim 6, further comprising separating colors of spectra to reveal peaks.

13. The method of calling an allele according to claim 1, further comprising calling an allele responsive to the plurality of peaks of the spectral two dimensional graphic data each being fitted to a peak data model and associated peak fit type accepted for a plurality of associated peak windows for the plurality of peaks.

14. The method of calling an allele according to claim 1 wherein the modified exponential Gaussian hybrid model comprises:

$$f(x, p) = \begin{cases} Ae\left(-\frac{(x-x_c)^2}{\sigma^2 + \tau(x-x_c)}\right), & \sigma^2 + \tau(x-x_c) > 0; \\ 0, & \sigma^2 + \tau(x-x_c) \leq 0, \end{cases}$$

with $$p = [A, x_c, \sigma, \tau],$$

wherein A is the maximum peak height, $\chi_c$ is the peak center position, $\sigma$ is a width measure, and $\tau$ is the peak skewness parameter, the parameter $\tau$ indicating peak tailing if positive and peak fronting if negative.

15. The method of calling an allele according to claim 1 wherein the dual Gaussian fit model comprises:

$$f(x, p) = A_1 e^{-\left(\frac{x-x_{c1}}{\sigma_1}\right)^2} + A_2 e^{-\left(\frac{x-x_{c2}}{\sigma_1}\right)^2},$$

with $$p = [A_1, x_{c1}, \sigma_1, A_2, x_{c2}, \sigma_2],$$

where $A_1$ and $A_2$ are the peak maximum heights, $\chi_{c1}$ and $\chi_{c2}$ the peak centers, and $\tau_1$ and $\tau_2$ the width measures of the two peaks, respectively.

16. A method of calling an allele according to claim 1 wherein the dual fit model further comprises forming a sub-window of the associated peak window to identify one of the first and second proximate peaks as having a larger maximum value, collecting all points monotonically decreasing away from the associated peak window's maximum value to the left of the first proximate peak and the second proximate peak having the larger maximum value and to the right of the first proximate peak and the second proximate peak having the larger maximum value within a formed sub-window of the associated peak window; performing a first Gaussian fit using the points of the sub-window; subtracting the fitted points from the points of the associated peak window and performing a second Gaussian fit on the points resulting from the subtraction over the associated peak window to identify one of the first and the second proximate peak having the smaller maximum value.

17. A method of calling an allele according to claim 1 further comprising using the revert function for determining a best fit among a default fit result of said default fit mathematical model, a hybrid fit result of said modified exponential Gaussian hybrid model and a dual peak fit result of said dual Gaussian fit model depending on convergence and low mean square error and parameter values fall within predetermined ranges.

18. A method of calling an allele according to claim 1 further comprising determining a calculated fit window, the calculated fit window being a sub-window of the associated peak window.

19. A method of calling an allele according to claim 1, the analysis of the plurality of peaks of the graphic data resulting in automatic peak processing by the expert system peak fitter framework to call the allele.

20. A computer implemented method of calling an allele by analyzing one of electrophoretic, chromatographic, and spectral two dimensional graphic data input to a predetermined computer for implementing an expert system peak fitter framework, the computer outputting data to a graphical interface for display in which the graphic data exhibit peaks to determine a fit of the graphic data to a peak data model of the expert system peak fitter framework, the computer implemented method comprising:

detecting a first peak of a plurality of peaks of said graphic data by identifying a potential peak as the first peak of said graphic data and an associated peak window of sufficient width to contain the first peak;

fitting the graphic data to a default mathematical model of the expert system peak fitter framework comprising one of a Gaussian and Gaussian-Lorentzian model, wherein the default fit model determined a set of peak parameters to fit said graphic data within said associated peak window, the set of peak parameters comprising a peak height and a peak center location within the associated peak window;

using a first check fit function to check said fit of said graphic data to said default fit mathematical model and, if peak parameters fall within an acceptable range, then, accepting an associated peak fit type and updating the determined set of peak parameters for the graphic data based on the fit to the default fit model;

if the associated peak fit type is not accepted, fitting the graphic data to a hybrid peak model of the expert system peak fitter framework using the graphic data within said associated peak window that exceeds a peak height threshold of a predetermined percent of a detected peak height maximum value, calculating a skewness parameter for the associated peak window, and fitting the first detected peak of the plurality of peaks if the skewness parameter indicates one of peak fronting and tailing;

using a second check fit function to check said fit of said graphic data to said hybrid peak model and, if peak parameters fall within an acceptable range, then accepting an associated hybrid peak fit type and updating the determined set of peak parameters for the graphic data based on the fit to said hybrid peak model;

if the associated hybrid peak fit type is not accepted, fitting the graphical data to said dual fit model if said graphical data exhibits dual peaks; checking the fit of the graphic data to the dual fit model within the associated peak fit window; if peak parameters fall within an acceptable range, then accepting an associated dual peak fit type, and updating the determined set of peak parameters for the graphic data based on the fit to said dual fit model;

if the associated dual peak type is not accepted, applying a revert function to determine the best fit among the default fit model, the hybrid peak model and the dual fit model; and repeating the fitting and checking the fit for the peaks of the plurality of peaks of the graphic data to identify a peak fit and accept an associated peak fit type;

the analysis of graphic data resulting in automatic peak processing by the expert system peak fitter framework to accept an associated peak fit type for each of the plurality of peaks of the graphic data to call an allele, the analysis of the two-dimensional graphic data being carried out on the predetermined computer.

21. The method of calling an allele according to claim 20, the expert system peak fitter framework further comprising a special fit function to determine if a type of said peak of said plurality of peaks is one of narrow, saturated and other before applying the default mathematical model, the hybrid peak model, the dual fit model and the revert function as necessary to fit a given peak of the plurality of peaks of graphic data;

determining a fitted peak by comparing said peak with expected peak parameter values if said peak type is one of narrow and saturated; and applying one of said default, hybrid, and dual peak models and said revert function if said peak type is other.

22. The method of calling, an allele according to claim 21, the expert system peak fitter framework further comprising:
performing the revert function to determine if a previously determined fit is a best fit depending on convergence and low mean square error if said peak type is other and parameter values of said peak do not fit expected peak parameter values for one of said default mathematical model, hybrid peak model and said dual peak model.

23. The method of calling an allele according to claim 22, further comprising using a direct fit if said revert function does not result in an acceptable fit.

24. A computer implemented method of calling an allele by analyzing one of predetermined electrophoretic, chromatographic, and spectral two dimensional graphic data input to a predetermined computer for implementing an expert system peak fitter framework, the computer outputting data to a graphical interface for display in which the graphic data exhibit peaks to determine a fit of the graphic data to a peak data model of the expert system peak litter framework, the method comprising:
detecting a first peak of a plurality of peaks of said graphic data by identifying a potential peak as the first peak of said graphic data and an associated peak window of sufficient width to contain the first peak;
fitting the graphic data to a default mathematical model of the expert system peak fitter framework comprising one of a Gaussian and Gaussian-Lorentzian model to determine a set of peak parameters to fit said graphic data to said default mathematical model;
using a check fit function to check said lit of said graphic data to said default mathematical model and, if peak parameters fall within an acceptable range, then, accepting an associated peak fit type and updating the determined set of peak parameters for the graphic data based on the fit to said default model;
if the associated peak fit type is not accepted, fitting the graphic data to a hybrid peak model and then to a dual fit model for further analysis of said graphic data if a check fit function is not satisfied for the hybrid peak model and accepting an associated peak fit type and updating the determined set of peak parameters depending on whether the hybrid peak type or the dual fit type is accepted for the peak of the plurality of peaks;
if one of the associated hybrid or dual peak fit types is not accepted, applying a revert function to determine a best fit among the default fit model, the hybrid model and the dual fit model; and
repeating the fitting and checking the fit for a next detected peak of the plurality of peaks within a next associated peak fit window to identify a peak fit and accept an associated peak fit type for the graphic data within the next associated peak window;
said check fit function being responsive to each of the default mathematical model, the hybrid peak model and the dual peak model for checking the peak fit and further determining one of a default fit, a hybrid fit or dual peak fit from one of the default mathematical model, the hybrid peak model and the dual fit model and the revert function resulting in automatic peak fit processing by the expert system peak fitter framework to accept the associate peak fit type and to call an allele, the analysis of the two-dimensional graphic data being carried out on the predetermined computer; and
baseline correction to identify an end of a primer peak indicative of a start of allelic information, the baseline correction comprising a windowing median filter having a sliding window larger in size than a typical number of points of a peak of the plurality of peaks within the associated window for the peak, the baseline correction comprising choosing a reference point below a median value and subtracting a value of signal at the reference point to provide a baseline corrected graphical plot of the plurality of peaks.

25. The method of calling an allele according to claim 24, each of said default mathematical model, said hybrid peak model, and said dual fit model having an associated peak fitting function and a cost function involving calculation of the sum of squares error between said associated peak fitting function and said graphic data.

* * * * *